United States Patent [19]
Jacobs et al.

[11] Patent Number: 5,750,384
[45] Date of Patent: May 12, 1998

[54] L5 SHUTTLE PHASMIDS

[75] Inventors: William R. Jacobs, City Island, N.Y.; Graham F. Hatfull, Pittsburgh, Pa.; Stoyan Bardarov, Bronx, N.Y.; Ruth McAdam, Utrecht, Netherlands

[73] Assignees: Albert Einstein College of Medicine of Yeshiva University, a division of Yeshiva University, Bronx, N.Y.; University of Pittsburgh, Pa.

[21] Appl. No.: 247,901

[22] Filed: May 23, 1994

Related U.S. Application Data

[63] Continuation-in-part of Ser. No. 57,531, Apr. 29, 1993, abandoned, which is a continuation-in-part of Ser. No. 833,431, Feb. 7, 1992, abandoned.

[51] Int. Cl.$^6$ .............................. C12N 15/64; C12N 15/74
[52] U.S. Cl. ................................... 435/172.3; 435/320.1
[58] Field of Search ........................... 435/5, 6, 69.1, 435/69.8, 172.3, 235.1, 320.1; 935/31

[56] References Cited

U.S. PATENT DOCUMENTS

| | | | |
|---|---|---|---|
| 4,861,709 | 8/1989 | Ulitzer et al. | 435/6 |
| 5,504,005 | 4/1996 | Bloom et al. | 435/235.1 |

FOREIGN PATENT DOCUMENTS

WO9316172  8/1993  WIPO.

OTHER PUBLICATIONS

Graham F. Hatfull et al., entitled "DNA sequence, structure and gene expression of mycobacteriophage L5: a phage system for mycobacterial genetics." *Molecular Microbiology*, pp. 395–405 (1993).

Lee et al. (1991) Site-specific integration of mycobacteriophage L5: integration-proficient vectors for Mycobacterium smegmatis, Mycobacterium tuberculosis, and bacille Calmette-Guerin. Proc. Natl. Acad. Sci. USA 88:3111–3115, Apr. 1991.

Snapper et al. (1988) Lysogeny and transformation in mycobacteria: stable expression of foreign genes. Proc. Natl. Acad. Sci. USA 85:6987–6991, Sep. 1988.

*Primary Examiner*—George C. Elliott
*Assistant Examiner*—Robert Schwartzman
*Attorney, Agent, or Firm*—Amster, Rothstein & Ebenstein

[57] ABSTRACT

This invention is directed to L5 shuttle phasmids capable of delivering foreign DNA into mycobacteria and to methods of producing L5 shuttle phasmids. In addition, this invention is directed to a method of generating mycobacterial mutations and to a method of producing mycobacterial vaccines.

20 Claims, 19 Drawing Sheets

FIG. 12

L5 SHUTTLE PHASMIDS

CROSS-REFERENCE TO RELATED APPLICATIONS

This Application is a Continuation-In-Part of U.S. patent application Ser. No. 08/057,531 filed Apr. 29, 1993, entitled MYCOBACTERIAL SPECIES-SPECIFIC REPORTER MYCOBACTERIOPHAGES, abandoned, which is a Continuation-In-Part of U.S. patent application Ser. No. 07/833,431 filed Feb. 7, 1992 entitled MYCOBACTERIAL SPECIES-SPECIFIC REPORTER MYCOBACTERIOPHAGES, abandoned.

STATEMENT OF GOVERNMENT INTEREST

This invention was made with government support under Grant Numbers A127235, A126170, A128927 and A123545. As such, the government has certain rights in the invention.

FIELD OF THE INVENTION

This invention relates to L5 shuttle phasmids which are capable of delivering foreign DNA into mycobacteria. The L5 shuttle phasmids of the invention are used to generate mycobacterial mutations, which can be used to produce mycobacterial vaccines.

BACKGROUND OF THE INVENTION

Tuberculosis (which includes infection caused by *M. tuberculosis*, *M. bovis*, BCG and *M. africanum*) remains the largest cause of human death in the world from a single infectious disease, and is responsible for one in four avoidable adult deaths in developing countries. In addition, in 1990, there was a 10% increase in the incidence of tuberculosis in the United States.

In the past, infection with drug-sensitive strains of the *M. tuberculosis* complex had been cured with certain antibiotics, including isoniazid, rifampicin, ethionamide and pyrazinamide. However, resistance to isoniazid and other antibiotic drugs has developed in many strains of *M. tuberculosis*. This has resulted in the search for an effective vaccine against *M. tuberculosis*. Further, this has enhanced the need to develop new drugs which are effective against drug-resistant strains of *M. tuberculosis*. It is therefore desirable to develop molecular and genetic tools which can be utilized to understand the pathways involved in invasion, survival and persistence of *M. tuberculosis* and in the development of vaccines and new drugs.

The creation of mutants in *M. tuberculosis* and BCG is of essential importance in the analysis of *M. tuberculosis* and BCG gene function. Auxotrophic mutants have been isolated in *M. smegmatis* by both shuttle mutagenesis and N-methylN'-nitroso-N-nitrosoguanidine treatment followed by isoniazid enrichment. These methods, however, are less effective in the *M. tuberculosis* complex (*M. tuberculosis*, *M. bovis*, *M. miroti* and *M. africanum*) due to current difficulties in performing homologous recombination, which is required by the shuttle mutagenesis procedure. Also, the tendency of mycobacteria to clump limits the use of traditional mutagens and makes positive selection advantageous.

Because the creation of mutants in *M. tuberculosis* and BCG is of essential importance in the analysis of gene function, it is desirable to develop effective means and methods for delivering foreign DNA into *M. tuberculosis* and BCG. The insertion of foreign DNA into *M. tuberculosis* and BCG mycobacteria would provide the necessary tools for understanding the mechanisms by which these mycobacteria survive and replicate. In addition, it would provide valuable tools for the development of vaccines and new drugs effective in the treatment of infection caused by *M. tuberculosis* and BCG.

It is therefore and object of this invention to provide shuttle phasmids capable of delivering foreign DNA into mycobacteria.

It is another object of this invention to provide a method of producing shuttle phasmids capable of delivering foreign DNA into mycobacteria.

It is a further object of this invention to provide a method of generating mycobacterial mutations.

It is another object of this invention to provide mycobacterial mutants.

It is a still further object of this invention to provide a method of producing a mycobacterial vaccine.

SUMMARY OF THE INVENTION

This invention is directed to L5 shuttle phasmids capable of delivering foreign DNA into mycobacteria, which shuttle phasmids comprise an L5 mycobacteriophage containing an *E. coli* bacteriophage lambda cosmid inserted into a non-essential region of the L5 mycobacteriophage genome.

This invention is further directed to a method of generating mycobacterial mutations comprising producing a mycobacteriophage L5 shuttle phasmid containing a cosmid and a transposon therein, propagating the L5 shuttle phasmid, and infecting mycobacteria with the propagated L5 shuttle phasmids so as to cause delivery of the transposons from the L5 shuttle phasmids to the chromosomes of the mycobacteria, thereby causing mutations in the genes of the mycobacteria to occur. Once mycobacterial mutations have occurred, a marker gene present in the transposons is selected for in order to identify mycobacterial mutants in which the transposons have been delivered, and the mutants can be screened to identify a mutant of interest, such as an avirulent mutant. Certain mutants, including avirulent mutants can be used as mycobacterial vaccines.

In addition, this invention is directed to a method of determining whether an L5 gene is essential for L5 propagation. In order to perform this, a mutation of an L5 gene is generated utilizing a cosmid form of an L5 shuttle phasmid and recombinant DNA methodology so as to obtain an L5 shuttle phasmid mutant. The L5 shuttle phasmid mutant is propagated and then transfected in *M. smegmatis* in order to determine whether plaques have formed, the presence of plaques indicating that the L5 gene is not essential for L5 propagation.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 1 represents the double-cos vector pYUB328 derived from super cos vector. pYUB328 incorporates pak I sites blanking the BAMHI and NorI sites into which random fragments can be cloned. Since mycobacterial genomes do not have pacI sites in their chromosomes, the pYUB328 vector allows for the release of the cloned fragment. pYUB328 contains an *E. coli* origin in an ampicillin-resistant gene and bacteriophage lambda cos sequences;

FIG. 2 represents a schematic diagram of L5 shuttle phasmid construction;

FIG. 3 represents a schematic diagram of the L5 genome highlighting the L5 cohesive (cos) and the integration regions, immunity regions, and DNA polymerase regions;

Figure 8:
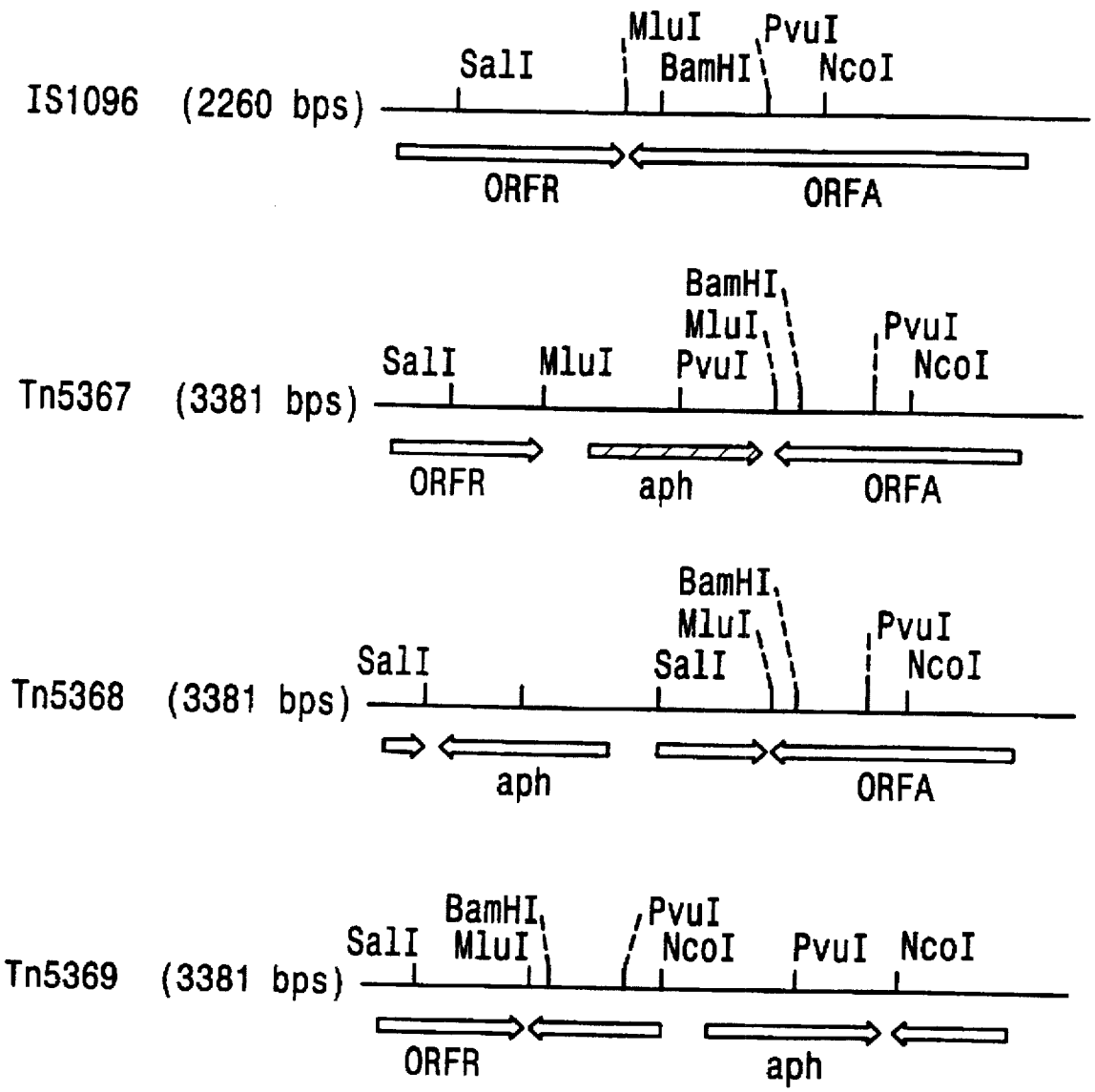
Figure 9A:
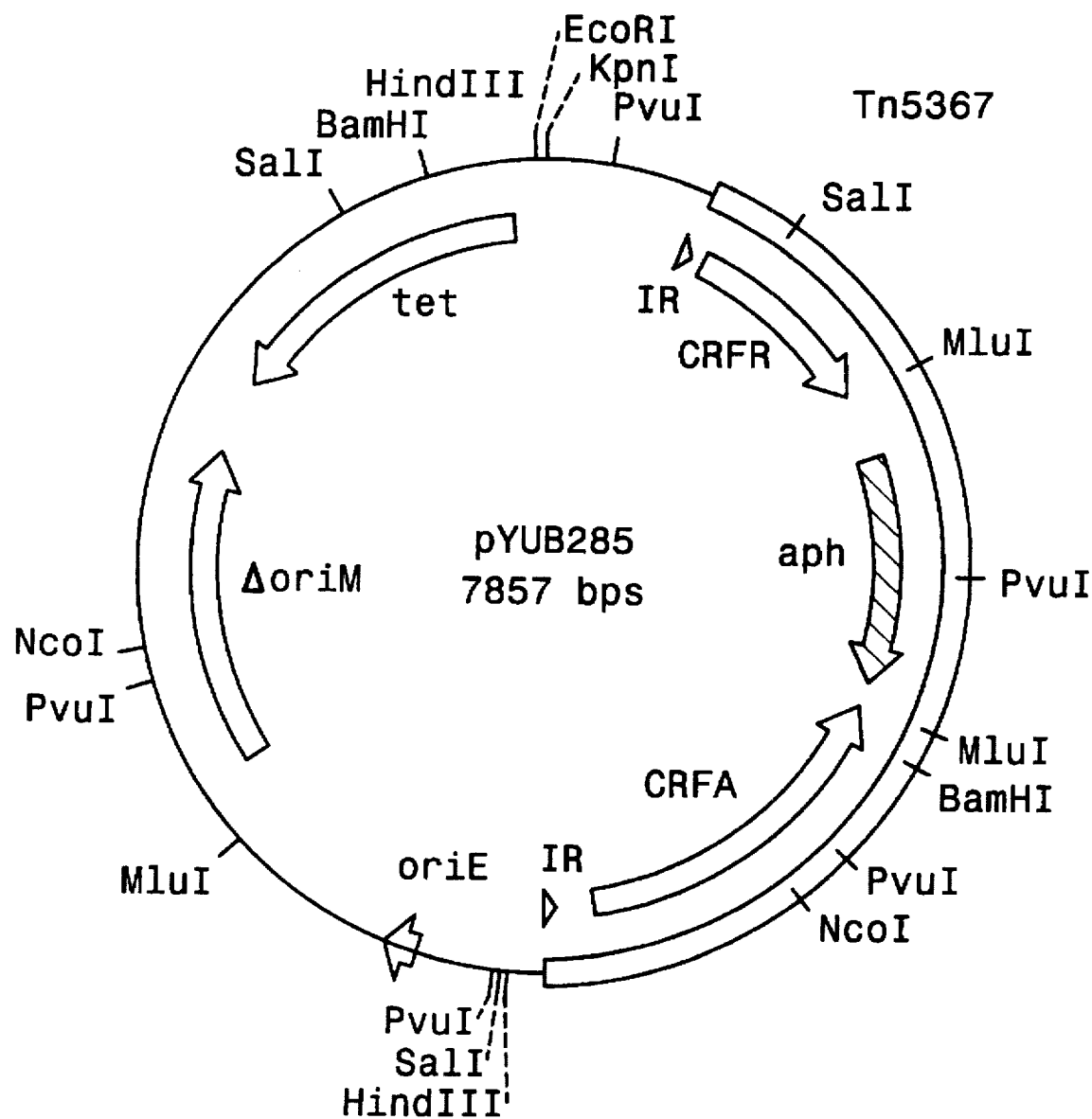
Figure 9B:
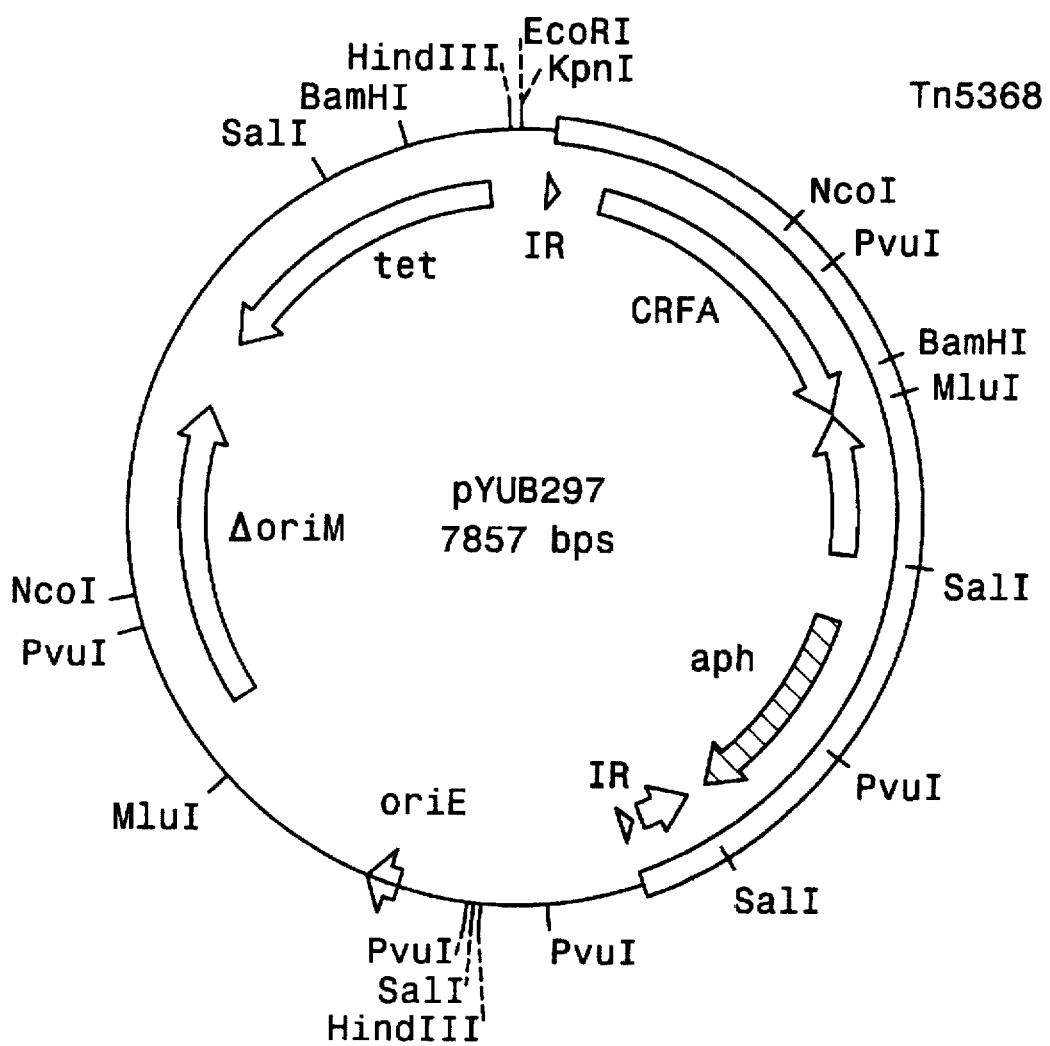
Figure 9C:
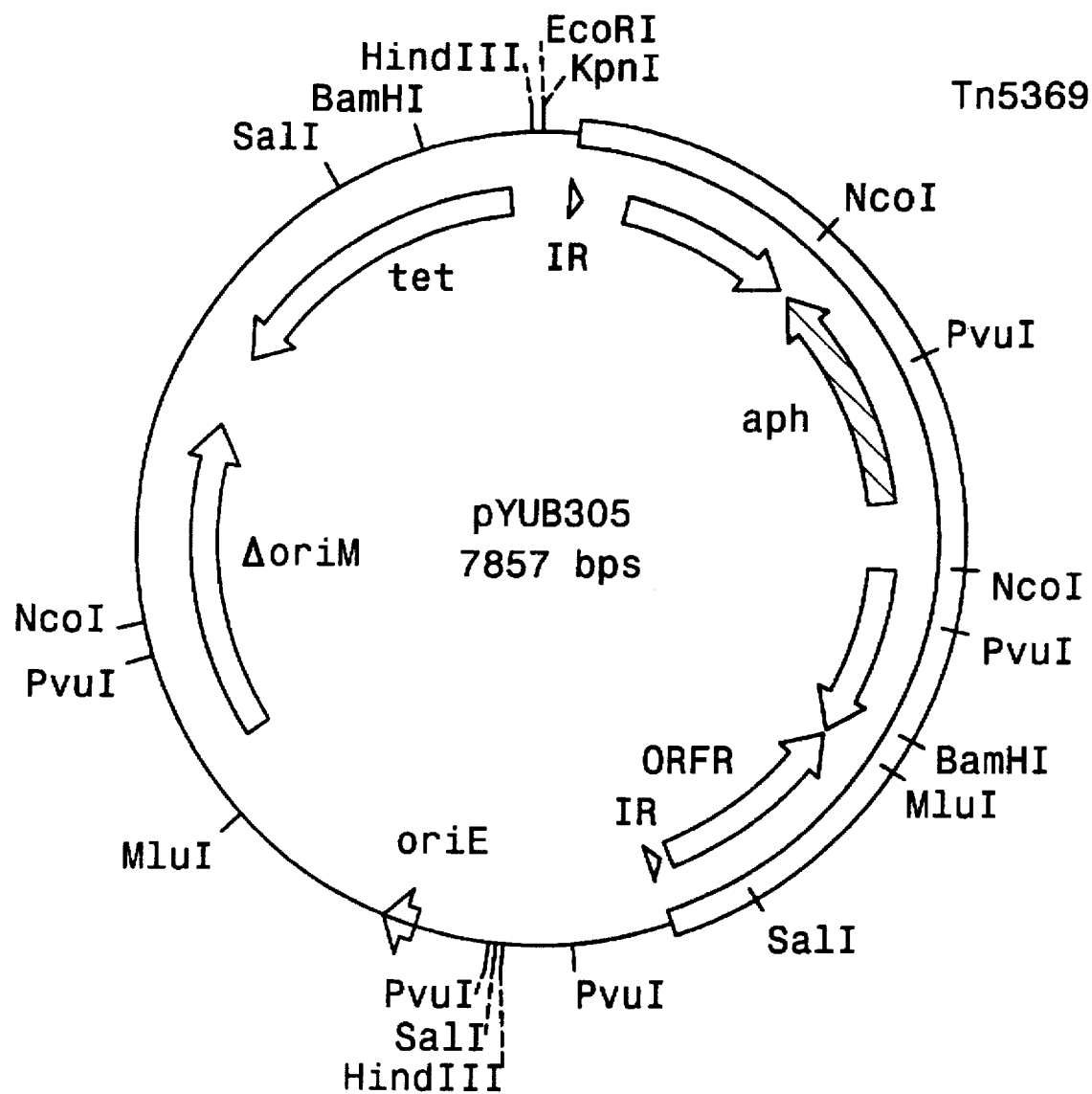
Figure 9D:
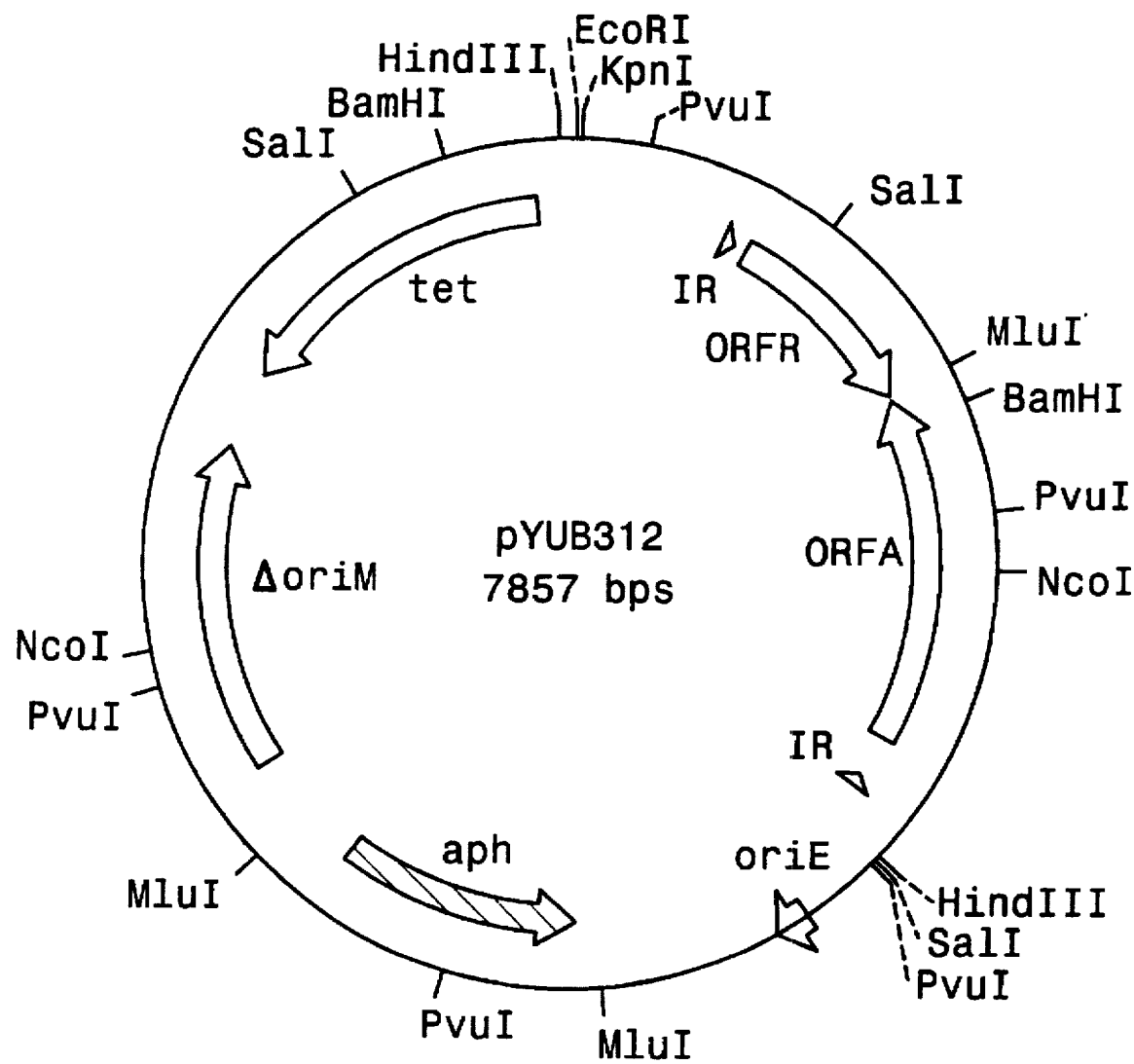
Figure 10:
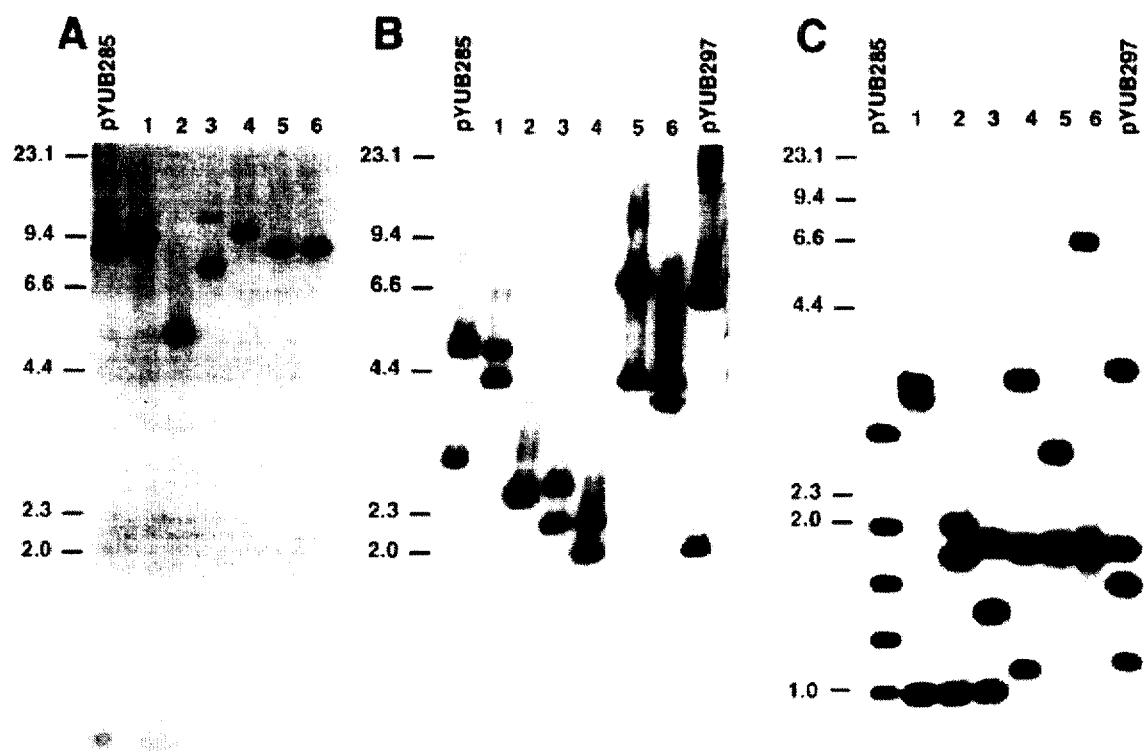
Figure 11A:
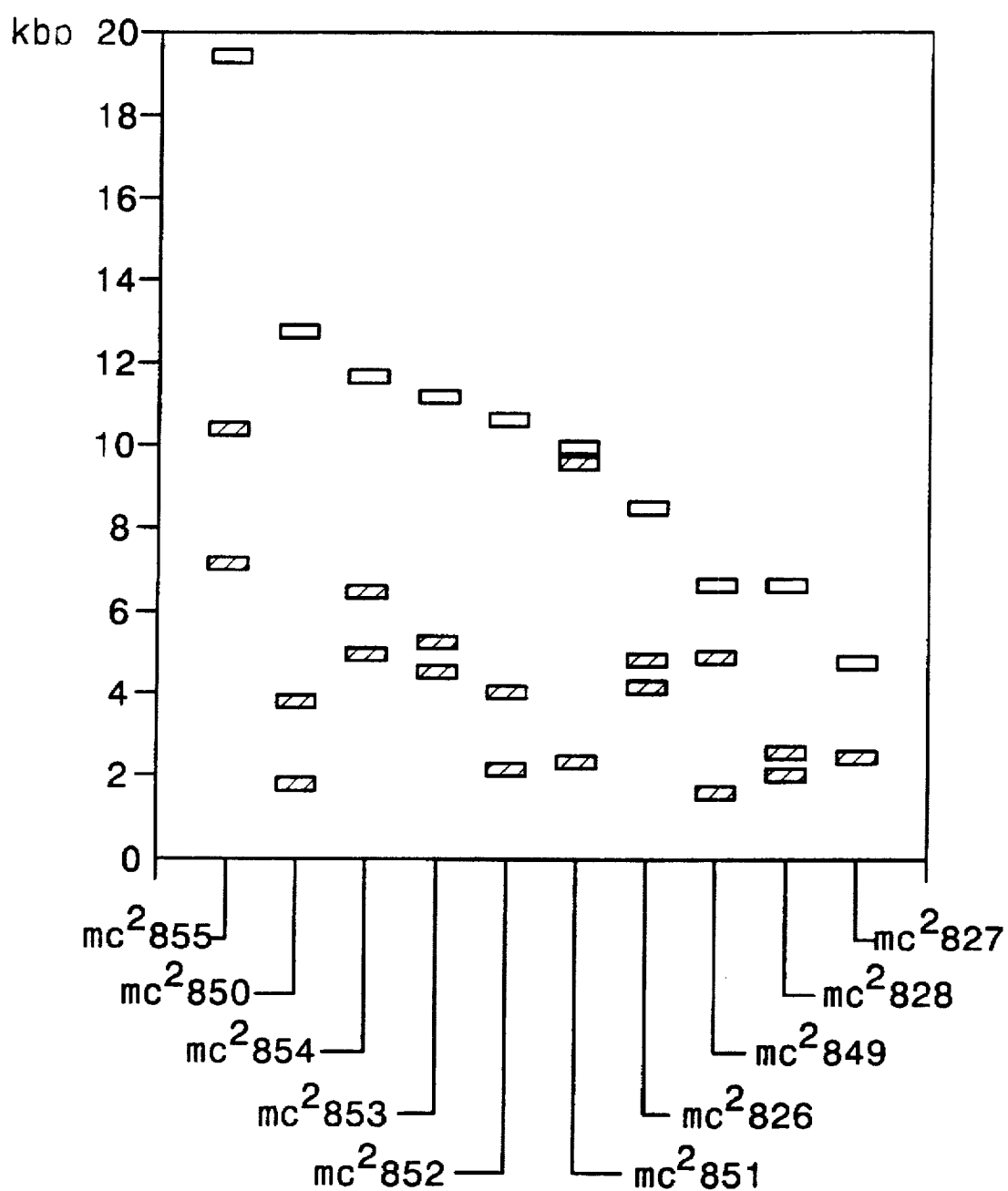
Figure 11B:
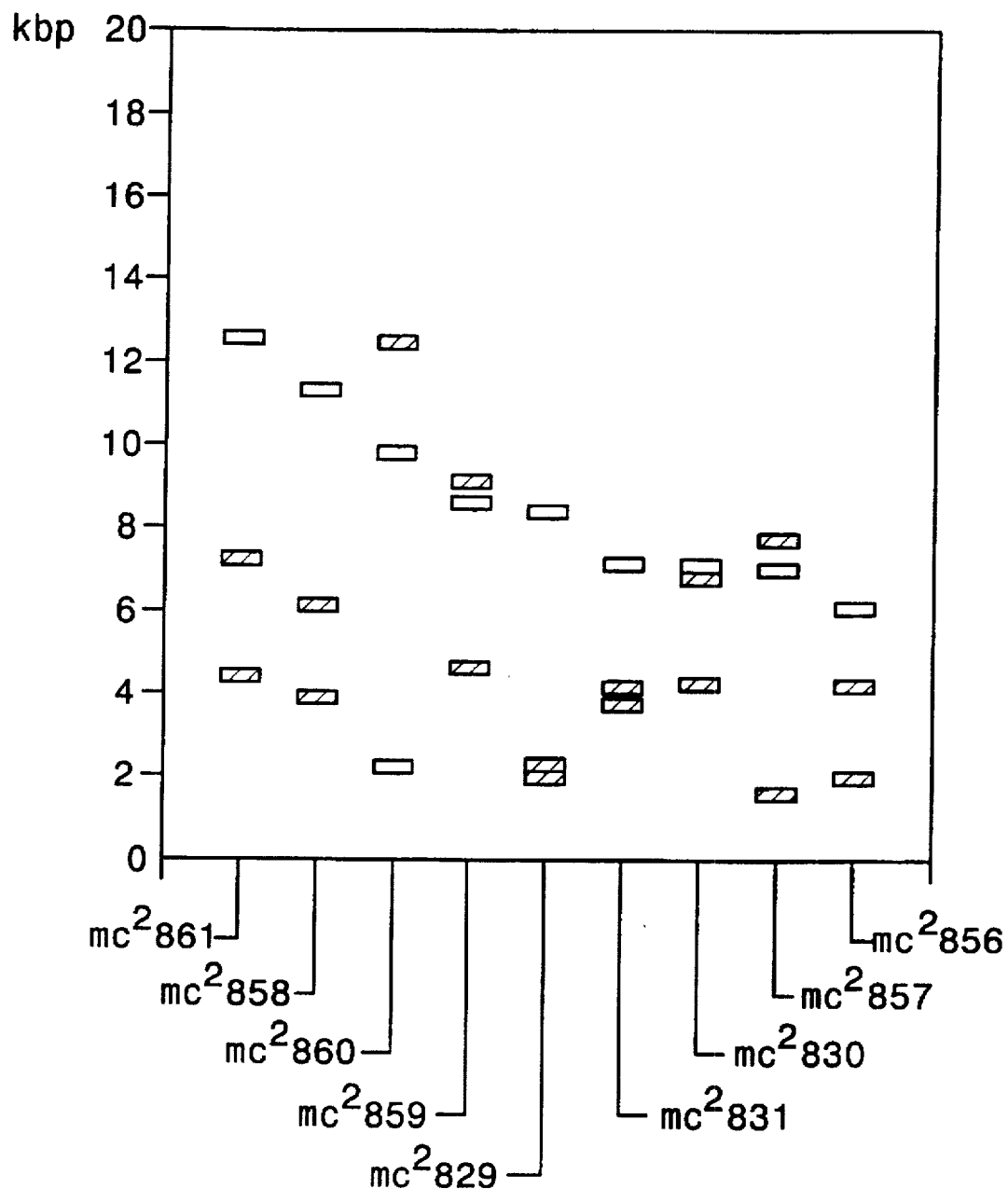
Figure 13:
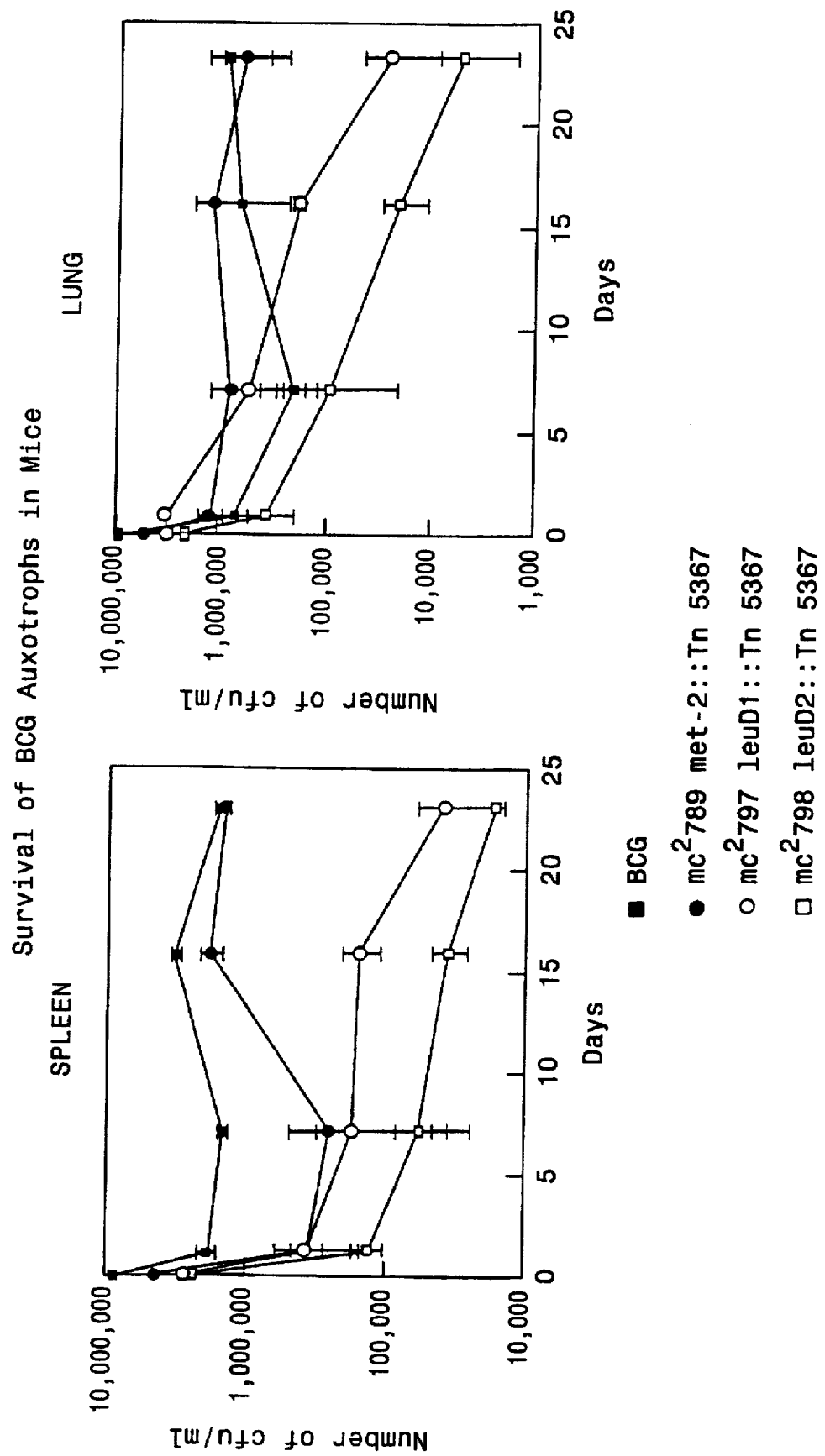
Figure 14:
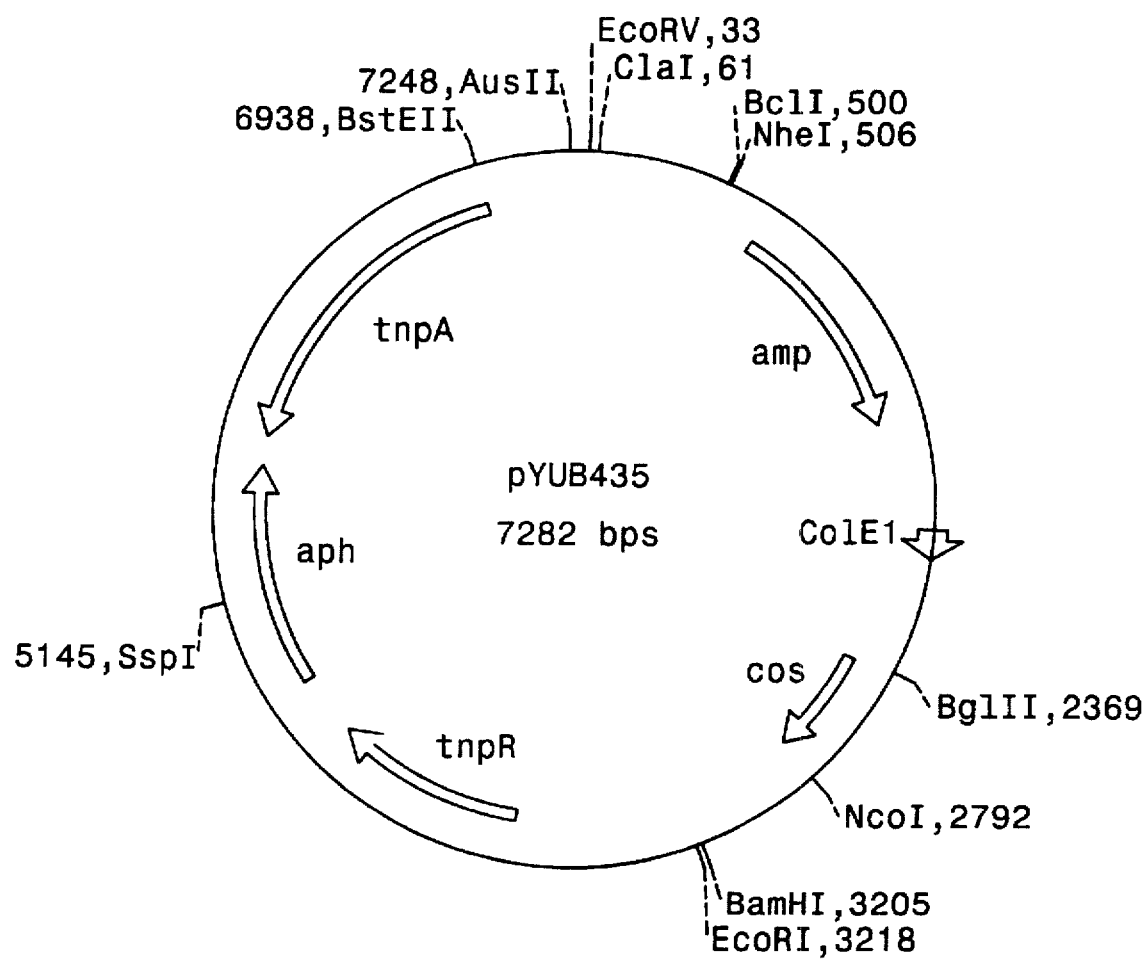
Figure 15:
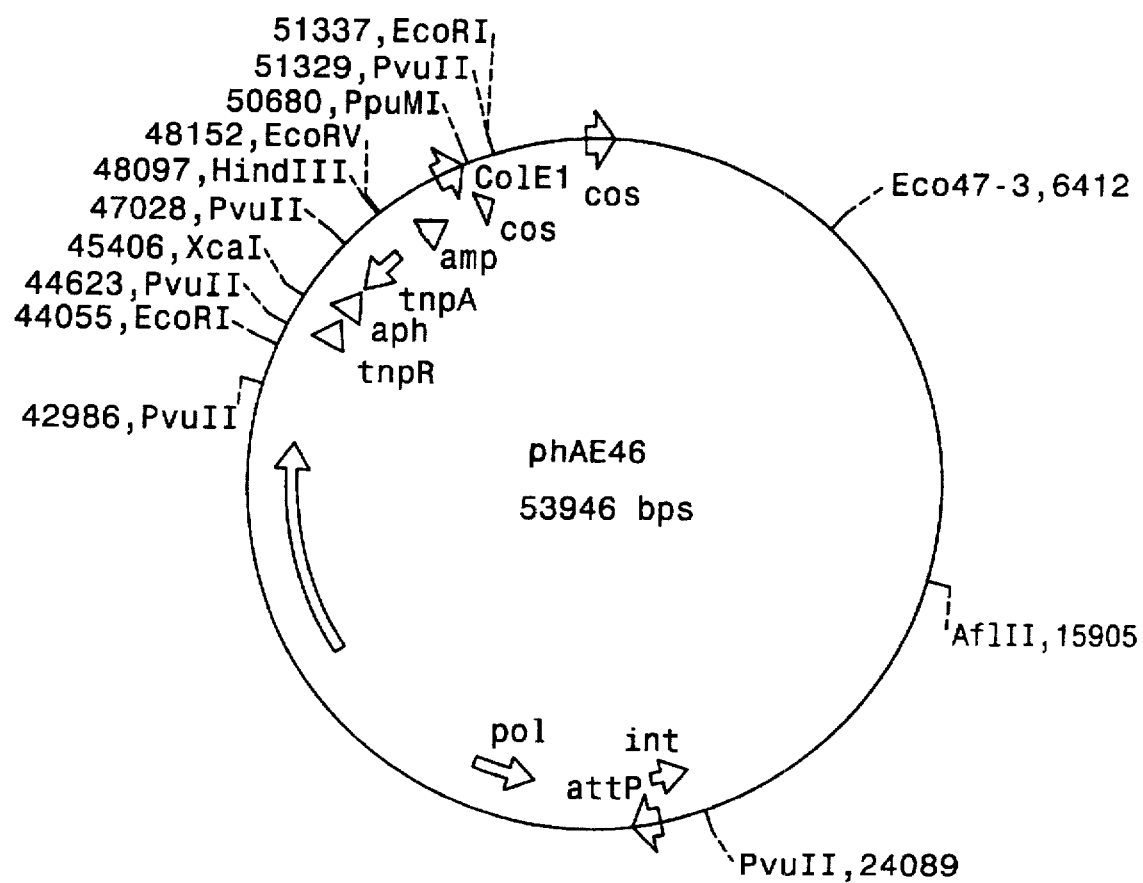

FIG. 8 represents the *M. smegmatis* insertion element IS1096 and transposons derived from it. The IS element has two major ORFs; ORFA and ORFR (marker by filled arrows), bounded by inverted repeats (IRs). Transposons were constructed by inserting an aph gene (shaded arrow), between the ORFs, into the MluI site (Tn5368), or into a SalI site within ORFR (TN5368); or in an NcoI site within ORFA (Tn5369). Relevant restriction sites are indicated;

FIG. 9 represents plasmid constructs used to assess transposon activity in *M. bovis* BCG. All plasmids contain an aph gene for kanamycin resistance, which constitutes part of the transposons in pYUB285, pYUB297 and pYUB305. They also have a disabled oriM (represented by a single arrow) which contains a 556 bp deletion, marked by a bar. pYUB312 contains the aph gene outside the IS element, so transformants will only be seen if integration of the plasmid has occurred;

FIG. 10 is comprised of FIGS. 10A, 10B and 10C, and represents Southern blots of six clones resulting from transposition with Tn5367 (1–3) and Tn5368 (4–6). Lane 1, mc$^2$826; 2, mc$^2$827, 3, mc$^3$838; 4, mc$^2$829; 5, mc$^2$830 and 6, mc$^2$831. M, pYUB285; s, pYUB297. DNA was digested with A: KpnI, B: BamHI and C: PvuI. Blots were probed with pYUB285 and mobilities are indicated by markers in kbp;

FIGS. 11A and 11B are graphical representations of the sizes of restriction fragments obtained from a total of nineteen BCG clones picked at random. FIG. 11A depicts the restriction fragments of those clones transformed with Tn5367-containing plasmid pYUB285. FIG. 11B depicts the restriction fragments of those clones transformed with Tn5368-containing plasmid pYUB297. The clones were digested with KpnI (black bars) or BamHI (hatched bars) and hybridized with pYUB285. They have been arranged in descending order according to the KpnI fragment size to show the randomness of transposition and allow comparison of clones having similar KpnI fragments but different restriction patterns with BamHI;

Figure 12:
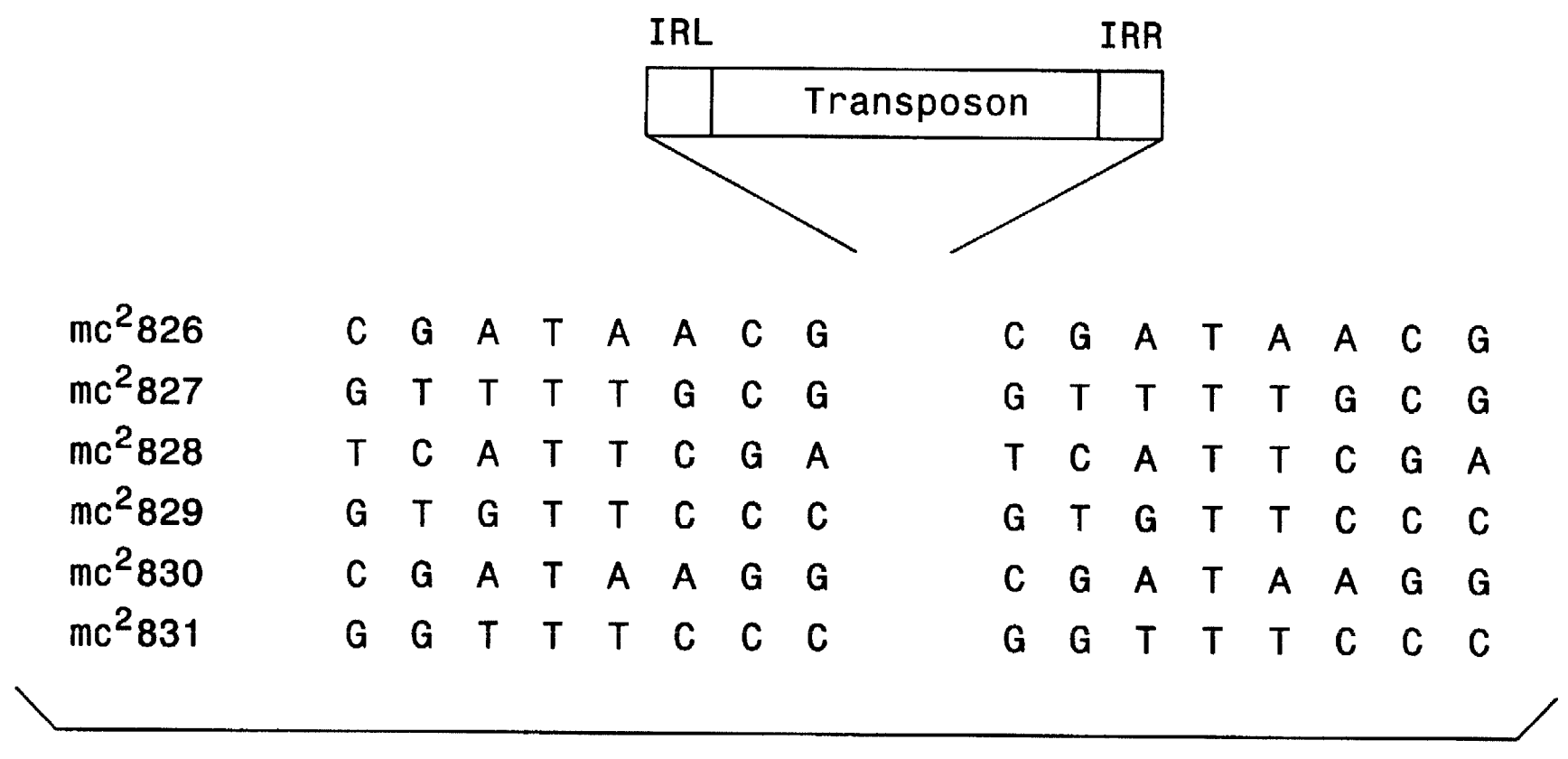

FIG. 12 represents a DNA sequence found on either side of the transposon in the six clones examined. An eight base-pair direct repeat is present in each clone, presumably from duplication of target DNA. mc$^2$826, mc$^2$827 and mc$^2$828 are clones containing Tn5367 and mc$^2$829, mc$^2$830 and mc$^2$831, contain Tn5368;

FIG. 13 represents the survival of transposon-derived auxotrophs of BCG in mice. Methionine auxotroph grows in a fashion similar to wild-type BCG as compared to the leucine auxotrophs, which are quickly lost from both the mouse spleen and lungs;

FIG. 14 represents a cosmid pYUB435 containing the IS1096 derived transposon TN5367; and FIG. 15 represents a transposon delivery shuttle phasmid phAE46 derived from phAE41 containing the cosmid pYUB435.

DETAILED DESCRIPTION OF THE INVENTION

This invention is directed to L5 shuttle phasmids capable of delivering foreign DNA into mycobacteria. The L5 shuttle phasmids are produced by inserting a cosmid into a nonessential region of an L5 mycobacteriophage genome. In addition, other foreign DNA can be inserted into the L5 shuttle phasmid, including reporter genes (such as a luciferase gene), a transposon (such as IS1096), and a gene which encodes a mycobacterial inhibitor (such as anti-sense RNA which has a target of a mycobacterial gene necessary for mycobacterial survival). Further, a DNA-modifying enzyme, and RNA-modifying enzyme or a protein-modifying enzyme can be inserted into the L5 shuttle phasmids of the invention for subsequent insertion into mycobacteria, including *M. tuberculosis*, *M. smegmatis*, BCG and *M. bovis*.

Once L5 shuttle phasmids are obtained, they can be utilized to generate mycobacterial mutations. These mutations can be used to study the mechanisms of mycobacteria as well as to develop vaccines and drugs effective in the treatment of mycobacteria.

In order to generate mycobacterial mutations, L5 shuttle phasmids are produced by inserting a cosmid, such as an *E. coli* bacteriophage lambda cosmid, and a transposon, such as IS1096, into the genome of an L5 mycobacteriophage. Once the cosmid and transposon are inserted into the L5 mycobacteriophage, an L5 shuttle phasmid is created and is then propagated in a conditional host. The propagated L5 shuttle phasmids are infected into mycobacteria so as to cause delivery of the transposons from the L5 shuttle phasmids to the chromosomes of the mycobacteria, thereby causing mutations in the genes of the mycobacteria to occur. A mycobacterial mutation library is thereby obtained.

In order to produce mycobacterial vaccines, the mycobacterial mutation library is utilized. The presence of a marker gene in the transposons is selected for. This identifies mycobacterial mutants in which the transposons have been delivered into the mycobacteria. Screening is then performed in order to identify a mutation of interest. For example, screening can be performed for an avirulent mutant. Avirulent mutants and other mutants can then be used as mycobacterial vaccines. Examples of marker genes which can be selected for are kanamycin resistance genes, hydromycin resistance genes and L5 immunity genes. An example of an avirulent mutant which can be screened for is a leucine auxotroph.

Further, this invention is directed to a method of determining whether an L5 mycobacteriophage gene is essential for L5 propagation. In order to perform this, a mutation of an L5 gene is generated utilizing a cosmid form of an L5 shuttle phasmid and recombinant DNA technology so as to obtain an L5 shuttle phasmid mutant. The mutant is then propagated and transfected into *M. smegmatis* in order to determine whether plaques have formed. If plaques have formed, this indicates that the L5 gene is not essential for L5 propagation. If no plaques have formed, this indicates that the L5 gene is essential for L5 propagation. The construction of several L5 shuttle phasmids of the invention is described below.

EXAMPLE 1
Construction of L5 Shuttle Phasmids

Figure 1:
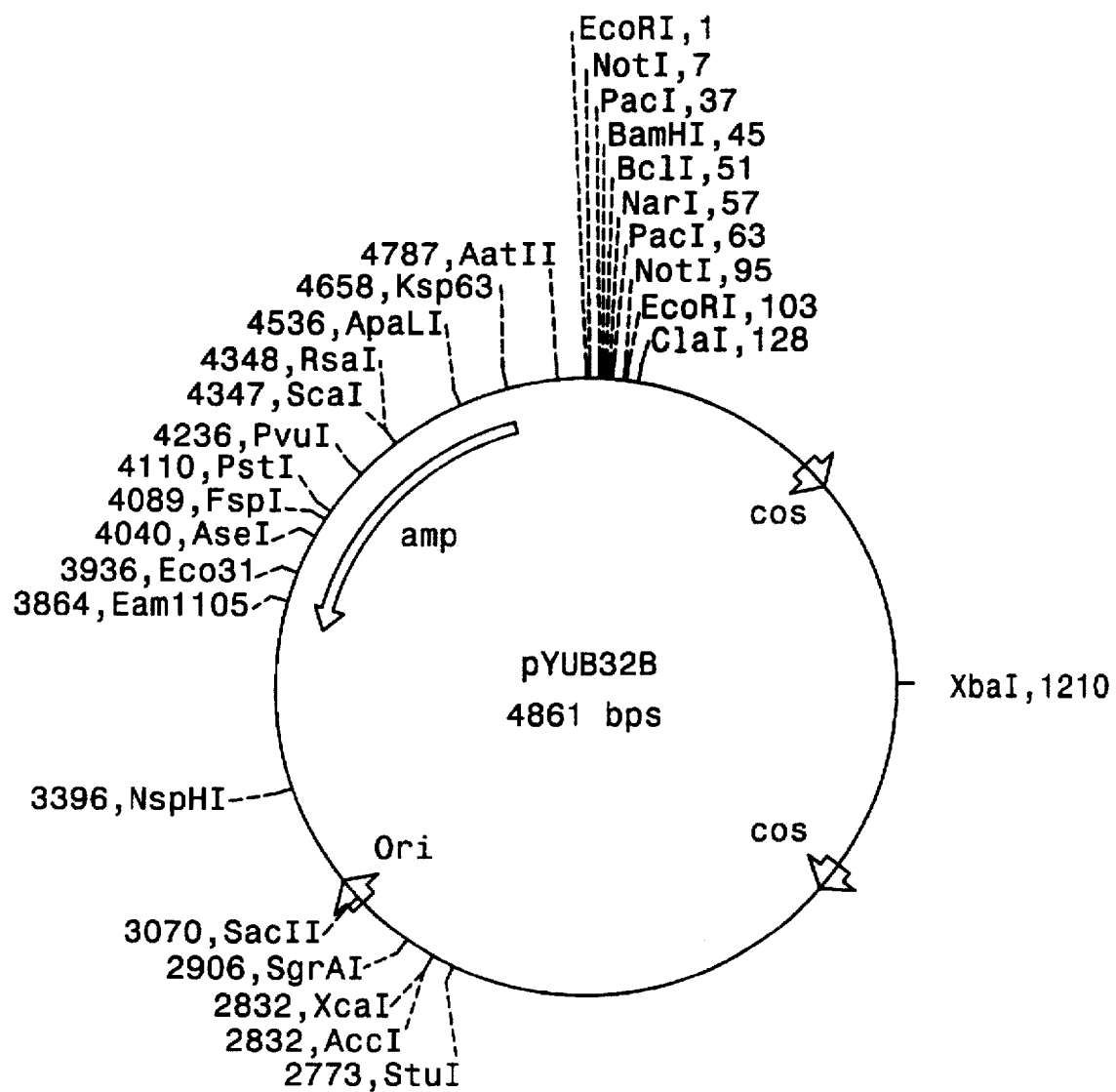
Figure 2:
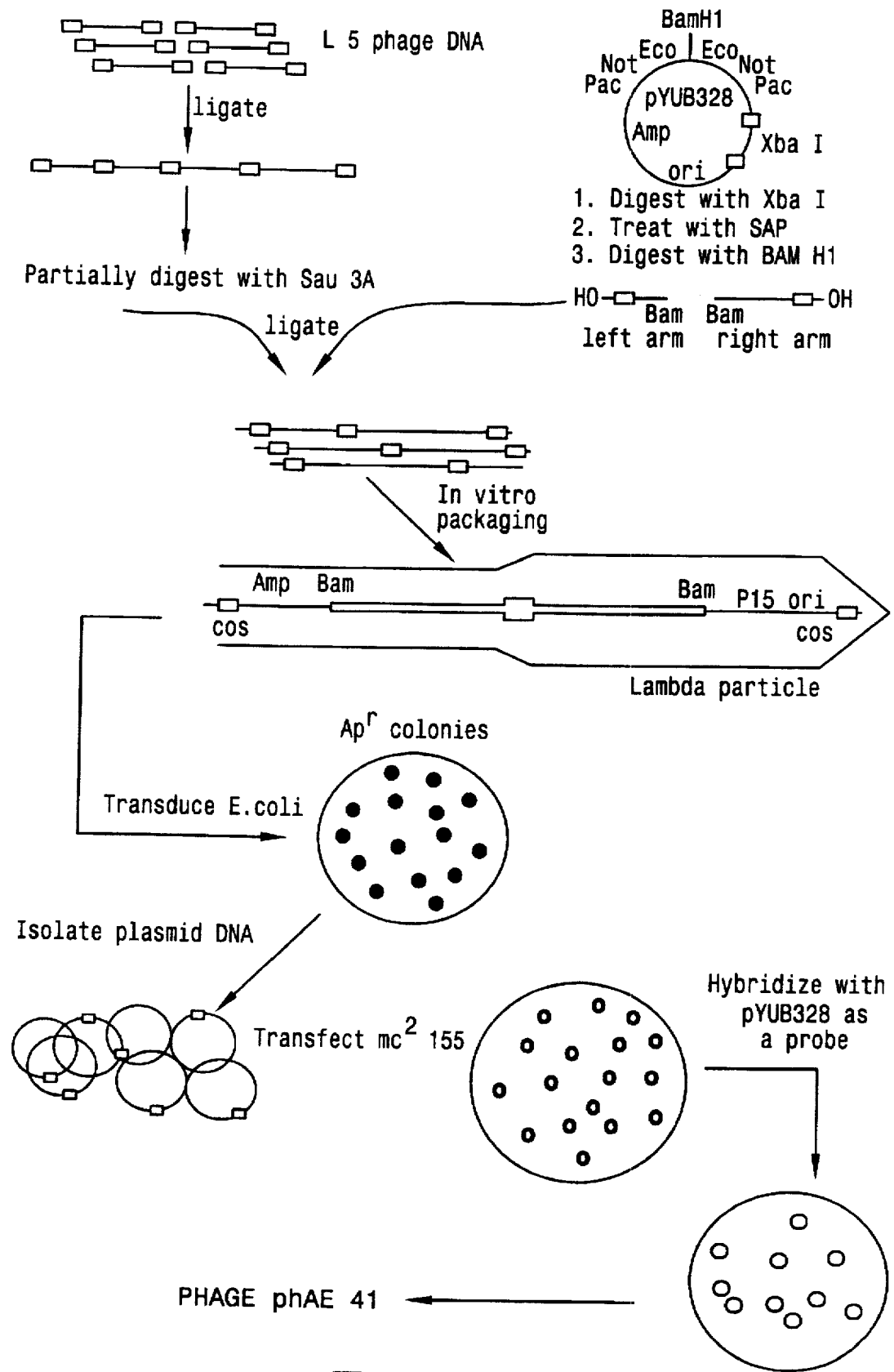

In order to construct an L5 shuttle phasmid, an *E. coli* cosmid pYUB328 (see FIG. 1) was inserted into a non-essential region of the L5 mycobacteriophage genome (see FIG. 3) by the method described by. Jacobs, et al., *Nature*, Vol. 327, pp.532–536 (1987). Cosmid pYUB328 was deposited with the American Type Culture Collection, Rockville, Md., on May 20, 1994 and catalogued as ATCC No. 69631. FIG. 2 represents a schematic diagram of L5 shuttle phasmid construction in accordance with the present invention. This generated a cosmid library of partially-digested mycobacteriophage genomes which replicated in *E. coli* as recombinant plasmids. Individual mycobacteriophage-cosmid clones were analyzed and it was determined that construction of the library had generated a set of cosmid-insertions at random sites around the L5 mycobacteriophage genome, which is typically accompanied by the generation of a small deletion of the mycobacteriophage genome at the site of insertion. This library was transfected into *M. smegmatis* cells and resulted in the identification of recombinant mycobacteriophages which have the *E. coli* cosmid inserted at non-essential regions of the L5 mycobacteriophage.

Previously constructed shuttle phasmids, for example the L1 shuttle phasmid constructed by Snapper et al., *Proc. Natl. Acad. Sci. USA*, Vol. 85, pp. 6987–6991 (1988), have not been as useful for insertion of foreign DNA into mycobacteria as they have contained deletions of the cosmid. The inventors concluded that these deletions likely indicate that mycobacteriophage L5 has rigorous packaging constraints, and therefore used a smaller, double-cos, cosmid, pYUB328, which was constructed by Balasubramanian, et al., (1994). This yielded a 3.8 kb cosmid following in vitro packaging into lambda heads.

A library of over 5000 Ap$^r$ (ampicillin-resistant) pYUB328::L5 recombinant clones was generated. Cosmid DNA isolated from *E. coli* was transfected into *M. smegmatis* in order to propagate it. Transfection of plasmid DNA of the library isolated from *E. coli* into *M. smegmatis* cells yielded 34 plaques. Eleven of these plaques were found to hybridize to pYUB328. DNA was prepared from mycobacteriophage particles and analyzed by restriction analysis. Five different classes of pYUB328 insertions into L5 were generated, which represented different size deletions of the genome. All of the L5 shuttle phasmids contained pYUB328 inserted near the immunity gene of mycobacteriophage L5. One of the shuttle phasmids was designated phAE41 by the inventors (see FIG. 4). L5 shuttle phasmid phAE41 was deposited with the American Type Culture Collection, Rockville, Md. on May 20, 1994, and catalogued as ATCC No. 69624.

EXAMPLE 2
Molecular Characterization of L5 Shuttle Phasmid phAE41

Figure 4:
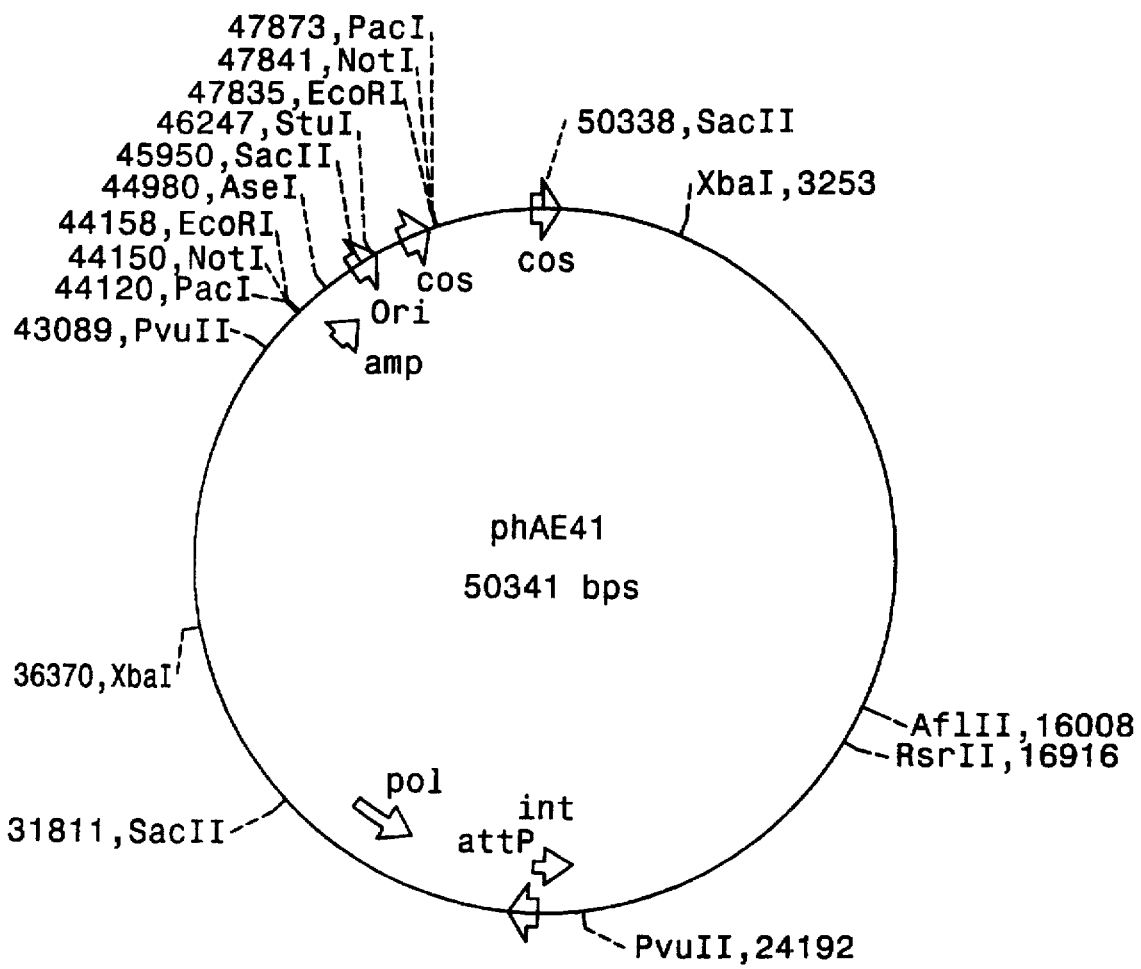
FIG. 4 represents a schematic diagram of the L5 shuttle phasmid phAE41 in which the cosmid pYUB328 was inserted into the immunity region of mycobacteriophage L5.

Experiments were performed to confirm that phAE41 was a shuttle phasmid constructed from mycobacteriophage L5. DNA isolated from mycobacteriophage particles of phAE41 was ligated together to yield long concatamers and then packaged in vitro into bacteriophage lambda heads. The resulting bacteriophage-packaged particles were capable of transducing ampicillin-resistance at high frequencies. This was determined by mixing the in vitro packaged lysate with α-sensitive *E. coli* cells and then plating on agar containing 5 μg/ml ampicillin. The phAE41 yielded $10^4$ ampicillin-resistant colonies. Comparisons of restriction analyses of plasmids isolated from *E. coli* and phage-digested molecules demonstrated identical patterns except for the unligated cohesive ends of the linear phage molecules. These results demonstrated that the phAE41 molecules were stable in both mycobacteria and *E. coli*. However, unlike the phAE15 shuttle phasmid derived from L1 (Snapper, et al., 1987), the entire cosmid in the L5 shuttle phasmid was stably maintained in shuttle phasmid phAE41. In addition, the *E. coli* cosmid portion of the shuttle phasmid could be completely removed from the phAE41 with any of three enzymes, PacI, NotI or EcoR1. Restriction analyses was used to determine the site of insertion of the pYUB328 cosmid, and thus the complete sequence of the phAE41 was deduced. The map of phAE41 is shown in FIG. 4. The sequence for phAE41 is shown below:

| SEQ ID NO: 1 | | | | | |
|---|---|---|---|---|---|
| 1 GGCGCTCTCG | CATCGCATCG | AGTGTTTGCT | GTGTCTCTCA | TCGTCGCAGG | TCAGAAGGGG |
| 61 TAGGGGGGTT | CCCCCTAGGG | GTCGGTCCTT | GACCGGTCGG | TTAGGTCGGT | TATGCGGCCG |
| 121 AGCCATCCTG | TACGGGTTTC | CAAGTCGATC | AGAGGTAGGG | GCCGGCACAG | AAACCACTCA |
| 181 CATCAGGGCT | GTGCGCCTCC | AGGGCGCGTG | AACTCCCACA | CCCCGGTGTA | GTTACATCCC |
| 241 GGAATTGTCT | CAGCGCCTCT | CAGGGCGCTT | CTCATAAACA | GTGATCTACG | CCACTCCTGA |
| 301 CGGGTGGCTG | TCAAGGATAC | TCACCTTCCC | TACTAATGAG | GGGCTAAGAG | CCCCTCTCTA |
| 361 TAGAGCGCCG | CACAGGCGGC | GCGATAAGAG | CGCCACCAGG | CGCTCATCTA | AAGACCGGCC |
| 421 TTGAAGGGCC | GGTCATAGAG | ATCTATTCGA | TCCGGCAACC | GCCGGATCTC | AAGGCCGCGC |
| 481 CAGTGCGCGG | CCCTATAGAG | GGGTGACTCA | ACTGTGCATG | GCACTCGCTC | GAGTGCCCAC |
| 541 TGGAGCACTC | AACCGGGGAA | GTTCGACGTT | CTCAACCTGC | GAATGACGTT | TGAATCGTCA |
| 601 TCCGCGTACG | AAATCCCCGA | TCTGCGGCCG | ACCGACTTCG | TGCCGGCCTA | TCTCGCGGCC |
| 661 TGGAATATGC | CGCGTCACCG | CGATTACGCC | GCCAAGAACG | GCGGCGCGCT | GCACTTCTTC |
| 721 CTTGACGATT | ACCGGTTTGA | GACCGGTGG | TCGTCCCCCG | AGCGCCTTCT | CGACCGCGTA |
| 781 AAGCAGGTCG | GCGCTGCACT | CACGCCGGAT | TTCAGCCTCT | GGACGAACAT | GCCGAAGGCG |
| 841 GCGCAGCTAT | GGAACGTCTA | CCGCTCCCGC | TGGTGTGGCG | CGTATTGGCA | GTCGGAAGGA |
| 901 ATCGAGGTGA | TTCCGACGGC | GTGTTGGGCG | ACTCCCGACA | CGTTCGATTT | CTGTTTCGAC |
| 961 GGGATCCCGA | TGGGATCGAC | CGTCGCAATT | TCTTCGATGG | GCATTCGCTC | TTCAAAAGTC |
| 1021 GACCAGGAGC | TTTTCCGGTA | CGGACTACGC | GAACTCATCG | ATCGCACTCA | ACCGCAACTG |
| 1081 CTTTTGGCAT | ATGGCCAGCT | TCGGCATTGC | GACGACATGG | ATTTACCAGA | GGTCCGCGAA |
| 1141 TACCCGACCT | ACTGGGACAG | ACGACGAAAG | TGGGTAACTG | CCGATGGGAG | GCCGGGGAAG |
| 1201 TAAAGGCGGC | CCCGGTCCCG | GAACCGGAGC | ACGCAACCGC | AGAGGCGCTG | GAGCCCCCGG |
| 1261 ATCGGGCGGC | GTAGGCGGCG | TCGCAGGGCG | GGGTGGAGCT | GCAGGGAGCA | GCGGAGGCGG |
| 1321 CAAGGGAACG | GCAGCGCCGG | TACCGGAGGC | GTCACCGGTG | GCGGCGGAAG | TGGAGCCGGC |
| 1381 GGCGGTGGCA | GCAGCCCCAA | CACCCCGGTG | CCCCCCACCG | AGCTGGAGAA | GAAGCGCGGC |
| 1441 GAATACAACC | AGATCGCCAT | CGACGCCCAG | AAACAGCACG | CGCCCACCGA | TGAGAAGCGC |
| 1501 GAGGCCAAGC | GCAAGCAACT | GATGGATCGA | GTCGGAGGAG | ACTGGCAGGC | TTTGGACCCG |
| 1561 GATCACCACG | ACGCCATCAA | GGTGGCGATG | GATGACGCCA | TGCGGAAGAT | CCTCTCCGAG |

SEQ ID NO: 1

```
1621  GAGGAGATCG  TCCACCGCAC  CAAGCACTTC  GGCGACCTAC  TCGACTCCGG  TCGACTCAAG
1681  TCGCTGTTCG  AGGTCGGCTT  CTCAGCCGGT  GGCGACACCC  CGACCGAACG  CGCCCTCCTC
1741  GAGGACGACT  GGTTCGGCGC  AGGCAAGGTT  CCCCCGATCT  ACTCGGCAAT  CGAGTTCAAC
1801  GGCGCTCCGA  CAGCCGGCCT  CGGCATGTAC  GGCGGCACCA  AGCTCTACAT  GAAGGACTCG
1861  GTCAAGGACC  GCGTCACCGT  GACCATCGGC  GACTCGCTGA  TGTCGAGCTG  GGACGTATTC
1921  CCCGGCCGTC  CTGGCGACGG  CGTGGGGCTG  TGGGCCAGCC  TGTCGAAGAT  CGAGGGGCTG
1981  GTCGATCCGA  GCAAGACCCG  CGAAGAGAAC  ATGCAGGCGG  TCTACGACTC  GTTCAAGAAG
2041  TACGGCACCC  TGGACGGCTT  CATCGAGGCG  CAGATCCACG  GCGGCGTCCT  GGTCGAGGAC
2101  ATCAAGAAGG  TCGTGTTCAC  GCAGCCGCCG  AGCCCGATCT  TCACCGATAA  ACTGGACGAA
2161  CTTGGAATCC  CGTGGGAGGT  GCAGTAATGG  CGCAGATGCA  GGCGACACAC  ACAATCGAGG
2221  GGTTCCTGGC  TGTCGAGGTG  GCCCCTCGGG  CGTTCGTCGC  AGAGAACGGC  CACGTACTGA
2281  CCCGGCTGTC  GGCCACGAAG  TGGGGCGGTG  GCGAGGGTCT  CGAGATCCTC  AACTACGAGG
2341  GTCCAGGGAC  CGTCGAGGTC  TCCGACGAGA  AGCTCGCCGA  AGCCCAGCGG  GCCAGCGAGG
2401  TCGAGGCTGA  ACTTCGCCGC  GAGGTCGGCA  AGGAGTGAGC  TGGGCCGGCT  CAGGCCGGCG
2461  ACAGGAACTA  CCAGAGGACT  GGGAGCTGAA  TTACCGGCTC  CCGGTCCTTT  CTGCTGCCAA
2521  CTGGCTTTGC  CAGATCAACG  GTCCCGGATG  CGTAAGGGCC  GCAACCGATG  TCGACCACAT
2581  CAAGCGCGGG  AACGACCACA  GCCGGTCCAA  TCTGCAGGCA  GCCTGCCATG  TCTGTCACGG
2641  CAAGAAATCA  GCCGCCGAGG  GCGTAGCCCG  ACGGCGGGAA  CTTAGAGCCC  GGAGGAAGCG
2701  ACCACCCGAA  CGCCATCCTG  GGCGTCGATA  AGCGGGCCAG  GTGCCCGCTC  CACCCAGGAG
2761  GTGAACAGTG  GGCACGCGAG  GCCCAATCGG  AAAACGAGAT  GAAGAGCGGG  TTCGTCGGAA
2821  CACCCCGGAC  AGTCCAACCG  ACACGATCCA  GATGCCCGGT  CTGGTGACGA  TCCCCGAGAT
2881  GGGCGATCTA  AGCCACGACG  GCCGCACGCA  CCAGCTCGTC  AAGGACATGT  ACGAGTCGAT
2941  CAAGCAGTCG  GCAGCCGTGA  AGTACTACGA  GCCGACCGAC  TGGCAGATGG  CCCGACTCGC
3001  CCTCTACACA  CTTAACCAGG  AACTCATCGC  AGCCGAAGAC  AACGGCAAGC  CCGTGGGCGC
3061  GATGAAGCTC  ACTGCCATCA  ACCAGATGCT  CTCCGCGCTG  CTGCTGACCG  AAGGTGACCG
3121  ACGCCGCGTC  CGACTCGAAG  TCGAACGAGC  ACCCGCTGAC  CCGACAGGCG  GGAAGGTCGT
3181  TGACGTGACC  GACGTGCTCA  AGCAGCGCCT  CGCCAAGGCG  AGCGGCGGGA  GCTGATGGTC
3241  CCCCGAGGGG  TTTCTAGAGC  CGCTGCCGCT  ACCAGCGCCT  CCCCCTCGGG  GTAGACATCG
3301  AAAGGAACCA  CATGGCCGAC  CTCGGCAACC  CACTCGACCT  CGAGATGCTC  TGCCTGGTCA
3361  CAGGCCGGGA  CTTCCGCTGG  ACCATCGATT  ACCCGTGGGG  TCCGGGAGAG  CTGTTCCTCG
3421  AACTCGAGAC  CGGCGGCGAA  CACAACGCGC  TGCATCAGGT  CTATGTCACC  GGGGCGACCG
3481  GAGGCACGTA  CACGCTGAAC  GTCAACGGCA  CCAACGACCA  GGCCATCGAC  TACAACGACG
3541  TGTCGGAGAA  TCCGCAGGGG  CTGGCAGGCG  ACATCCAAGA  CGCTCTGGAC  GCAGCCGTCG
3601  GAGCCGGAAA  CGCTGTCGTG  CATCCGGTCT  CGCTGTTCCC  TGCGTGGACA  CTGAACTTCA
3661  ACCTCAACGC  CAGCAAGCCG  CTCACCGAGC  AGTTGGTCAA  CACGATCAAC  AAGGCCGCGA
3721  ACGACTTCTT  CGACACGTTC  GACCAACTAC  TTGGGGTCGA  CGTGGAGATG  ACGGTCACCG
3781  ACACCCTGAA  CTTCAAGCTC  AAGGTGACCT  CGCGGCGCTC  GTTCGATGAG  GTCGGTGTCG
3841  TCACGTTCGC  GGTCGACGTG  ACCAGCCAGG  CAGTCATCAA  CTTCTTCAAC  TCCGTCGCCG
3901  AACTCACCGG  AGCGGTGAAC  ACCGTCAACG  TCGACTTCTA  CTGGAACCGG  ACGTATGACA
3961  TCGAGTTCAC  CGGATCCCTT  GGGCTGCAGC  CGATTCCGAC  TACTACAGCC  GACATCACCA
4021  ACCTGGCGGG  TACCAGCAAG  GCCGTCTCAG  TCACGGTGGT  CGAGCCAGGA  AAGAAGAGGC
4081  TGACCATCTG  GCCGTTCACG  GTCAACGGTG  AAAACCGCAAC  CATCAAGGTC  GAGTCCGAAG
4141  AGGCCGACAA  GATCCCCAAC  CGCTGCCGCT  GGCAGTTGGT  TCACATGCCG  ACCGGCGAGG
4201  CAGCCGCCGG  CGATGCAAAG  CAGCTCGGCC  GCGTTTACCG  ACAGCCGAGG  TAACACCGCA
4261  CCCATCAGAG  ATGGTGGGCC  AGACGGCCTT  CGGGCCGTCC  CCTGACGTGT  AGCTCAATGG
4321  CAGAGCGCCC  GACTGTTAAT  CGGGTGGTTG  AAGGTTCGAG  TCCTTCCATG  TCAGCGAGGG
4381  CTGAACCGGA  CCCGTGTCCG  GTGTAGGCAC  TTTCCGCAGG  CGGTTCCCCA  GAGCGTGGGG
4441  AGCCCCTGCC  CTGTACACGT  AGCTCAATTG  GTAGAGCAC  GGTCTCCAAA  GCCGCCGGTT
4501  CCAGGTTCGA  CTCCTGGCGT  GTATGCACAC  ACCCCTGACT  CCTGCTAGCG  GAGTGTTCGC
4561  CTTTCGGGCC  TGGGGTCTTT  TTCCCCGTTC  GTCTAATCGG  TAAGACACCC  GGCTCTGGAC
4621  CGGGCAATTG  AGGTTCGAGT  CCTTGGCGGG  GAGCCAACTT  GACATCCACC  CGAAAGGAAC
4681  AACATGACCT  TCACAGTCAC  CCGCGAGAGA  GCGCAGTGGG  TCCACGACAT  GGCCCGCGCT
4741  CGCGACGGTC  TCCCCTACGC  GTACGGCGGG  GCGTTCACCA  ACAACCCGAG  GGTGTCGACT
4801  GACTGCTCTG  GCCTGGTGCT  GCAGACCGGG  GCTTGGTATG  GAGGTCGCAC  CGACTGGGTC
4861  GGAAACCGTT  ACGGCTCAAC  CGAATCGTTC  CGGCTCGACC  ACAAGATCGT  CTACGACCTA
4921  GGGTTCAAGC  GGATGCCCCG  AGGCGGGCCA  GCGGCCTTGC  CGATCAAGCC  GGTGATGCTC
4981  GTCGGGCTCC  AGCACGGAGG  CGGCGGGGTC  TACTCGACA  CCGCTTGCAC  GTTGATGACG
5041  ATGGACCACC  CCGGTGGCCC  GGTCAAGATG  TCCGACCGAG  GCGTCGACTG  GGAGTCCCAC
5101  GGCAACCGCA  ACGGCGTAGG  CGTCGAACTT  TACGAGGGCG  CACGGGCATG  GAACGACCCT
5161  CTGTTCCATG  ACTTTTGGTA  CCTGGACGCA  GTCCTCGAAG  ACGAAGGAGA  CGATGACGAA
5221  TTGGCTGACC  CAGTTCTAGG  GAAGATGATC  CGCGAGATCC  ACGCGTGCCT  GTTCAATCAG
5281  ACCGCGTCGA  CCAGCGATCT  GGCGACCCCT  GGTGAAGGCG  CTATCTGGCA  GCTACACCAG
5341  AAGATCCACT  CGATTGACGG  CATGCTCCAC  CCGATCCACG  CTGAGCGGCG  CGCTCGCGCA
5401  GGCGATCTCG  GTGAGCTGCA  CCGAATCGTG  TTGGCCGCGA  AGGGCTTGGG  CGTGAAGCGC
5461  GACGAGGTGA  CCAAGCGGGT  CTACCAGAGC  ATCCTCGCCG  ACATCGAGCG  GGACAACCCC
5521  GAAGTACTTC  AGCGATACAT  CGCAGAAAGA  GGTGGCCTAT  GAGCCCCAAG  ATCCGACAGA
5581  CCATCTACCT  GCTCGGCACC  GCCGCCCCGG  CACTGCTGGG  CATCGTCCTG  ATCTGGGGCG
5641  GGCTCGACGC  TGAGTCGGCG  GCTGACCTCG  GTGACATCAT  TGCGGGCGTC  GTGTCGGATAC
5701  TAGTCTCCGG  TGCGCCGGCC  GTAGCGGCAG  GCACCGTACG  CAGCCAGCCG  AAGGACGGCA
5761  CGTTGTCCAC  CAGCCCGGTG  GATCAGGTCA  CCAAGGGCGT  CGAGCAGGTG  CTCGCGGCCA
5821  GGCAGAGTGC  CGAGGCTGAA  GTCGCGAAGG  TCAAGCAGGC  GCTGGAGACC  GCCGTCAGCG
5881  GTTCTCTCCC  CCAGCTCGGC  CCGCTGGCCA  CGCAGATCCT  CAACGTGGCT  GACGCACCG
5941  TCTGGCGTCC  ATGAGCAAGC  CCTGGCTGTT  CACCGTCCAC  GGCACAGGCC  AGCCCGACCC
6001  GCTCGGGCCT  GGTCTGCCTG  CCGATACCGC  ACGGGACGTA  CTTGACATCT  ACCGGTGGCA
6061  GCCCATCGGC  AACTACCCGG  CAGCGGCGTT  CCCGATGTGG  CCGTCGGTCG  AAAAGGGTGT
6121  CGCTGAGCTG  ATCCTGCAGA  TCGAGCTGAA  GCTGGACGCA  GATCCGTACG  CGGACTTCGC
6181  GCTGGCCGGC  TACTCGCAGG  GAGCCATCGT  GGTGGGCCAG  GTGCTCAAGC  ACCACATCAT
6241  CAACCCGAGA  GGTCGACTGC  ACCGGTTCCT  GCACCGGCTC  AGGAAGGTCA  TCTTCTGGGG
```

-continued

SEQ ID NO: 1

| | | | | | |
|---|---|---|---|---|---|
| 6301 | TAATCCGATG | CGGCAGAAGG | GCTTTGCCCA | CACCGACGAG | TGGATTCACC | AGGTCGCTGC |
| 6361 | CTCGGACACG | ATGGGCATCC | TCGAGGACCG | ACTGGAGAAC | CTCGAGCAGT | ACGGCTTTGA |
| 6421 | GGTCCGCGAC | TACGCGCACG | ACGGCGACAT | GTACGCCTCC | ATCAAGGAGG | ACGACATGCA |
| 6481 | CGAGTACGAG | GTGGCCATTG | GCCGAATCGT | GATGAGCGCT | AGGCGATTCA | TCGGAGGTAA |
| 6541 | GGACTCCGTC | ATCGCCCAGC | TCATCGAGCT | TGGACAGCGT | CCGATCTGGG | AGGGAATCGC |
| 6601 | GATGGCCAGA | GCCATCATCG | ACGCCCTCAC | GTTCTTCGCC | AAGTCGACCC | AAGGCCCGAG |
| 6661 | CTGGCCGCAT | TTGTACAACC | GCTTCCCGGC | GGTCGAGTTC | CTACGACGAA | TCTGAGAAAG |
| 6721 | GAGGCGGGGT | GAGCCTCAAC | AACCACCACC | CGGAGCTTGC | CCCGTCTCCC | CCTCACATCA |
| 6781 | TCGGCCCGTC | CTGGCAGAAG | ACGGTCGATG | GTGAGTGGTA | TCTGCCTGAG | AAGACCCTCG |
| 6841 | GCTGGGGAGT | CCTGAAGTGG | CTCTCCGAGT | ACGTGAATAC | CCCTGGCGGG | CATGACGATC |
| 6901 | CGAACCGTCT | GGCGACGTTG | ATCGCGCTCT | CCGAGGCAGG | TCTTCTCGAC | AACGAGAACA |
| 6961 | TGTTCATCCC | CACCGACGAG | CAGGTACGCC | TGGTCCTCTG | GTGGTACGCA | GTAGATGACC |
| 7021 | AGGGCCAGTA | CATCTACCGC | GAGGGCGTGA | TCCGCCGGCT | CAAGGGCTGG | GGCAAGGATC |
| 7081 | CGTTCACCGC | CGCGCTCTGC | TTGGCGGAAC | TCTGTGGCCC | CGTAGCCTTT | TCACACTTCG |
| 7141 | ACGCCGACGG | TAACCCGGTC | GGCAAGCCGC | GTTCAGCCGC | GTGGATCACC | GTCGCGGCCG |
| 7201 | TCAGCCAGGA | CCAGACGAAG | AACACGTTCT | CGCTGTTCCC | GGTGATGATC | AGCAAGAAGC |
| 7261 | TGAAGGCCGA | GTACGGCCTG | GACGTGAACC | GCTTCATCAT | CTACTCCGCA | GCCGGTGGCC |
| 7321 | GTATTGAGGC | AGCGACCTCG | AGCCCCGCGT | CGATGGAGGG | TAACCGCCCG | ACGTTCGTCG |
| 7381 | TCCAGAACGA | GACGCAGTGG | TGGGGCCAAG | GCCCCGACGG | CAAGGTCAAT | GAAGGCCACG |
| 7441 | CGATGGCAGA | GGTCATCGAA | GGCAACATGA | CCAAGGTCGA | GGGCTCCCGC | ACCCTGTCGA |
| 7501 | TCTGCAACGC | CCACATCCCC | GGCACCGAGA | CGGTCGCCGA | GAAGGCATGG | GAGCAGTACC |
| 7561 | AGAAGGTCCA | GGCAGGCGAC | TCTGTCGACA | CCGGGATGAT | GTACGACGCG | CTGGAAGCGC |
| 7621 | CGGCCGACAC | CCCGGTCTCC | GAGATCCCCC | CGCAGAAGGA | GGATCCCGAG | GGATTCGAGA |
| 7681 | AGGGCATCGA | GAAGCTCCGC | GAGGGCCTGC | TCATCGCCCG | AGGCGACTCC | ACCTGGCTGC |
| 7741 | CGATAGACGA | CATCATCAAG | TCGATTCTGT | CGACCAAGAA | CCCGATCACC | GAGTCGCCGG |
| 7801 | GCAAGTTCCT | GAATCAGGTA | AACGCCGCTG | AGGACTCGTG | GCTCTCACCG | CAGGAATGGA |
| 7861 | ACCGGTGCCA | GGTCGACCTG | GCCAAGTACC | TGGATAAGCA | CGGCAGGGAG | TTCGCTCCGC |
| 7921 | TGCACGCGG | TGACCGGATC | ACCCTCGACG | TTCGACGGGTC | GAAGTCCAAC | GACTGGACCG |
| 7981 | CGCTCGTCGG | CTGCCGTGTC | AGCGACGGCC | TGCTGTTCGT | CATCGACATC | TGGGATCCCC |
| 8041 | AGAAGTACGG | CGGGGAGGTT | CCCCGCGAAG | ACGTTGACGC | CAAGGTCCAT | TCGGCGTTCG |
| 8101 | CCCACTACGA | CGTGGTGGCG | TTCCGCGCCG | ACGTGAAGGA | GTTCGAGGCG | TACGTCGACC |
| 8161 | AGTGGGGCCG | GACCTACAAG | AAGAAGCTCA | AGGTCAACGC | CAGCCCGAAC | AACCCGGTGG |
| 8221 | CGTTCGACAT | GCGCGGACAG | CAGAAGAGGT | TCGCGTTCGA | CTGCGAGCGA | CTCGAGGACG |
| 8281 | CGGTCCTTGA | GGGCGAGGTC | TGGCACGACG | GCAATCCCGT | TCTGCGCCAA | CACGTTCTGA |
| 8341 | ACGCCAAACG | ACACCCAACG | AACTACGACG | CCATCGCGAT | TCGCAAGGTC | ACGAAGGACT |
| 8401 | CCAGCAAGAA | AATCGACGCT | GCAGTCTGCG | CTGTCCTCGC | GTTCGGGGCG | AGACAGGACT |
| 8461 | ACCTCATGAG | CAAGAAGGCC | CGTAGCGACG | GGGTGGTGAT | GGTTCGATGA | CAGCACCGCT |
| 8521 | CCCCGGTATG | GAGGAGATCG | AAGACCCCGC | AGTCGTACGA | GAAGAGATGA | TCTCGGCCTT |
| 8581 | CGAGGATGCT | TCCAAGGATC | TCGCCAGCAA | CACCAGCTAC | TACGACGCTG | AGCGCCGGCC |
| 8641 | AGAGGCCATC | GGCGTCACCG | TCCCGAGAGA | GATGCAGCAA | CTGCTGGCTC | ACGTCGGATA |
| 8701 | CCCCAGGCTC | TACGTCGACT | CAGTCGCCGA | GCGCCAAGGC | GTCGAGGGTT | TCCGCCTCGG |
| 8761 | CGATGCCGAC | GAGGCTGACG | AAGAGCTGTG | GCAGTGGTGG | CAGGCCAACA | ACCTCGACAT |
| 8821 | CGAGGCACCA | CTGGGCTACA | CCGACGCTTA | CGTTCACGGC | CGGTCGTTCA | TCACGATCAG |
| 8881 | CAAGCCAGAC | CCGCAGCTCG | ACCTGGGTTG | GGATCAGAAC | GTCCCGATCA | TCCGCGTCGA |
| 8941 | GCCGCCCACC | CGAATGCACG | CCGAGATCGA | CCCCGGATC | AACCGGGTGT | CCAAGGCCAT |
| 9001 | CCGAGTCGCA | TATGACAAGG | AGGGCAACGA | GATTCAGGCT | GCCACGCTGT | ACACGCCGAT |
| 9061 | GGAGACCATC | GGCTGGTTCC | GCGCTGACGG | TGAGTGGGCT | GAGTGGTTCA | ACGTCCCGCA |
| 9121 | CGGTCTGGGC | GTCGTTCCCG | TTGTGCCGCT | TCCGAACCGG | ACCCGGCTCT | CGGACCTGTA |
| 9181 | CGGCACCAGT | GAGATCACGC | CCGAGCTTCG | GTCGATGACC | GACGCGGCGA | CGCGCATCCT |
| 9241 | CATGTTGATG | CAGGCGACCG | CCGAGCTGAT | GGGTGTCCCC | CAGCGCCTGA | TCTTCGGCAT |
| 9301 | CAAGCCCGAA | GAGATCGGCG | TCGACTCCGA | GACCGGCCAG | ACGCTGTTCG | ATGCGTACCT |
| 9361 | GGCCCGGATC | CTGGCGTTCG | AGGACGCTGA | GGGCAAGATC | CAGCAGTTCT | CTGCAGCCGA |
| 9421 | GCTGGCCAAA | TTCACCAACG | CGCTCGATCA | GATCGCCACA | CAGGTCGCTG | CGTACACGGG |
| 9481 | ATTGCCTCCC | CAGTACCTGA | GTACCGCCGC | AGACAATCCG | GCCTCCGCTG | AGGCGATCAG |
| 9541 | GGCCGCTGAG | AGCCGACTCA | TCAAGAAGGT | CGAGCGGAAG | AACCTGATGT | TCGGCGGCGC |
| 9601 | ATGGGAAGAG | GCCATGCGGA | TCGCCTACCG | GATCATGAAG | GGCGGCGACG | TTCCCCCGGA |
| 9661 | CATGCTCCGC | ATGGAAGCCG | TCTGGCCGAGA | CCCGAGCACT | CCCACCTACG | CGGCCAAGGC |
| 9721 | CGACGCAGCC | ACGAAGCTGT | ACGGCAACGG | CCAGGGTGTC | ATCCCGCGTG | AACGTGCTCG |
| 9781 | CATCGACATG | GGCTACTCCG | TCAAGGAGCG | CGAAGAGATG | CGCCGATGGG | ACGAGGAAGA |
| 9841 | GGCCGCAATG | GGTCTCGGCC | TGTTGGGCAC | GATGGTCGAC | GCCGACCCGA | CGGTCCCAGG |
| 9901 | CTCCCCGAGC | CCCACGGCAC | CGCCGAAGCC | ACAGCCGGTC | ATCGAGTCGT | CTGGTGGTGA |
| 9961 | TGCGTGACCG | CAGAGGAGTA | CGCGGCGGCT | CAAGCCGCGA | TCACTGCGGG | TCTTGCCACA |
| 10021 | TACGTCCAGA | GGTTCGCTTC | GCTCTTCGTC | GGTCCAGCTC | TCGCTGTAGG | TGAGTGGCTG |
| 10081 | CGACTGCTGC | AGGTGCTGTT | CCCCGAAATC | CAACGGCGGT | ATGCAGATGC | TGCCGCCTTG |
| 10141 | GGCAGGGACT | TCTACGACTC | CCAACGCGCA | CTACACCACC | CAGAGCTGCC | CCGGAACGAG |
| 10201 | AGGTTCCGGG | GAGAGCTTCG | GTGGGAGTGG | TTCGTCCAGA | ACATGGACGT | GGCTCGAAAA |
| 10261 | GAGATGTCGC | AGGCCGACTC | TCCGCCGAGT | GCGACCTCTA | AGTTGGCTCT | GGCCGCAGTT |
| 10321 | CGCGAAGTGG | AGATGGCAGC | ACGCCGACAG | ATCATCGGCG | CTGTCAAGAA | CGATCCGGCC |
| 10381 | CCGCAGATCG | TGCAGGGCTG | GCCGAGGGTC | GCCACCGGGC | GCGAAACATG | CGCCTGGTGT |
| 10441 | CTGATGCTCA | TCTCACGGGG | TGCCGAGCTG | AATCACAAGG | GCAACTTCGC | CTACAGCTCA |
| 10501 | GCGGAAGCCG | CAGGGCTCAA | CCTCGATGAC | GAGACCGTGA | TCGACCTCTG | GAACGAGTCC |
| 10561 | GGTCACGACC | TTGAGAAGTT | CCGCGAGGAG | ACCAGAGAGG | ACTTCGAGAA | GTGGCACGCA |
| 10621 | GGGTGCGACT | GTCTGGTGGT | CCCGGTCTTC | GATGTGCAGA | ACTGCCCGG | AAGAGACGCT |
| 10681 | GCCCTACGGG | CGCAGCAACT | TTGGATCGAA | GCCAGCGACG | AAGCTGACGA | CCTCATTGCG |
| 10741 | TCAGGCAAGG | CCCGCTCCAA | GAACAAGAAC | ACGGAGACGC | TCAACGCGCT | CCGACGCCGC |
| 10801 | CTAGCACGCG | GCGAAATCAC | CATGTCCAAC | TACGCCCTCG | CTGCCGTAGTC | CCTCGAACCC |
| 10861 | CAGGTGGGTT | CTCTCAACAT | GCCCAGGAGG | CGAAAACACA | TGTCCGACAA | CCCCACTCCC |
| 10921 | GAGAGCACCC | CAGAGGCCGA | GACCCCGGAG | GTCGAGAAGC | CGATGGAACC | GCAGGGCAAG |

-continued

SEQ ID NO: 1

| | | | | | |
|---|---|---|---|---|---|
| 10981 | GTCTTCGATG | AAGCGTACGT | TCAGTCGCTT | CGCCAGGAGG | CTGCAGCCGC | TCGGGTGGCG |
| 11041 | AAGAAGGACG | CCGTAGAAGC | GGCAGAGGCT | CGAGTGAAGG | CCGAGTACGA | GGCCAAGCTC |
| 11101 | GCTGAGCGCG | ACACCGCTTA | CACCGAACTG | CAGAACCAGT | TGGGACAGGC | GTGGATTGAG |
| 11161 | CTGGAGAAGG | TCTACCTCTC | TCTCGACGCC | AAGGTGCCCA | ACGACAAGGT | TCGGGCGTTT |
| 11221 | GTCGAGATCC | TCGAAGGCAA | CGACAGGGAC | AGCATCGCTG | AGTCAGTGAA | GTCCCGTCTG |
| 11281 | GAGCTGGTCG | GCGGATTCGG | CAACAAGACC | CCGAGTCCTG | CGTTCGACCC | GTCTCAGGGT |
| 11341 | CGCGGCGGTA | AGCCGCCGAT | CCCGCTGAAC | GGTGACCCGA | TCCTCGAGGC | CATCAAGGCC |
| 11401 | GCTGTCGGGA | TCAAGAAGTA | ACCCACCCAA | CAGATCTCAA | GGAGAGATAA | ACAATGGCAG |
| 11461 | TCAACCCTGA | CCGCACCACG | CCGTTCCTCG | GCGTGAACGA | CCCCAAGGTC | GCGCAGACCG |
| 11521 | GCGACTCGAT | GTTCGAGGGC | TACCTCGAGC | CCGAGCAGGC | CCAGGACTAC | TTCGCCGAAG |
| 11581 | CGGAGAAGAT | CTCCATCGTC | CAGCAGTTCG | CCCAGAAGAT | CCCGATGGGC | ACGACCGGCC |
| 11641 | AGAAGATCCC | GCACTGGACC | GGCGACGTGA | GTGCGTCGTG | GATCGGTGAA | GGCGACATGA |
| 11701 | AGCCCATCAC | CAAGGGCAAC | ATGACCTCGC | AGACCATCGC | CCCCCACAAG | ATCGCGACGA |
| 11761 | TCTTCGTGGC | CTCGGCGGAA | ACCGTCCGTG | CGAACCCGGC | CAACTACCTG | GGCACCATGC |
| 11821 | GGACCAAGGT | CGCGACCGCC | TTCGCGATGG | CGTTCGACAA | CGCCGCGATC | AACGGCACCG |
| 11881 | ACAGCCCGTT | CCCGACCTTC | CTAGCGCAGA | CCACCAAGGA | GGTCTCGCTG | GTGGACCCGG |
| 11941 | ACGGCACCGG | CTCCAACGCC | GACCTCACCG | TCTACGACGC | GGTCGCCGTC | AACGCCCTGT |
| 12001 | CGCTGTTGGT | CAATGCCGGC | AAGAAGTGGA | CCCACACTCT | GCTGGACGAC | ATCACCGAGC |
| 12061 | CGATCCTCAA | CGGCGCGAAG | GACAAGAGCG | GTCGCCCGCT | GTTCATCGAG | TCGACCTACA |
| 12121 | CCGAGGAGAA | CAGCCCGTTC | CGCCTCGGTC | GGATTGTGGC | CCGTCCGACC | ATCCTGAGCG |
| 12181 | ACCACGTCGC | CTCGGGCACG | GTCGTCGGCT | ACCAGGGTGA | CTTCCGCCAG | CTCGTCTGGG |
| 12241 | GCCAGGTCGG | CGGCCTGTCC | TTCGACGTGA | CGGATCAGGC | GACTCTGAAC | CTGGGCACCC |
| 12301 | CCCAGGCTCC | GAACTTCGTC | TCGCTGTGGC | AGCACAACCT | CGTCGCAGTC | CGAGTCGAGG |
| 12361 | CCGAGTACGC | CTTCCACTGG | AACGACAAGG | ACGCGTTCGT | CAAGCTCACG | AACGTGGACG |
| 12421 | CCACCGAAGC | CTGATCCAGG | CTTGACATCC | ACCGGGAGGG | GGCTCCTTCG | GGAGCCCTCT |
| 12481 | CCTGATGTGG | AGCAGGAAGG | ACCACATGCG | AATCCAGTCC | ACCCTCAACG | GCGGTTTCGC |
| 12541 | CGAGGTTTCC | GAGGAGTTCG | CCAAGCAGTT | GATCGCCACT | GGCGGCTGGA | AGGTGCCCCG |
| 12601 | GAAACCGCGC | AACACCAAGA | CCAAGACCGC | TCCTGAGGAG | CCCAAGAACG | AGGAGTAACC |
| 12661 | CGTGGCCTAC | GCGACCGCCG | AAGACGTTGT | GACGTTGTGG | GCCAAGGAGC | CTGAGCCCGA |
| 12721 | AGTGATGGCG | CTGATCGAGC | GCCGGCTCCA | GCAGATCGAG | CGCATGATCA | AGCGCCGGAT |
| 12781 | CCCCGACCTG | GACGTGAAAG | CCGCTGCGTC | GGCGACGTTC | CGGGCCGATC | TGATCGACAT |
| 12841 | CGAAGCTGAT | GCTGTTCTGC | GCCTCGTACG | TAACCCGAGG | GGCTACCTCT | CGGAGACCGA |
| 12901 | CGGTGCGTAC | ACCTATCAGC | TCCAGGCCGA | CCTGTCGCAA | GGCAAGCTCA | CCATCCTCGA |
| 12961 | TGAGGAGTGG | GAGATCCTCG | GGGTCAACTC | CCAGAAGCGC | ATGGCGGTCA | TCGTCCCGAA |
| 13021 | CGTGGTGATG | CCGACGTGAG | CGCGAGCGAC | CGACACCGCG | CCCCGATTGT | CTATCCGCCT |
| 13081 | GGCACTCAGG | CGGTTACGCC | GGATCGGGTC | AACGCGTTTG | ACTGCGATCA | CGAAGCTGAT |
| 13141 | CCTCCGGTGT | GCCGGTGCGT | CCACGACTGG | CGCATCGAGT | GGGGAAACGT | CAAGAAGGCC |
| 13201 | ACCGCCAGAT | CACGGTCGGC | GGTGCTCTGA | TGAGCCTCCT | CGACACCGGT | GCCCGGTACC |
| 13261 | AGACCTGCAT | CGTCTACCCC | GAAGAGATGG | TCATCGACTC | CGATGGCAAC | AAGCGGACCA |
| 13321 | GGCCGTCGAA | TACCGGCATC | CCGGCCATCG | CACGGTTCCA | GGTAGCCAAC | CAGTCTGGTA |
| 13381 | CGTCGGCACG | ACGTGCTGAG | CAGGACAACG | AGGGGTTCGA | GACCGAGAAG | GTCTACCGGA |
| 13441 | TGCGGTTTCC | CCGCTCGTTC | ACCAAGGAGC | ACGGCATCCT | CGGGGCCCAG | TCCCAGATCG |
| 13501 | AGTGGCGAGA | CCAGCGGTGG | GCGCTCTTCG | GAGACGCCAC | CGTCTACGAC | TCATCCCCTG |
| 13561 | CGTTGGCGCG | GGTCGACTAC | ACGATCAAGA | GGTACTGATG | GCCAAGGTCT | ACGCGAACGC |
| 13621 | GAACAAGGTC | GCGGCCCGGT | ACGTCGAGAC | GAGGGACGCC | GTCCGAGACG | AGCGGAACAA |
| 13681 | GGTCACCCGT | CGAGCCAAAG | CCAATCTGGC | GCGGCAGAAC | TCGACCACCC | GCATCACCGA |
| 13741 | CGAGGGCTAC | TTCCCGGCCA | CCATCACCGA | GCAAGACGGC | GATGTCGACT | TCCACACGAT |
| 13801 | CCTCAACGCG | CCCAACGCGT | TGGCGTCCA | GTTCGGCCAC | GCGCCGTCTG | GCTTCTTCGC |
| 13861 | TGGCCACCGAC | ACGAAACCAC | CGGAGGCCAC | TTACATCCTC | ACCCGAGCCG | CCATCGGCGG |
| 13921 | CACCGTCTCA | TAAGGAGGTC | ACATGGCGCG | AATGCCTCGC | GTCCAGGCAG | TAGCGGCCCC |
| 13981 | GATCCTCCGG | TCAGACCCCC | GACTGGAGGG | AGTGACGGTC | ACGACATGGG | TTCCAGACGT |
| 14041 | GGACTTCCGA | GAGTTCCCGA | TGATCAACCT | CCGCCGCAAG | GGCGGGACGA | GGAACCCCAA |
| 14101 | CGCACCGACG | CTGCACACGC | TGCCGGTGGT | CGAAATGACC | GCCTACACCA | GAGACGGTCT |
| 14161 | CATCGAGACT | GAGGAGCTGT | ACGAGACCGC | GCTAGAGGTT | CTCTACGACG | CGGTGGAGAA |
| 14221 | CGGAACACAA | ACTCCCGCAG | GGTATTTGAC | CTCCATCTTC | GAGACGATGG | GCGCCACTCA |
| 14281 | GTTCAGCTCC | CTCTACCAGG | ACTCCTGGCG | CATCCAGGGT | CTGATCAGGC | TCGGCGTCCG |
| 14341 | CAGACGGAGA | ACCACCCTCT | AACCGAAAGG | TAAAGCCACA | TGGCTGAAAA | CGACGACGCA |
| 14401 | GTGTTGACTG | CGGCGGTCGG | CTACGTGTAC | GTCGGTGCTG | CAGGCACCGC | TGCTCCTACG |
| 14461 | CCGGCCTTGC | TCAAGACCAT | CGACCTCAGC | AAGCCCGAGA | CCTGGACCGG | TGCTACCGGT |
| 14521 | TGGACGAGCG | TCGGCCACAC | CAGCCGAGGC | ACGCTCCCTG | AGTTCGGCTT | CGAAGGCGGC |
| 14581 | GAGTCCGAGG | TCAAGGGCTC | CTGGCAGAAG | AAGAAGCTCC | GCGAGATCAC | CACCGAGGAT |
| 14641 | CCCATCGACT | ACGTCACGGT | CCTACTGCAC | CAGTTCGATG | AGCAGTCGCT | GGGTCTGTAC |
| 14701 | TACGCCCCA | ACGCCTCTGA | GACTCCTGGT | GTGTTCGGTG | TGAAGACCGG | CCAGACCCAA |
| 14761 | GAGAAGGCCG | TGCTGGTCGT | GATCGAAGAC | GGCGACATGC | GCCTGGGGCA | TCACGCCCAC |
| 14821 | AAGGCTGGAG | TTCGCCGTCA | CGACGCGATT | GAGCTGCCCA | TCGATGACCT | GGCTGCGCTG |
| 14881 | CCCGTCCGGT | TCACCTACCT | GGACCACGAA | GACGAGCTGC | CGTTCTCCTG | GATCAACGAA |
| 14941 | GACCTCTTCA | ACGTGCCCGA | GGTTCCCGAG | GGCTGATCCC | AACTTGACAG | CCACCCGGCT |
| 15001 | GTCTACCCCG | GAGGGGAGG | TTTCCTTGGC | GGGCCTGGCC | TCCCCTCCT | CCCGCCACTC |
| 15061 | ACAGACCCGC | CGACACTGAA | AGGTTCGCCA | TGACAAACGT | ATTCACCATC | GACGCATTCC |
| 15121 | GCGAAGAGGT | CAAGAAGAAG | TACGCTCCGG | TCCTCATCGG | CCTGTCCGAC | GATGTGACCG |
| 15181 | TCGAGCTGAA | GCCGCTGCTG | AAGCTGGGCC | AGAAGGCCCG | CGAAGCGGTG | GTCGAGGTGT |
| 15241 | TCAAGGAGTT | CGCGGACATC | CCCGACCTCG | AAGAGGACGA | CGACGACGAG | TTGGTCGATC |
| 15301 | AGTACTCGCT | CCAGGTCTGC | GACATCATCG | CCAAGCGCTT | CCGGCTGATC | GCCACGAAGC |
| 15361 | CCAAGACAAGCT | GATCGCCGCC | TTGGACGAGG | AGCCGGATCC | CCGTATCCGC | GCAGAGCTGT |
| 15421 | ATGCAGCGGT | ACTCAACACC | TGGAAGCGAG | AGACGCAACT | GGGGGAAGCC | GCGCCCTCGC |
| 15481 | CGAGCTGATC | GACAAGTTCG | GCGGGGCGAT | CCTCGCAGAC | CTGCTCCAGT | ACTACCGGGT |
| 15541 | AGACCTGCGC | GACCTGTTCC | GCGACGAGGA | TCCGCTTTCG | CCGAGATTCG | TTCTGTCCCT |
| 15601 | GGTGCTCTGC | CTTCCCAAAG | ACGGCGCGTT | CTACGCAGAA | CGTCGTGGTG | GGCAGCAGTA |

-continued

| SEQ ID NO: 1 | | | | | |
|---|---|---|---|---|---|
| 15661 CCGGGGCTGG | ACCGAGGACC | GCTACGCGCT | CGCGGACATC | TACGACGCCA | TCCAGGCGGG |
| 15721 CAACCACATC | CTGCTGCTGG | CGAATCGTGA | TCCGAAGAAG | CCAAAGCCCA | AGGCACCCAA |
| 15781 GTCATACCCG | CGTCCCGACG | ACCTAGAGAA | GACCACACCG | AAGCCGGGTT | CGTTCGCCGC |
| 15841 AATGGTCGTG | CGAGCGAAGA | AGGCGGCTCG | AGAGAGAAGG | GAAAGGGAGG | AGGAGAGTGC |
| 15901 CGAATAGTGC | TGGCGTAGAA | GTCGCCCGGA | TCTCGGTCAA | GGTCAGCCCG | AACACCAAGG |
| 15961 AGTTCCGCCG | GGAACTCAAG | ACCGAACTCG | AGAAGATCGA | GCGGGAGCTT | AAGGGCGATG |
| 16021 TCGAGATCAA | CGGTCATCTC | GATGCGGCCC | AGGCCAAGGC | CGACTTCAAG | CGCATGATGA |
| 16081 TGCAGCTCAA | GACCGAAGCT | GCCAAGGGCG | TTCACGTCCG | GGTCGACGTA | ACCGTCGACA |
| 16141 AGAAGAGCAA | GAAGGGAGGT | CTCCTCGGAG | GTCTCCTCGG | CGGCAGCCGG | GGGCTCGGAG |
| 16201 ATCTAGGCGA | TGACGCCGAG | AAGGCGTCGT | CTCAAGTACA | ACACCTTGGC | AAGTCGTTCC |
| 16261 TGGGCCTCAC | ACGAGCCGCC | TGGATAGGCG | TAGGCATCGT | CGCCGTAGCA | GCTCCGCTGG |
| 16321 TCGGCATCGT | GGCCGGTCTG | CTGGCCGGTC | TGCCGTCGCT | GCTGTCTGCG | TTCGGAGCCG |
| 16381 GCGCTGGCGT | AGTCGCGCTC | GGCATGGACG | GCATCAAGGC | AGCCGCCTCG | ACGCTGGCCC |
| 16441 CGACGCTGGA | GACGGTCAAG | GCCGCTGTCT | CCTCGACGTT | CCAGCAGGGA | CTCACCCCGG |
| 16501 TCTTCCAGCA | GCTCGGCCCG | ATGCTGACCG | CGATCACCCC | CAACCTGCAG | AACGTGGCCT |
| 16561 CGGGCCTCGT | GAACATGGCC | GGGTCGATCA | CCGACGTGAT | CACCCAGGCT | CCTGGTCTGC |
| 16621 AGCAGATCCA | GAACATCCTC | ACCAAGACCG | GAGAGTTCTT | CACGGGCCTC | GGCCCTGTGC |
| 16681 TCGCTACCGG | CACGCAGGCG | TTCCTGACGC | TGTCCAACGC | CGGCGCGAAC | TCGTTCGGCA |
| 16741 CGCTCCTGGC | TCCCCTGCAG | GAGTTCACCA | ACGGCTTCAA | CGACATGGTC | AACCGAGTCA |
| 16801 CGTCCAACGG | CGTGTTCGAG | GGTGCCATGC | AAGGGCTTTC | GCAGACGCTG | GGCAGCGTCC |
| 16861 TCAACCTGTT | CAACCGGCTC | ATGGAGTCCG | GTCTGCAGGC | GATGGGACAG | CTCGGCGGTC |
| 16921 CGCTGTCGAC | GTTCATCAAC | GGGTTCGGAG | ATCTCTTCGT | CTCGCTGATG | CCGGCGCTGA |
| 16981 CTTCGGTCTC | TGGTCTGATC | GGCAACGTCC | TCGGGACGCT | GGGCACACAG | CTCGCTCCCA |
| 17041 TCGTCACGGC | GCTCACGCCG | GCCTTCCAGA | CGCTGGCGAG | CACGCTCGGC | ACGATGCTCA |
| 17101 CCGGAGCCCT | CCAAGCTCTG | GGTCCGATCC | TGACTCAGGT | CGCTACGTTG | ATCGGCACGA |
| 17161 CGCTGAACAC | GGCGCTGCAG | GCTCTCCAGC | CGATGCTGCC | GTCGCTCATG | CAGAGCTTCC |
| 17221 AGCAGATCTC | CGACGTACTG | GTGACCAGTC | TGGCCCCGCA | CATCCCGGCG | CTGGCGACGG |
| 17281 CCCTCGGCCA | GGTCGCAGGC | GCGGTGCTGC | AGCTCGCTCC | GACGATCATC | TCGACGTTGG |
| 17341 TTCCGGCGTT | CGTTCAGTTG | GTCCCAAAGG | TCGCTGAGCT | AGTTCCGACC | ATCGTCAACC |
| 17401 TGGTCCAGTC | GTTCGCCAAC | CTGATGCCGG | TGGTTCTGCC | CCTGGCGCAG | GCTCTGGTCA |
| 17461 GCGTTGCTGG | CGCGGTGATT | CAGGTGGGTG | TCTCCATCGG | CGGCGCGCTC | ATCGGCGCGC |
| 17521 TGGCGAACCT | CACGGAGATC | ATCTCCAACG | TCATCAAGAA | GGTGTCCGAG | TGGGTCAGCA |
| 17581 GCTTCTCCAG | CGGAGCCCAG | CAGATCGCTG | CGAAGGCAGC | GGAACTGCCG | GGGATGATCC |
| 17641 AGTCGGCTCT | CGCCAACCTG | ATGGCCATCG | GCCTGCAGGC | CGGTAAGGAT | CTCGTCCAGG |
| 17701 GCCTGATCAA | CGGCATCGGC | GGGATGGTCA | GCGCAGCGGT | CAACAAGGCC | AAGGAGCTGG |
| 17761 CGTCCAGCGT | GGCTGGTGCA | GTGAAGGGCT | TCCTGGGCAT | CGAGTCCCCG | TCGAAGTTGT |
| 17821 TCACCGAGTA | CGAACCAGTTC | ACCGCCGAGG | GATTCGGACCA | CAGGCATGGAG | GCAGGGTTCA |
| 17881 AGCCCGTCAT | CGAACGGGCC | AAGGATCTCG | CGGCTGAGCT | GTCCAGGGCG | ATGGAGTCGG |
| 17941 GCACCGACCC | CTCCGGGATT | CTCGCTGGGC | TGGATCAGAA | TGAGCTGAAG | CAGATGCTGG |
| 18001 CGGCTCTCGA | AGAGGAGCGC | AAGCGACTCA | AGGTCGAGAA | GAACGGTATC | CCCAAGGGAG |
| 18061 ACAAGGCAGG | CCGAGAGGCG | CTGCAGAACC | AGCTCGACCA | GACTCAGGCG | CAGAAGGACA |
| 18121 TCCTGTCCTA | CCAGCGTGAC | CGCATCAAGA | ACGAGTCTGA | GTACGGCGAC | ATGGCCGGCG |
| 18181 AAGACCCGTT | GGTGAAGGCA | GCCTCCGGGC | TGATGAGCGC | ACCGGTCGAC | TTCGCGAAAG |
| 18241 CGACTGGCAA | GCAGTTCCTT | TCGGACATCG | GCATCAGCGG | AGATGGGTTC | ATCTCGAAGG |
| 18301 CCATCACCGA | GGGCATCCAG | TACATCTTCC | AGATCGGCTC | TGTCGATGAG | GCGCTGTCGA |
| 18361 TCAAGGACCG | CGAGGAGTCG | AAGAACGCGC | TGTCCGTCGT | TGGCCGCTGA | CTTGACATCC |
| 18421 ACCAGGAGGT | AAGCATTGAT | CACCGACACC | ATCGTTGAAC | TCGAGGGTGT | CAATGGTGAG |
| 18481 CGTTTCAACT | TGACGACCGG | TGACCAGGGT | GTGTACCTGG | CCACAGACGT | GGAGGGTTGT |
| 18541 TTCTACGACC | CTCCCGTCAA | GGTCGTTGTT | GAAGAGCCCG | GGAACTACCC | CGGCGCTCGC |
| 18601 TACTTGTCCC | ACCGAGCCCT | GAAGCGAGAC | ATCGTCTTTG | GGGTCGTCAT | CCTCAACGCC |
| 18661 GCGAAGCAGG | GGCCGCGCTC | CTGGCTGTCG | CGAGACTCCG | AGTGGCGCAA | GGCGTGGGCG |
| 18721 TTCAACCGCA | CCTGCAAGCT | CTACGTCACC | ACCCCGGACT | CCGGTACCCG | CTACCTGAAG |
| 18781 CTGGCGCTGT | TCGAGTCCCC | CACCGTCAAG | ATGGACACCG | ACCCAAGAGG | TAAACCCCTT |
| 18841 GAGGTCACGG | TGATGTCGTG | CATCGCGTAC | GACCCGTTCT | GGTACGAGGA | CGACAAGGTC |
| 18901 TTCTCGGCCA | AGACCAAGAC | CGACACCCGG | TTCGACCCGT | CGTTCTGGAC | GCCGCCGTGG |
| 18961 CCGTGGGAGG | AACTGCCCAA | GGAGACGCTG | CGGATCAAGG | TCGGCCGCGA | GCAGGGTGGG |
| 19021 CTAAACCCCA | CCGACCAGTA | CATCTTCCCG | AAGTGGACCG | TTCCCGGCTC | CACCGAGAAG |
| 19081 GTGCCGAACT | TCCCCTGGCC | GTTCCCCCCG | AACGTCCCGA | TCCCGTGGGA | GACAGCACCG |
| 19141 TTCACTCAGT | TCGTCATCCC | GGACTACTCG | TTCGAGGATG | AGGAGTTCCG | CAACCGCCGG |
| 19201 CTCAAGACGC | CGGGGTTGAT | CTACGGCGAG | AACTGCGTCA | TCGACACCGA | CCGGCGCGAG |
| 19261 GAGCAGATCG | CTTCCGAGTC | GGGCTCCCCG | GTGTGGGGTC | GGATGAACGG | TGTCCGGTTC |
| 19321 CGCAACTCGA | TCCCGCCCTA | CACCGAAGAG | GCTGAGTTCG | TCATAGACGC | ATCGGGATGC |
| 19381 GCTCCGGGAC | AGGTAGTTAC | CCTCCGGCTC | ACGAGGCCGT | GGTGCGCGTG | CTGGGGGCTA |
| 19441 GAGTGAGTGG | TCTGACGAGC | GTTCGTGAGG | CCGAAGATCT | CTGGCAGAAG | ATCCAATTGC |
| 19501 GGCGCTGCAA | GCGCGGAGCAG | GAACGGCTCA | AGCATCCCGA | CGTAGAGCTG | CGCGATGGCG |
| 19561 ACTTCCGCCT | GCGCGGCCTG | GTCGCTGGCG | AGCAGGTGCT | CGAGTGGGAG | TTCATCGAGA |
| 19621 ACGAGACTGG | CACCTGCACC | TTGCAGCTCT | CACTGAGCCA | TTACCTGGCG | AAGTGGGTGA |
| 19681 TGGACCACCG | GGGTCGAGCA | AAGCGCAACG | TCATCATCAA | CATCGAGAAG | CAAGGCGCTC |
| 19741 GATGGACCGG | GATGATGGAC | CACTACCGGG | TCATCAAGAC | CGACGCAGGG | GACGCCTACA |
| 19801 TCGAGATCGT | GTTTTTGCAC | GACTTCGAAC | AGACCAAGCA | TATCCGGGTA | TGGTGCAACC |
| 19861 CGTTCCTACG | CCCCGAGCTG | CAGTTCCCCA | AGGTGTGGAT | CATCTTCGGG | CCGGCCAAGT |
| 19921 GGTGTTTGCT | GGTGACACTG | TTCGTCAACC | TGCTCAGGCT | CGAGACGAGC | TTGTGGACGC |
| 19981 TGCCTGATGA | CCCCACCGAC | ATCAACGAGT | GGATGGGTCC | GAGCTTCAAC | CCAGCAAATT |
| 20041 GGCGGAACAT | CGTCAAGCCG | TTCCCGTTCC | TGGCCGACAA | CTCACCGTGT | ACGATGGTGT |
| 20101 TCAGCCGGTT | CGGGACGTTC | TACGACACCG | CCAAGAAGAT | CCTCGAAGAC | CATCAGCTCA |
| 20161 CGCTGACGTG | TCGTCGGTAC | ATCAAGGACC | GCGACCCGCA | TCCGTTCGAA | GATCTCAAGG |
| 20221 GGCTCTGGGG | AATTGATCCT | GTCGAAGACC | TGCTGCAGAA | GATCCCGCTC | CGGGACGGCT |
| 20281 GCGTGGTCTG | GGACATCGAG | GACAACTCAG | GTTGGGGCAC | TCAGACCGCG | TTCGGCGGTT |

SEQ ID NO: 1

| | | | | | |
|---|---|---|---|---|---|
| 20341 | CGTGGCTGAC | CGGGTTCGTC | CGAGGGATGG | TCCAACTGGC | CGGCGACGGC | CAGGTCGAGG |
| 20401 | GCGTCGATGT | GTTCACCGGG | GACTACACGT | TCCCAGGCGA | GTACTACTCC | CCCTGGTTCA |
| 20461 | TGGGCACCAG | CCCGATAGCA | CCCCACGTCG | TGTTCGAAGA | AGGACCGCTG | ACCGGGATCA |
| 20521 | AGTCGTCGGA | GTTCTCGTAC | TACGAGGCCA | CCGACACCAG | CTTCCTGGCT | GGTGGACAGA |
| 20581 | GCGCACCTGG | CATCAACGAG | GGCATCTCGG | CCCTGGTGAA | CATCGGTGCC | GACCTGCTGA |
| 20641 | CCTCGTTCAT | CAACAGCCAG | CTCGCCGCGC | TCGGCGCGGT | CGGTGGAGCG | ATTGACCTCC |
| 20701 | CGCCTCTGGG | CGGTCTGCTC | GATGCGGTGT | TGCACCGTCT | GTACTCCGAT | GTGTTCGGCG |
| 20761 | CGTTCATGGA | AGTTCCGACT | CTGCGTGCGA | TGGGCATCTC | GCTCCCGATC | TCCGGCTCG |
| 20821 | AGGACATCGT | CACCGGACTG | GGCGACTTCC | ACTACTTCGA | GAACATGGCC | GACGGGGCGA |
| 20881 | TGAAGGCGTT | CACGCTGTCA | GCGTTCGCAG | CCATCGCATC | GCAGATCCAC | AAGACGAGGG |
| 20941 | CTCGAACGAC | CCACACCCTC | AAGGTGTCTG | ACGCCGCTCC | GTACATCTTC | GCGCCAAAGC |
| 21001 | CCTACGGGCA | CTGCTGGATC | GGAGATCGCG | TCGGCACGTC | GGTCCTCGGC | TACCCGGTCG |
| 21061 | AGCACCAGTT | GTTCGTGGAG | CGCATCCGCA | AGGTGAAGTA | CCGCATCGAC | AAAGACGGCA |
| 21121 | TGAAGCCGTT | GGAGATCGAG | ATCGGTTACC | GCGAACCGAA | GAACCCAGCA | CTACACATCC |
| 21181 | TCGAAGAGAT | CAAGCGCGTC | AACGGCGCTC | TTGGCACTGC | GGGGATTCTC | TAAACCGAAA |
| 21241 | GGCACGCCGC | ATGATTCCCT | CACAAGAGTC | TCACAATCCG | AACGACCCGC | GACAGCACGT |
| 21301 | CATGTGGGCG | CTACGCAATC | TCCCGATGAT | TGCTGGCGTC | GGGGCGATCA | CGCATCCGGG |
| 21361 | TTACCTGGCG | GATTGGTCAG | AGCACTTGTG | GAAGTGCGGC | TTTCGGCACG | TCGACTGGCT |
| 21421 | CCGGGAGCTG | GCTGATGAGG | ACGGCAACAT | CCACGTCAGT | CAGCTTCCTG | ACCAGGAGAT |
| 21481 | CAAGTTTCAG | CAGCCCTTCC | GGGGCCAGCG | AAGCGACTAC | AACAACGCAG | CTCGATGGGT |
| 21541 | CGGCAAAGAC | GATCCTGACC | CAGAGCCCGT | GCGTATTCCA | GACATTCGCA | AGCTCACAGA |
| 21601 | CCAGGAGAAC | AGAGCGATGA | TCGCGCAGTA | CGAACGAGAC | GGTTGGATCA | AGGATGGATC |
| 21661 | CCCCGGCCCA | GCGATAGCCG | AGGTCGTGGA | GTGACCCCGT | TCAACCCAGA | CTCCATAGGC |
| 21721 | GACTACGTGA | CACTGCTCGG | CGTTGCGTTC | CTGACCTTCT | CGGTTCCCGC | ATGGTTCACC |
| 21781 | GGACGAGCAC | GCAAGCACAG | CAGTGACATC | GGCGAAATCA | AGGAACAGGT | ATGTAACACC |
| 21841 | CACGACACGA | ACCTGCGCGA | TGACCTCGAC | AGCGTCAAGG | CAGACATCAG | CGACTTGAAA |
| 21901 | GAGATTGTGT | TGCAAGGGTT | CCACCAGGTG | AACGAGTCGA | TCAACCTCGA | GCGCCGTGAG |
| 21961 | CGGATCGAAG | GAGACCGCCG | AAAGGAGGTT | GCGTGACCTA | CCCCACCAAC | CCACTAGAGG |
| 22021 | CCATCGGCGC | TGACGGCGCA | TTCGAGATCG | GTGGGGGCGA | CTGGAGCTTC | GGCCAGGACT |
| 22081 | ACACCGAACA | GGCCATCCGG | GCTCTGTTCA | CGATGCCAGC | GGTCACGATG | GAGAACGCTC |
| 22141 | TCGGCCTGCT | CGAAGAGCAC | CTGCTGAAGC | TGCCTCTGGA | GGCGCTGCAG | GGCTTCAAAG |
| 22201 | ACATGATCCC | GGACTGGGTC | GAAGGAGCAT | TCGACACCGGT | CACCGGCGCT | GTGCAGGCGA |
| 22261 | TCATGAACGC | GCTCCAAGAC | GGCCCGCTGT | TCCTGAAGTT | CGCCGAGTTC | CAGCTCTTCC |
| 22321 | TGCAGCGTCT | GCTGAACAAC | CCGGCCGAGG | TCATCGGCGA | GATCCCCCAG | ACGTTGATCG |
| 22381 | ACGGCCTACA | GGACGCGCTC | AACACCGTCA | ACAACACCAT | CCAGACCATC | GTGGACATGC |
| 22441 | TCCTGCAGGC | GCTGGGCATC | ACCCCGGAGG | GGGAGCTGAT | CCGGCGGATC | TTCGACCTGA |
| 22501 | GCGATGAGAT | GGAGTGGCTG | CAGACCGCAG | CCTCGAATGC | AGCTACCGGC | ATCCAGGACA |
| 22561 | CCTGGAACAA | GTTCTGGGGA | GCCCTCACCG | GGCGCGTCCC | AGACCAGGAC | CAGACCGTCG |
| 22621 | CTGAGCCCGC | CGAGCGTATC | GGCGAGCTGG | CCGGCACCAC | GTCTGCTAAC | TCGTCTGCCA |
| 22681 | TCGCCGGAGCT | GCAGCGTCGA | CTGGACAAAC | AGCAGAACGC | TGGCGCCGTG | GCCGGCGGTG |
| 22741 | ACGACTTCGA | GCGACTGAAC | ATATCCGGTT | GGGACATCGA | GTATTCCAAC | GGATCCAGCG |
| 22801 | GCCGAGGGTA | CTACCGTGCC | GACGGCCACC | AACTGGTCTG | GATGGACGAA | GGCAACCAGC |
| 22861 | AGAACACCGC | GACGTTCGTC | CGCACCAACC | CCGCAGACGA | GAAGACAGCC | ACCGACTACC |
| 22921 | AGAAGATGAC | GTTGGTCGTC | GGGACTATCT | CCGGTGACGTG | ACAGACCGTG | TTCCCGCCGA |
| 22981 | AGGGAGGTTC | GCACACCCGG | CTATGGGTCC | GCGTCAACGA | CAACGCTCCG | ACCGTCGGCA |
| 23041 | TCACCGACGG | CGTGTTCGTA | GAGATCGGCG | GCGTATCGAA | GGCCCAGATC | GGCTACCGCC |
| 23101 | GCAACGGCAA | TGACACGTTC | GTCGGATCTA | TGGTCGACTG | CACCTGGGGT | GCTGGATCGA |
| 23161 | TCTTCGCTCT | GACCGCCGGC | ACGGCCAACG | GTGCTGAGGA | GTTCGAGGTC | TCGAAGAACG |
| 23221 | GCCCCGTGCT | GGCCACATGG | TCGGACGACG | GCGTCGTCTC | CGCGATGGGT | GCGAACTACC |
| 23281 | GCCGCTGGGG | CTGGGAAGGC | CAGGCTCGTA | ACCGCAACCT | CGGCCAGGGC | ACTCCGAACT |
| 23341 | CGGTCACCCG | AGTGACGATC | ACCGACAACG | ATCCTACCGG | CGCAGGCGGT | GGAGCTGTCA |
| 23401 | ACGTCGGAGG | AGATGTCGTA | GGTGTACTCC | CCATAGAGAA | CGGAGGCACC | GGAGCTTCGA |
| 23461 | CAGCTTCGGC | AGCCCGTACC | GCTCTCGGAA | TCGATGACCT | GGTCGAAGAT | ATGTCCGACG |
| 23521 | TAGTTCGTGG | ATCCGTCGAA | GGACTCCCGT | TGATACCGAA | GATCTGGGTA | GGAACAGAAG |
| 23481 | CTCAGTACAC | GGCTCTCGCC | ACCAAGGATC | AGTCCACGCT | ATACTTCAGG | ACCGCTTAAT |
| 23641 | GACTGGTATC | TCGTTGGGTG | TCAACGACAT | CCGCAACCTC | TCGATATTCT | TAGGCGTCAG |
| 23701 | CAACAAGATA | TTGAAGGTCA | GTCTAGGCAC | AGAAAAGGTA | TGGCCTGCGT | TCACCCCGGT |
| 23761 | GCTGACCACG | TTCGCCACGG | TCGGCACGTA | CACCTACAAC | ATCCCCGACG | GGGCCAAGTT |
| 23821 | CATCGACGTC | ATCCTCCTCG | GAGGAGGCGG | CGGGGGTAAA | GGCATGGCCC | TGGCTGACGG |
| 23881 | CTGGGGCAGA | GGTGGAGACG | CCGGAAGCTG | GGCTATCGTC | ACTCTCGAAC | GCGGGGTACA |
| 23941 | CATCCCGTTG | TCGACCAAGA | CGATCACCGG | GCTCGTCGGA | GCTGGAGGCG | CAGCGGGAGC |
| 24001 | TGGCTCTGTA | TTCTCAGGCA | AGGCCGGAGG | CCCTGGAGGA | AACACCACGG | CGTCCGCTGT |
| 24061 | CGGATGGTCA | GGTTTGACCG | CAACCGGCGG | TCCCGGAGGC | TCTGTGATCG | ACATCCTCAG |
| 24121 | CGTCGCCGGA | AAGTCGCCTG | GAGATCGGAC | CTACAACGAC | CAGCTCTACA | TAGGCGGCGC |
| 24181 | ACAACAGAAC | TCAGCTGGCG | GGAACGGCAA | TGCTCCTGGC | GGCGGCGGGG | CTGGTGCCCA |
| 24241 | GGTCTCCGCA | CAGAGCGGCG | GTGCTGGCGC | TCGCGGCCAG | GCGTGGTTCT | TCGCGTACTG |
| 24301 | ACAAGAAACC | CCCCTCTTTA | GGACTCAGTG | TCCTTGGGAG | GGGGGCTTTT | TGCGTTTCAG |
| 24361 | GAGGTCTTGG | CCAGCTTGGA | CATCGCCTCA | GCGATAGCCT | CGTCGCGGGC | CTCAGACGCC |
| 24421 | ATCTGGTACT | TCATCGCCAT | CCTAGGAGTC | GTGTGACGGA | GACGGCGCAT | CAGCTCCTTG |
| 24481 | GTCGTCGCAC | CTGCCTGAGC | GGCGAACGTA | GCGCCGACAG | CGCGGAGGTC | GTGGATGCGG |
| 24541 | AGTTCCGGCC | GACCGATCTT | GGCGTAGCCA | CGCTTCAGCG | ACTTGGTGAA | CGCGGACTTC |
| 24601 | GACAGCCGGT | TGCCCTGCGT | CGTGGTCACC | AGGAATGCCT | CGGGGCCCTT | GTTCATCTTC |
| 24661 | GTACGGTCCT | TCATGTGCGC | TCGGATCATC | TCCGCGGAAC | TGTTCCCCAC | CGTCACAGGA |
| 24721 | CGCTTCGACC | GGACGGTCTT | GGCGTTGCCA | ACGACGATCT | TGTTCCCCAC | GCGGGAAGCG |
| 24781 | CCACGGCGCA | CCCGGAGCTT | CATCGTCATG | CCGTCGTCCA | CGATGTCCTT | GCGGCGAAGC |
| 24841 | TCGATCAGCT | CTCCGAACCG | GAGGCTCGTC | CACGCCAGGA | TGTATGCCGC | GATCCGGTAG |
| 24901 | TGCTCGAAGA | TCTCAGCGGC | GACGATGTCC | AGCTCCTCAG | GCGTCAGCGC | CTCTACGTCG |
| 24961 | CGCTCATCGG | CTGCCTTCTG | CTCGATCCGG | CACGGGTTCT | CTGCGATCAG | CTTGTCCTCG |

SEQ ID NO: 1

| | | | | | |
|---|---|---|---|---|---|
| 25021 | ACCGCTGTGT | TCATCACCGC | CCGGAGGACG | TTGTAGGCAT | GCCGGCGGGC | AGTCGGGTGC |
| 25081 | TTCCTACCCA | TCCCGGCCCA | CCACGCACGC | ACCAGAGCTG | GCGTCATCTC | TGTGACCGCC |
| 25141 | ACTTCACCTA | GCACCGGGTA | GATGCGGCGC | TCCGCGTGCC | CGCTGTACAG | ATCCCTGGTG |
| 25201 | CCGTCTGCGA | GGTCGCGCTC | CACGAGCCAC | TTCCGGGTGT | ACTCCTCCAG | CGTGATGGCG |
| 25261 | CTGGCGGCTG | CCTTCTTCGC | CCGGTCCTGT | GGAGGGGTCC | AGGTCTCCAT | CTCGATGAGC |
| 25321 | CGCTTCTCGC | CCGCGAGCCA | GGCTTCGGCG | TCCATCTTGT | TGTCGTAGGT | CTGCAGCGCG |
| 25381 | TAGTACCTCA | CACCGTCCTG | CGGGTTGACG | TATGAGGCTT | GGATCCTCCC | GCTGCGCTGA |
| 25441 | GTCTTCAGCG | ATCCCCATCC | GCGACGTGCC | AACTAGGTCT | CCTCTCGTCG | TGAACAAGGC |
| 25501 | TACCGGGTTG | CAACTCCTGT | GCAACTCTCA | GGCTTCAACG | CGCTTCTACG | ACCTGCAATT |
| 25561 | TCTTTCCACT | TAGAGGATGC | AGCCGAGAGG | GGGTAAAAAC | CTATCTTGAC | CGGCCCATAT |
| 25621 | GTGGTCGGCA | GACACCCATT | CTTCCAAACT | AGCTACGCGG | GTTCGATTCC | CGTCGCCCGC |
| 25681 | TCCGCTGGTC | AGAGGGTGTT | TTCGCCCTCT | GGCCATTTTT | CTTTCCAGGG | GTCTGCAACT |
| 25741 | CTTGTGCGAC | TCTTCTGACC | TGGGCATACG | CGGTTGCAAC | GCATCCCTGA | TCTGGCTACT |
| 25801 | TTCGATGCTG | ACAAACGAAT | AGAGCCCCCC | GCCTGCGCGA | ACAGACGAGG | GGCATTCACA |
| 25861 | CCAGATTGGA | GCTGGTGCAG | TGAAGAGAAT | AGACCGGGAC | AAGGTTGCAC | CGGGAGTTGC |
| 25921 | AGCCGGTCGGA | ACCCTCGCCG | TCGGCGGGCT | GGCGTTCGCC | CTGTCGTTCA | CGGCTCTCAG |
| 25981 | CGAGCTGGCT | GCGGCCAACG | GGGTGGCCCA | AGCAGAGATG | GTGCCCTTGG | TGGTCGACGG |
| 26041 | CCTGACGCTC | GTCGCCACGG | TCGCCACAGT | GGCCCTCAAG | CAGAACAGTT | GGTACGCGTG |
| 26101 | GTCGCTGCTG | ATCCTGTCCA | CCGTCGTATC | GGTGGCCGGC | AACGTGGCAC | ACGCCTACCC |
| 26161 | CCACGGCATC | ATCGCGATGG | TGATCGCTGC | GATCCCTCCG | CTCTGGCTAC | TGGCGTCGAC |
| 26221 | CCACCTAACC | GTGATGCTGG | CGAAGCAGCA | CTCGGAGCAC | GCCGAAGTAC | CTGTCTCGCG |
| 26281 | GCCAGAACCC | GCGCCTCGGG | GCCTGGAGCC | CGCTGCCGCT | TGACTGCGCC | CGACCGGGAC |
| 26341 | AGAAATACAT | AGAGAACCTA | TGGATGTAGG | AGGCACAAAA | AAATACCCCC | CGAGCCAGCT |
| 26401 | CGAAGGCCAG | CCCAGGGGGC | ATGGTTCTGC | TTCAGTAGAC | CTTGCGAGTC | CGACCCGAGT |
| 26461 | TGATCATCGC | CATGATGACC | CAGACGGGCA | ACCACATTCC | GCAGGTGATG | AGCGAAAGCA |
| 26521 | ACAGGTGCAT | CGCGTGGTTC | GTCCTGACAG | GCATGACAGT | GGGCTGCGGC | ATCGGAGGAG |
| 26581 | GCGCGACCGG | GTACGGCGAG | CCCGCGTACC | ACTGAGGTCG | ATCTTGTTGG | GGCGGATACT |
| 26641 | GATTGGTCAT | CCCGACAGCC | TACTTGCCGA | TGGGTCGCAT | CAGCTCCTCG | ACCGACTCGC |
| 26701 | GCTCCACGCG | GATCAGCCGG | GGACCGAGCC | GAACGGCCTT | GAGCCGGCCG | TCGCGATGT |
| 26761 | AGTTGCGGAC | GGTCTTGGTG | CTGACACCGA | GGTAGTCAGC | GGTCTCCTGG | ATGGATGCTC |
| 26821 | TCGGGGGCAT | CAGCGCGGTC | CTCCGTGCTT | CATCGGTTGT | CTCCCGAACC | CTGGATCACG |
| 26881 | CCACGATCCT | TGCCGCTCTG | GAGCTTGTTG | AGGTTCCTCT | GGGTGACGGT | GCTCAACCAG |
| 26941 | ACATCGAGCT | GGTTGGCTAG | CTGGGCGACG | TACCACATCA | CGTCTCCGAG | TTCCGCCTGG |
| 27001 | AGGTCGTCTC | GGTTCTCCTG | GGTGATGACA | CCGTCTTTAT | CCCGGAGGAT | TTTCTTGACC |
| 27061 | TTGTTGGCGA | TCTCGCCGGC | TTCGCCTACG | AGACCCATCG | TCACGTAGGA | GAGACCCTCG |
| 27121 | ATGCTGTCGC | AGTCGCCTGC | ACCGGGGTAG | ATCGTCCTGC | CGCTCGCGGC | GATCTGGTAG |
| 27181 | ATGTCGACGT | GCATCAGATC | ATCACCGGGA | ACAACTGGCC | ACCGGGCATC | TGGATGAACA |
| 27241 | CCGGGACGCT | GGGGGTGTAG | TCCGACGAAC | CCGTGCCGCC | CTCACAGGCG | GACAGGCTCA |
| 27301 | GGGTGGCGGC | AAGGCCGATG | ATGGCTGCTG | CGATGGTCTT | CTTCATCTGT | TGCTCCAGTA |
| 27361 | GCTAAGTTCG | GACTCCAGTT | CGCGGATACG | CTCCTGTAGC | CCTTGGTTTT | CCAGGTACGC |
| 27421 | CTCGGCGAGG | TTGGCCTCCG | CGCGGTCACG | GGCCTCGTCC | TTCGACGTGG | CCTCATCGAT |
| 27481 | TGCCTCGTGT | AGCCGGCGGA | TCAGATCTGG | GATGGCACCG | TGCAGACCGC | ATATGAAGTC |
| 27541 | GGCGTCTGCC | TCGGAGAGGT | GGGACGCCAC | CAGATCCTTG | TCCTGGGTCT | CCTGGTTGAC |
| 27601 | CGCCCAGATG | ACGTGATCCT | CTAGCCCGTG | GTCGGTCTCG | CAGATAGAAG | GCGGTTCTAC |
| 27661 | CTCCTCTGGC | ATCCAGTAAG | TCTTCTCAGC | CCCGGTGGAC | TTCGCCCACT | GCTGGTGAGG |
| 27721 | GATGTCGAAG | AACTCGTGGT | CCTGTTCGTC | GGCGGTAATC | ACAGATCGTC | CTCTTCATCC |
| 27781 | CATTCGTCGT | AGTAACACGT | ACAGCCGCAG | CAGGTGCAGC | AGCCGCACTC | GTAGGTGCCG |
| 27841 | TAGTCGTAGT | CATCCCAGTC | GTCTTCGTCC | ATCTAGCTGT | ACTCCTTCAT | GATTCGGTCG |
| 27901 | AACGCACGCG | TCTGCACCGT | CATCTCCAGG | TCGACCGTTC | GCTTCAACCA | CGCCCATTCG |
| 27961 | CCGTCGTGGT | TGATCTCCCA | CTGGCTCTTG | AATGTCGCTG | TCTCAACGAG | GAACTCGACA |
| 28021 | GTCAACGTGT | GCAGTCCGTT | GTTGCTGGGC | TGGAATCCGA | TACCGTCCTC | AGCGATGTAC |
| 28081 | CAGGGCAACT | CCTGGCCGTC | GAAGTAGACG | GCCTTGTCGG | TCACCAGTAC | TTCAGGGAAG |
| 28141 | GTGTGCTCGG | TCAACGGCGT | CCCAGGTATG | GGATGACGCT | GGCCCGGAAC | TCAAGGAACA |
| 28201 | CCATGTTGTC | CGGGCAGTCC | TCGGGGACGT | TGTCGGGGCG | TTCGGCGGTG | TAGACGCCGA |
| 28261 | TCTCGTTGCC | CTCCAGGGTT | CCAAGCTCGT | TGAGCTTGTA | GATCGCCAGA | CCCATCAGCT |
| 28321 | CTTCATCGAG | ACCGTTCGGT | GCTGGCAGTA | CAACTTTGGC | TTGTGGCATT | AGCCCTCCCT |
| 28381 | CGGAATTACG | TATGCGCTGA | ACTCGACCGC | CGTAATGCCG | TCTGGCAGTT | GGAATCCGAA |
| 28441 | CCGCTCTTCG | AACTCCTCGT | TGGTGATGGG | GCCGTACTCG | AAGGTTCCGG | GCACTACCTC |
| 28501 | GCCCTCCCCC | TCGATCAGGA | GGTACGCACC | GGCGGCGTAC | ACCTCCTCGT | CGTTCGGCCA |
| 28561 | TCCGACTACG | GTCCCGAGGA | CCGTGAACTT | CCTCGGCTCC | ATCAGGGCAC | GTCCACTTCG |
| 28621 | TTGATGAGGA | ACCGCATCGG | AGGTGGAGTG | AGCATTGCCT | CGGCTATGGC | GATGAGGGCG |
| 28681 | TTCAACTGAC | CCTTCAGCAG | CTTCTCCTCG | TCGCCTGCGG | GAAGGTGGCG | CACTCGGCGC |
| 28741 | TCCATCTCCT | TGGCGCGTTC | CAGATATTCG | GTGGCTGTCA | AGTTGTCCTC | CTTAGTAATC |
| 28801 | AGCGCCGTAG | AGCGAACCCC | ACGAACGCTT | TCCGACCTCG | GGGTCGGTGC | CAACCAGCAC |
| 28861 | CGGACCCATC | TGTTCTTGCA | TCAGGTGGCC | AATGTGTGCA | GCGGCTCTCT | CAGCCTCTGA |
| 28921 | GGCGGGCAGA | GACGCGACGA | TCTCGTCGTG | GATAGGCAAC | CGTAGGTACG | GGGTGTATCC |
| 28981 | GGCCTCGTGG | AGGCGAATCA | GAGCCCGACA | GGTCACGTCC | CGCGACGACG | ACTGGATCAT |
| 29041 | GTAGTTCAGC | GCGGAGTATG | TCCGCGAGCT | GTCCACCGGC | AGCCGCCGGC | CCATCGCGTT |
| 29101 | GACGATGTAG | CCGTTGCGGC | CAGCTTCCAT | CGCCAGCTTC | TTGCTCAGCC | GCTCCACACC |
| 29161 | GGGGTATGTC | GCAGAGAACG | CCTCATGAAC | TCGCTTGGCC | ACAGGGATCG | AGATCCCAC |
| 29221 | TGCCTCAGCG | AGAGCCTTCG | CCCCACCGCC | GTAGACCTTC | TGAAAGTTGG | CGGTCTTCCC |
| 29281 | AACCTTTCGC | GGCACCTGGG | CTGCGTCAGC | GGTCATCTGG | TGGAGGTCCG | CACCGTTCTC |
| 29341 | GAATGCCTCG | ATCATGTTGC | GGTCGCCCGA | CAGCGCCGAC | AGGACGCGAA | GCTCCTCGGC |
| 29401 | CTGGTAGTCG | ACTGAGGCCA | TCACATCGCC | TGGCTCAGCG | ATGAAGCATC | GCCGCACGAT |
| 29461 | CCAGTCCGAC | GACGGCAGCG | TCTGCGCCGG | GATGCCGGTG | ATCGACATGC | GCGAGGTCCG |
| 29521 | CGCCTGCAGT | GGGTTGATGA | ACGTGTGGCA | GCGGTCCTCA | GAGTCCCTGG | TGTCGATGAA |
| 29581 | CTTCTGGACC | CAGGTCTTCC | GCCACTTCCC | CAGCTTCTTA | GCCTCCTGAG | CGATGGCGGC |
| 29641 | AAGCTCGTTG | CCATCTTCGA | CCAGCTTGTC | GAGCAGAGCC | GCGTTGACCT | GGCGCTTGCC |

-continued

SEQ ID NO: 1

| | | | | | |
|---|---|---|---|---|---|
| 29701 | AGTCTCGGTG | CGACCGGTGA | TCTTGACGCC | CATCTCCTCA | AGCCCCTCGG | CCAGATCCTC |
| 29761 | GGTCGAGTTG | ACCTTCTCCA | CGCCGTACTC | GGTGAAAGCG | ATTGCCTACC | AGACCTCCTG |
| 29821 | ATCGGCCAAC | CACTTCTCGG | CGAGCGACCG | CGAGTACTCC | ACATCGAGCA | GGAAGCCCTG |
| 29881 | CCTGTCGATG | TAGCTGCAGA | TCTCACTGAT | CTTGTGCTCG | TACGGCACCA | GCGACCGACT |
| 29941 | CACGTCGGGC | ACCAACGGTG | TCAGGCTCTT | GCAGACCCTC | GCGGTGAAGA | TCGTGTCCAT |
| 30001 | CCCGGCGTAC | AGCAGGTACT | CCGGGTGGAA | CAGGTCGATG | GTCGACCAGA | TCTTGGCCTT |
| 30061 | GGTCGTCTTG | TGCTCGGCCG | CTAGCTTGGC | CATGAGCTTG | TTGACGTTCT | CGGCCTGGTC |
| 30121 | CTCGGAGATG | AACTTCGCGA | TCAGCTCTTC | GAGCGAGTGC | CCGAACCCGC | CGGCCTCGAA |
| 30181 | GGGCCGGGGG | TCCACCAGCT | TCGCCAGGAT | CTGCCGTGTCA | AGCACGCGGG | GCCACAGACC |
| 30241 | CTCCATCTCG | ATCCCGAAGC | ACTGGTCGAG | CACCTGGAGG | TCGAAGGAGG | CGTTCTGGAG |
| 30301 | CACCATGCGC | TTGAGACGCG | CGATGGCGAT | CCGCACGTCC | TCGATGAACA | CGTCTCCCAG |
| 30361 | CTCCACCGGC | ACCACCCAGG | CTTCGYCCTG | AGTACCGAAC | TGGACGAGGC | GGCACTCGAA |
| 30421 | GGTGTCGCTG | TAGATGTCCA | GCCCGGTGGT | CTCAGTGTCG | ACGGCGAGGC | AGTTCAGGTG |
| 30481 | AGCCCGGATG | AAGTTGCGGA | AGCCTTCCAG | ATCCTCTGGG | GTTTCAACGA | CGTTGACGGT |
| 30541 | GACGAGGTCT | CCCTGAACCT | CATGCCGCAG | CACCTCGATCAAA | ATGCTCTCCT | ACTGGAAGTA |
| 30601 | CTGAGGCGGA | ATCCAGGTGG | CTGAGGCCAT | CTCCTTGATG | GCCTGCTGCA | TGGCCGCTTC |
| 30661 | GAACGGACAG | TCCGGGTCGA | TGTCCGGCTT | GTAATGGGTG | ACGATGATCC | GGCTGTTGCC |
| 30721 | GCCGAAGTCG | TGGCTGACCA | AGCCCTTTGG | GGGCAGCTTC | TTCAGCGCCT | TGATCAGTTC |
| 30781 | CTCAACCGTG | GTCCCGGTAG | GGGCCTTGCC | GTCAGGCAAT | GCCTCCCCTC | CGTACGGCAC |
| 30841 | GTCCAATGGG | ATCGTGTACC | GCTCAACGTC | TTTGATCTTC | ATCGAGCCTC | TTCCTCTTCG |
| 30901 | ACTACCTCGT | CTACCCGGCG | GAATAACTCC | GCTAGTTCTG | CGGGTAGCAA | TACTGGGTAC |
| 30961 | TTCTCTCGGG | CTTCCTGCAT | CGCTACCGCG | ATCCCAATCA | GGGCAGCGAG | CAGTTCATTG |
| 31021 | ACGGAGTACG | CCAACAGCTC | TTCGCGGATC | TCTTCTCGGG | TCATTAGTGG | TAGATCCCCC |
| 31081 | GGACGGTGCG | CCGAGATCGTG | GCAGGGTTCA | CGCCGTAGTT | CTCGGCGAGA | TCCTTCTGCT |
| 31141 | TCATACCGCC | CAGGTACGCC | TGGCGGATGT | CCTTGACCTC | GCGCTCGGTG | AGCTTCTTGC |
| 31201 | GGTTCGCCCG | GCTCGGGCCG | GTCTCAGGCT | TGACCTGAGC | CAGCGCCTTG | CCGAACAGCT |
| 31261 | CGTTCTGCGT | CCGCTGCTTG | ATCGCGTACC | GACGGTTCGC | TGCAAGCACC | TCGTTGAGCC |
| 31321 | GCTGGACAA | CTTGACATTG | GCCTCACGCA | CTACCTCGAC | CTCTCCGAGC | AAGTTCGTGA |
| 31381 | TCCGGTAGTC | CTTGTCCTGG | TTCTCGATGG | CCAACCGGTT | GTTCTCCTCG | GAAAGCATCG |
| 31441 | AGACCTTGTA | TTGCGCCTCT | CCCAGCGCAG | CTTTCAGGTG | CTTCTTCCTC | ATTCAGCGCC |
| 31501 | CCTCTCTCGG | CGGAACTGTT | CGTACTCGTC | TTCGTCATG | TAGTAGTAGT | AGTCAACGAC |
| 31561 | CTTGTCCCAAG | TTGAAGGTTC | GGGACGTGCC | GTCATCGACA | GCGATGATCA | GGACACCCTC |
| 31621 | TTGGGTGTCT | AGGATCGGCT | CGCCAGCCAC | GACGTGGAAG | CGGTCCTCGA | GGGTCACCGC |
| 31681 | AGTCGCTCTG | CGTGCCATGT | CAGTTCCTCT | CAGTAGCTGT | AGGGGACATC | CGGGATGTCC |
| 31741 | TGGTAGGTGT | TGGGTGCGAT | CTGTCGGAGC | TGCCGAAGCA | ATTCCCTGC | CAGCTCACGG |
| 31801 | ATCTCGGCAT | CCGCGGCCTC | GTGCCAGCGG | GCCTTGATGA | CGTACCGCCA | CGCCCGATGG |
| 31861 | TTGCCCGTGA | CGACCATCGG | TGAGTTCGTC | ATGTTCGGCA | GGACAGCTCG | CGCTGCCTCG |
| 31921 | CGGGCCTGCT | TGCGCGGCAA | GCCCCGGTCA | GCCAGCCGGT | TGACGATGTG | TTCGTAGACA |
| 31981 | GCGTCAATCT | CAGAGCTGAC | GGACTCCATG | ATGTGGACGA | GGTCGTCTCG | GTCGTCGGGG |
| 32041 | TGGAGCTTGA | ACAGAGCCGG | GGGCAGATGG | ATGCCAAGGT | CGGTCGGATC | CACATATCGC |
| 32101 | TGAGACACCA | CCGAGAAGCT | CAAGTGACGG | TGACGCTCCA | GCTCGGTCAG | CACCGACCTG |
| 32161 | CTGGCCTCGA | TGTAGAACGT | CGCCGAGGCG | TGCTCGAACA | CGCTCTCGTG | GCCCAGATCG |
| 32221 | ATGATGTGGT | TGAGGTAGTC | CTCGTTCTCG | GCAGTTGCCG | GGTTCGGTCG | GTGGAACGAC |
| 32281 | CGGTAGCAGT | TCCGGCCCGC | GAACTCGGCC | AGCTCGTCGG | CATCGAAGTC | GCCGAAGTAG |
| 32341 | GGATCTTCGT | CCTTGGATTC | TTCGAAGTCA | TCGACCTCGA | ATCCGATGTC | CCGCAACGCA |
| 32401 | CCCGGATCGA | TCTCGGTGGC | AGCGATCAGT | TTGGCTTTCA | TACTCTCCGC | TCAGAGTTGG |
| 32461 | TGGAACGAGG | TCAGCCAGGG | GGCAGCGAAG | CCCTTCTACA | GCTCCCCTTG | GCTCGTTACC |
| 32521 | GGCTTCTCGA | CCTCGGTGGA | TGTCAAGTAG | TCGAGATGAC | TACTTCTTGT | CGGGCCATTG |
| 32581 | CGCGTCACAC | TGCTGATCGC | GAGGTGCGGT | GCAGGAGAAC | AGCGCGTACG | GCTTGCCCGT |
| 32641 | CTTCTTCGAG | ACGCCCGACT | TGTAGACCAT | CTCGCCGTGC | TGGCAGTACC | GCTTCTCGCC |
| 32701 | ACCAGGCGCT | TCCTGAGCTG | CCTGCGGGGC | GCGAGACTGC | TGCTGGCCAC | CGCCGCCGCC |
| 32761 | GTTGGCCGGC | GCGGATCCAC | CGGAGCCTGC | GTAGTGGCCT | GCGATCTGCT | GGACCTTGTC |
| 32821 | CATCAGCGCC | TTGAACTCGG | CGGTGTTGAC | CTTGGCCAGC | ACGTCGGCCG | GGTCCGCACC |
| 32881 | CTTCACGACC | ACCCACGGGT | CGCTGTACTG | ACCGGCGAAC | TTGAACGTGG | CCGACACCCC |
| 32941 | ATCGGTGGAG | TGCTGGACCG | CCATCGAGTC | GCGCACAGCA | GCCGAGGCCG | TCGTCACCGT |
| 33001 | CGCCGACGGC | GCGGTCTCAG | GCTCAGGGCG | TCGGGCTGGG | TCGGGCTGGG | CAGGGGCGGT |
| 33061 | GCTCCACGGA | TCGTCGTAGG | ACAACTGGTT | ACCTTTCACT | TAATGGGGCA | TGCGCCGTTG |
| 33121 | GCGCACTCTT | CATCGACACC | GTCTTCGACG | GCTTTGGCCG | CAGCAGATTC | GTACTGCTGC |
| 33181 | TTGGTGATTC | GCTCGTACGG | AGCCTGCGGG | AAGCTGGACT | CCGGGAAGAT | CGTGGAGCCC |
| 33241 | TTGATGAGCC | CCGCGAACCT | CTTGAGATCG | GCTGCGACAT | CCTCGGCGTCT | GTAGGCGTCT |
| 33301 | GGATGGACGT | TGGCGGTGAA | CGACACCGCG | TTGTCAGCCC | AGCACATCTG | GTAGAGCGCC |
| 33361 | TGGAACGCCA | GGAGCTGGTG | GAGGGTCAAC | TCGTCGGCTG | ACTCAACGAT | CTCCTCGTCC |
| 33421 | CAACCGAGTT | CCTCGACAGC | CTGGACCAAC | GTGTCCTTGG | TCGGGATCGA | AACCACCTCG |
| 33481 | GTGTTCGGAG | CGAAGAGATC | CTTCTCGATC | TCGTAACCCT | CGGCTGCCAA | CCTCCGCAGC |
| 33541 | TCGGCCATGT | CGCTGTTGAG | GTTGAACCGC | ACACGCCGGA | TGAAGTACCG | CGAGAAGATC |
| 33601 | GGGTGGATCC | CCTCGGAGAC | TCCTGGCATC | TTCGCCACCG | TGCCTGTGGG | AGCGATGGTT |
| 33661 | CGCTTCTTCA | CCGGGACAGG | GATCCTCAGA | TCATGGGCGA | ACCGTTCGGC | CTCTGAGTCG |
| 33721 | ACCTCAGCGG | CCATCTCCCG | CAAGAACTGG | GTGAACCGCT | TATCTCCGGG | TGCCTCGGAG |
| 33781 | TACCTGCTAC | CTGTGAGGGC | CAAATAGGAG | GCAACTCCGA | GATGACCCAC | GCCGATGCGA |
| 33841 | CGGTTTCGGT | CCAGAACCTC | CCGGCTCTTC | GGGTCGGCCA | CTTCCGAGAA | CGTCGCCCGG |
| 33901 | ATCAGGAATC | TCGTCATCAG | ACGATGCGCC | CGGATCAGGT | CGAGGTAGTC | GGTCTTGCCG |
| 33961 | GCCGGCGTCA | CGAACGCCGC | CAGGTTGATG | TGGCCGGAGGT | TGCACGGCTC | CCACGGTTCG |
| 34021 | AGAGTGATCT | CGCCGCATGG | GTTGGTGCAG | ACCACCCGGT | TGGGCTCACC | GACGTTGGAC |
| 34081 | AGTGACGAGT | CCCACATCCC | CGGCTCTCCG | TTGCGTACGG | CTCCCTCGGA | GAGTGCCTTG |
| 34141 | AGCACTCGGT | GGGCTCGCTT | CTGCTTGGGC | ATGTCCTCGC | GGGCGACCGC | GAAGCTGCCG |
| 34201 | TAGCCCTCCT | TGGCCAGACG | CCAGAACTCG | TCGTCAACCT | CGACCGAGAT | GTTCGTCGTC |
| 34261 | CAGTGCTCGC | CCGTGCTCGC | CTTGATGTTG | ATGAACTTGT | CGATCTGGTA | GTCGTCCCAG |
| 34321 | TGCATCATCG | ACATCCGCGC | CGACCGGCGC | ACACCGCCGG | CCACAACACA | CTGAGCGATG |

-continued

SEQ ID NO: 1

| | | | | | |
|---|---|---|---|---|---|
| 34381 | GCGTGGTCGA | CCTCCATCGC | GGCGATGCCG | TCGAGCGTGA | TCCCTGCGTA | CTCCGAGAAG |
| 34441 | ATGTTGGCGA | CCTTCTGCAG | CATCACAGCG | AACGGCAGCG | GGCCGCTGGC | CACTCCACCG |
| 34501 | AACGTCTTGA | GCTTGGCCCT | TTGCGGCCGG | ATGCGGCTCA | CGTCGTACAC | CCGCTGGTAG |
| 34561 | TGGACCGTGC | CGGGTCGGTA | GTGCGTGTCG | ATCAGATCGA | CCAGCGCAGC | AGCCCAGCCC |
| 34621 | TCTCGTGAGT | CCTCGATGGC | GTAGGCACCG | GCCCAGTCGT | GGCTGTAGTG | CTCCGACAGA |
| 34681 | ATGCCTACAT | CCTTCATCGC | CTGGTAGTCG | ACATGCTCTG | GATCACAGAC | GATCTCGACC |
| 34741 | CGCAGGGGGT | TTACGACCTC | GGGGTAGCCT | TCGAGGTAGT | GGTTCGAGTA | GTTCGCCCCG |
| 34801 | ACTCCCCCGC | CCTCCATCAG | GCGCATGAAC | GTGAACTGGA | AGTGGTCCGA | GATCTTCTCG |
| 34861 | GGCCAGCCAG | CTACCCAGCA | GTTGAAGAGG | TGCTGCGCGT | TCTTGACCCC | CGAGGCCCAC |
| 34921 | AGATGCCGAC | CTGCCGGCAG | CACCTTGAAC | TTGGTCATCA | GACGAACGAG | ATCTTCTCGC |
| 34981 | TCTCCTTCCA | ACATATGTCG | CCGGTCGACA | AGAGCAAGAT | TGCCGTCCAC | GACCCTCTCG |
| 35041 | ACCGTTTCCG | GCCAGGTTTC | CTTCGAGCCG | TCAGGCTTGG | TCCTGGCGTA | GGTTCGGTTG |
| 35101 | TAAACGAGTT | CACCGGTTGG | TCCCCAAGGG | ATTTCGTCAG | TCAACTACTT | CCTCTCAGTC |
| 35161 | AGTTCGTATC | GCTTGAAATA | GGCGTCGGCA | GAGTCGCCGC | CAGAGAACGA | GAAAAAGTAC |
| 35221 | TCGACCGGGC | CTGCACCACG | CACCTCGCAG | GTAACGACGC | CCTTCCTTCC | CCGGAACATC |
| 35281 | GGCCAGGTTC | CCTTGGAGGG | GTGCTTGGTC | TCGTCCCGCT | GGACGATGAC | CTTGGTGCCC |
| 35341 | TTCTTCATGC | CGACTTCCGT | TCTCCGTAGC | CGGGAGTGAA | GCAACCCCCG | ACGTACAGCT |
| 35401 | CGAGATCTTC | TTGCGACCAG | TTCTCCAGTC | GCATCGGCGG | CTGGTGCGGG | AACAGCTCCG |
| 35461 | GGAACACCTC | GGCCCGGTAC | AGCTCCGAAC | CGGGCATCCC | GTTGAACGTC | GGATCAAGAA |
| 35521 | TGTTGTGCAT | GGCACCTCCC | TCCCAAGAAC | TCGGAGATCG | GCGGCTCGTA | GAGGTAGCCA |
| 35581 | TCGCGCAGCT | CGGGGTTCTC | GATGAGCATG | ATCGCGATGT | TCGCTGTGGG | GTCAGAGTGC |
| 35641 | CCATCCCCCT | GCGACTTTCG | GATGTCTGGG | AAGATAGCGT | GCTTGCTGCC | CGGACCATCC |
| 35701 | TTGACGATGA | CCTTGCCCTT | GTCGTCCTTC | TCCACGCCAG | CCGTGATCGC | GATGATGTTG |
| 35761 | ACGTGCTCGG | TCAGCGACTT | GTGAGCGCGG | AACAACGAT | TCTGCCCGCT | CTTATCCTTC |
| 35821 | GGGGAGATCC | CGTCGGTGTA | GCGGCTCCTG | ATCGCCTCTG | CATAGCCCCC | GTTCTGAGCG |
| 35881 | TCCAGAGCCT | TCATCGCCAG | CGGGAGGATG | TCGACCAGGT | ACCGATTGGT | CGACTCCCCC |
| 35941 | TGCAGAGCCT | CTTTGACGTT | CTCGGACGAG | TAGTGGCTGC | GCTCCTGGAA | CAAGTCGCGG |
| 36001 | GCCTTGGCCG | CTCCCGACAG | GATGTTGCGA | ACCTGATTGC | GTACGTAGTG | AACTGCCTCA |
| 36061 | CCACGGTGCA | AGCTCTCCAG | CGTCTTCTGG | ATGTACGGGC | TCTCGAGGTA | CCAGACCCAC |
| 36121 | AGCTCTTGGA | TGATCTCCTC | GGCTGTCAGG | TTGGTCTCCC | AACCGATCAG | CGCCTTCCGG |
| 36181 | GTGGCCCTGC | TGAACAGCTT | GCTGATGTCG | TCGGTCAAGG | CATCACCTTT | CGTAGGTACT |
| 36241 | CCTCCCGGTC | CAATCGGCGG | TCGAGGTGTC | GAGTGACCTC | CTCCGCGAAG | ACCTCGCGGA |
| 36301 | CTTCGCTGGA | GGTGATCTGG | CGCGAACGTG | CGTTCTTGTG | CAGGTACGGC | AGCTTGGTGG |
| 36361 | CTGTCAAGTT | CTAGACCTCC | CAGACTCGGC | CGTCGACCGA | GAACCGGCCT | CCGACAATCG |
| 36421 | GAACAAGCTC | AGGCTTGACG | TGCTGGCCGT | CGACCGTCAG | CAGAGCAAAA | CCACTCTGCC |
| 36481 | AGTTGGCTGT | TGCACCCTTG | AGGTACTGAG | CTAGCTTCAT | GTTCATCAGG | TTGCCGACCT |
| 36541 | CCATCGACCA | CAGCACCTTC | TGGTTGCCGC | CGTAGCCCAG | CGTGTGTGGC | TTGATGCCCT |
| 36601 | GGCGGTGGGT | GTGTCCGATG | ATCACCGACG | TGCCGAACCG | CATCATCGCG | TTGTACGCGG |
| 36661 | TGTCAGCGGA | CTTCTGCGTC | ACCCGGACCC | CACCACGGTG | GCCGTGGGTG | GAGATCCAGC |
| 36721 | CTGGAGCGAT | CTTGTAGAAC | TCAGGCAGCA | CGTCAACACC | GAACCCGTCG | AAGTCCAGCA |
| 36781 | GGTTCTGGAA | CTGGAACGAG | CTGACGTACT | CGACCGACGC | CGGGGCGAAC | TGGTGCAGGT |
| 36841 | AGTCGACTGG | CCGGCGGTCG | TGGTTGCCCT | CGTGGACACC | AACCGGCCG | TCGTAGACCT |
| 36901 | GGCGCAGCGG | CTCCAGGAAC | CGCCGCTTGC | ACTGCTCGGA | GTCGGGCTTG | ATCCGCTGAG |
| 36961 | CGAACTCTTC | CTTGGTGCCC | TTGGTCCACC | GAGACGGGCT | CGGGTAGTCC | ATCAGGTCAC |
| 37021 | CGATGTGGAC | GACCTCGTCA | GGCTGGGTGT | CCCCAGATCA | GCCGATGACC | GCCTTCAACT |
| 37081 | GCTTGCGATC | ATCGAACGGA | ATCTGGGTGT | CCGAGATGAC | GACGATGCGC | TTGCTCACTC |
| 37141 | AGCGACCTCG | GTGAAGGGGC | CCCGCATACG | TTCCTCGTGG | GAGCTGGCGT | TGCCTCCTGA |
| 37201 | CCAGCGTCGC | TTGCCCACCT | TGGTGTGGTG | CAAACCCGTTG | GGGTAGTAGA | TCCACTTCAC |
| 37261 | TCCTGTGACG | TTGGTGACGG | TCTTCACATC | GGCAGGAACG | TCCAGCAAGG | TGTCCCACTG |
| 37321 | GCGAGGCCCC | TTGGGATACC | GCTCGTCCTC | GGGGAGCTGC | ATCTTCTCCA | GAACGCCTGC |
| 37381 | GTAACCGGCG | ATGTCGACCA | CCGTGTCCTG | GTGGTAGCCG | TTCTCCATGA | ACCGGGCGAT |
| 37441 | CTTCAGCAGG | ATCATCATGA | CGGCCACGTC | CTCCGGGGTG | AACTCGACGC | CGCGCTTGTA |
| 37501 | CGCGCCCCAC | AGGGTCGCGA | TGCGTTCGTG | GTTCTCCTTG | GCGTCCCCGT | AGTCCTGGGC |
| 37561 | TCGCTGTCCG | TTGATGATCT | CTTCGGCGGT | GGTCAGAATG | CTCACAGTCC | AGTCTCCGAT |
| 37621 | GCGGTGTAGT | AGTCGATCAG | CTCATCGAGC | TGGTCCGGTT | GATAGCCGAG | GATCGGCTTG |
| 37681 | TGGGTGTCAG | TGACGACGAC | GGGAACCGAC | ATCGCGTTGA | GCACCTTGGT | GACGTAGTCG |
| 37741 | TACGCCTCCG | AGTTGGCCGT | GACATCGACT | GCGTCGAAGT | CGATCCCGGC | AGCCGTCAGC |
| 37801 | TTGTCTTTGA | CTCGCTCGCA | TGGCTTGCAG | CCGGGACGGG | TGTACACCGT | GACCGGCGCG |
| 37861 | AACAGCGTTC | TCACGTGAGC | ACCATCCCAG | TCGATGTATC | GGTCTCCATA | CATCAGATCC |
| 37921 | TTTCCAGCAG | AGCAGCTTTG | CCCTGCGATG | TGACTAGTGA | GTTGACATCC | TCGCCTTCTG |
| 37981 | GCATCGGGAT | GATTCGGGCG | TTCGGCAGCG | TCTTCGCCAC | CGACCGGGCG | AACTCCATAC |
| 38041 | CGGCGTCGTC | GCCGTCGGCC | AGGATGTTCA | CGTTGCGGTA | GCCCAGGAAC | AGCTCTCGGA |
| 38101 | AGTACGGCTT | CCACTTCTGG | GCTCCGCTGA | GCCCCACCGT | CGGCAGCCCA | CACAGCTCGG |
| 38161 | CGGTGATCGT | GTCGAGTTCT | CCCTCGCAGA | TCGCCATGTC | CTTGCTGTAT | TTGGTCAGCG |
| 38221 | CGTAGGTGTT | GTAGAGCCGG | TCCTTCTCCC | CTGGCATCGA | CAGGTACTTC | GGTGTCCCAC |
| 38281 | CGTCGATTCG | GCGATACCGG | ATCGCAGCTA | CCGTCCAGTG | ACGCCAGGGC | GACCACCGCA |
| 38341 | TATACGGAAT | CGCCAGGCAG | CCCCGGTACA | TCTCATGTCC | AGGGAGTGGG | TCGTCCACGA |
| 38401 | ATCCCAGACC | GAACCGGCTT | AGTTCCGCTC | GGCCGGCCAG | CCCGCGACTC | GCCAAATACT |
| 38461 | CGTCGGCTGG | GCTTCCGGGC | AGGCTTTCTC | TGTACCGGGA | CGTTGCCTCC | CACAGATAGG |
| 38521 | TTCTCTGCGA | TTCGCTTAGC | CTCTGCAAAT | GTCACCTCCT | CTTCGTGACG | AATGATCGAG |
| 38581 | ATCACGTCTC | CACGGACCCC | GCAGGCCATG | CAGTTGTAGC | CCTGTAGGTC | GTAACTGACT |
| 38641 | GCGGCAGACG | GCGTTTCGTC | GCCGTGGAAG | GGGCACAGGC | ACTTGTTCCA | CTCGTGGTGG |
| 38701 | TCAGGTGGTG | GTTCCCAATC | CGGGTGGTAG | CGAAGAATCG | CCCTCGCGAT | GGGCGAGTCG |
| 38761 | TTCATTCGTC | CTCGTCAAGC | TCCTCGGGAG | AGAGCCCTTC | GAAGATCCCG | TTCAGACAGG |
| 38821 | CGGCGAAGCC | CTCGCCGGTC | TCCGCTGCGT | CGAGCATCTC | TGCAATCGTC | TTTGCCATGT |
| 38881 | TTCCTCCTGG | TGGATGTCAA | GTTCGAGACA | GCTTGTCAGC | CTCGACTGGA | GCGATGCGCT |
| 38941 | CCCCGATGAC | TTGGACGGCC | GGCGGGTTCA | GCAGGTACTC | GATGGCCCGT | TTGAAGAACT |
| 39001 | CGATGCAGTC | CCTCGCCCAG | CCCAGCGTGT | ACTTGTTGCA | CATCGTGCAG | AGCAACCCTC |

SEQ ID NO: 1

```
39061  GGACGATGCC  TGTCTTGTGA  TCGTGGTCGA  CCGACAGGCG  CTTCTTCTTA  CCGTTGGCTC
39121  GCTGGCAGAT  GTAGCACCGA  CCACCTTGGA  ACTCGTAGAT  CTGCCAATAC  TCATCGCCGG
39181  TGATGCCGTA  GGTGGCCAGG  ATCCGGGTCT  CCCAGCTCGT  AGAGCTGCGA  GCCGTCCTGA
39241  ACTCTCGGTG  ATGAGTAGCG  CATCGTGGCC  CTGGATACTT  GGCGTCTCGC  GTGAGCGGGA
39301  GCCCTGTGC   GACACAGTCT  TTGCAAGGCT  TCCGCTTGTG  CTTACGGTTC  TGCACCCGGT
39361  ACCCCGGAGA  CCTCTTCGCC  GCCCTCGGCA  CGCGCGTCCT  CCTCCCGGTT  CTCCATCACC
39421  ATGCAGAACC  ACGACAGCAG  CCCTGCCAGG  GAGATGTAGA  AGGCCACCAG  AACTTGGCCG
39481  CTCACTTCAC  CATTCCTCGA  ACCCACCAGC  GAGACAGCGC  CTTACGCCCT  TTGTCGAGCG
39541  GGGTCAGCTC  GCGCTCATCG  TCCTCACCGA  AGTCGAACTC  GATGCTGGCG  ATCTCGTAGC
39601  CGAGGATCTT  GAACGACACG  TTCATAGGCG  GTCTCCGAAG  TTGATGACGG  GAATGCCGGC
39661  CTTCCAGATC  CGAGATCCGG  TGATCAGTAC  TCGCCGCATC  AGATCGCCTC  CCACTGCCGG
40021  CCGTCGTGCG  ACGTGACCAG  CTCCGCTTCG  TAGACGCCGT  AGCGGGTGGC  CAGGAACTGG
40081  ATCATCTGCG  CCTGCTTGTA  CCCGAAGGGA  CATTCGTGGA  CGCCGCTGAT  CGGGTATCTG
40141  ACTCCGTATT  TCACTTGATC  CACCGCTTCG  CGATTCGGTC  GACGTTCTCC  TCGGAGACGT
40201  TGCGGGCGAG  GCCGGTGAAC  TCCTGGCCGT  GGACCTTGGT  CTCGATCACG  CGAGGCTTGC
40261  GGGGATCCGG  GCTCTCCGGG  TCGATCCGCT  TGTGGGTCCA  GACGGTCGGC  TTCGTCTTGA
40321  TCAGAGCGCC  CAGCACCTGC  TGGCGCAGTG  GGTTGGTCTT  GCGGGGCATA  GCGTTTGGAG
40381  TGGTCATCTG  GATCCTTTCC  TCGGTGGCTG  TCAAGTCGGT  GTGCGTAGTG  AAGCCCCCCC
40441  AGGCATGCGC  GCCCCGCCTG  GGGAGAGTTG  ATCAGCGCAG  ATCGATGTCG  GGCAGGATCG
40501  CCTGCGGCTT  GAAGTTGACC  TGGTAGAAGT  CGGTCGAGAC  GTTTGCGCCA  TCGACCTGCT
40561  CCATGAAGTA  GGAGACGTTG  TCCGACAGGC  CCAGGAAGTG  CTTCTTGATC  CCGTCCTTGG
40621  TCTTGCAGGT  CACGTCGAGC  TTCTTCGACG  CGGTGTCCGC  GTTGATTGAG  CACCGGCCCT
40681  GGATCTCGAG  CAGGTACTTG  TCCGTGATCC  CGTTGAAGAA  CACGATCCGG  CGATTGATCT
40741  CGAAGTTGTC  AGCGGCCTTG  CTGACGTTCT  CCCATGCGAC  GTCGGCGTCG  GAGGTACACG
40801  CGGAGAGGCC  CAGGATCGCC  GATCCGGCGA  TGAGTGCGGT  GGCGATGATC  TTCTTCATGT
40861  TCGCTACTTT  CTGTTTGGTG  GATGTCAAGT  TAGTGACCGA  AGTCGTTGAT  CTGCATAGTG
40921  TCTCCGACGA  ACTCCAAGGA  AGCGAAGTCT  TGTCCCGACG  GGTCCGACTT  CCCCCCTCGG
40981  TTCTTGACCG  TGGAGACGTT  GAGCATGTCC  GGGCCGAACC  CGTCCGATAC  TCGGTGGAGA
41041  GTGAGGATCA  TCTCAGGAAC  ACGCCCGATC  TGACCTTTGA  TGCCCGACAA  CGGGATCGGC
41101  TTGTCGCCGT  CGTTGTGCGG  GCCGGTGACG  TGGTGGAGCC  CGACGACGCA  TGAGCCTGTC
41161  TCACGGCCCA  TCTCGTGTAG  GTAGTCCATC  AGCGACTCCA  GACCCGACGAA CGGGTCGTCT
41221  CCCTCGCTTG  AATCGGTGCG  GACGTTGGTG  ATGTTGTCCA  CGACGATCAA  CGCTGGGAAG
41281  TCCTCGTACA  GCGCGTCATA  CGCGGCCAGA  GCGTTCTCGA  TCTCGTCCAA  CGACGGTGAT
41341  GCCTTGTAGT  TGAACCGGAT  CGGGATCTCG  TCTAGTGAGT  CAGCTACCGC  GTCCTCGATG
41401  TTCTGCTCGC  GAACAGCCCG  CGTAGCTCGT  TCGAGCGACC  ATCCGCTGAG  GATGGACACC
41461  GAACGGGAGA  GCTGGGTGAA  CGCATCAGAG  TCGGCCGAGA  AGTACAACGT  CGGCACCTTC
41521  GACTTGAGCG  CGTAGGCGAG  GACGAACGCC  GACTTCCCGG  TGCCGGGGCC  GGCGACGACC
41581  AGGACTAGCT  GGCCTCGTCG  GAGATGTGTA  CCTTTCTGGT  CAAGCGCGGC  CCAGACCGGG
41641  GGTAGCGGAT  CCCCCGCCGA  CCCTCGGATG  TAGAGCGATT  GTCTAGGTGT  GTACACCTTC
41701  CTCCTCGTCG  ATGTGATTGA  CCAGGTCATA  GATCTCGTCG  GAGAGACCA   GCCGGCCCCA
41761  GGCGTCGATC  CCCACGTGGA  TCTGTCTCCG  GTGGATGTGT  CGGGACAGGA  TCATCGGCGA
41821  ATGCGTGTGC  CCGTGGATCA  GGATCTTGCC  ATCGTCACGG  AGCCTCCACT  GGGTGTGTCG
41881  GTCCTCGCTG  GTGTGGTCCC  CGACGTATGG  GAAGTGGCTC  AGCAGAACAT  CTGTGTGCCC
41941  GCCAGCGTCC  CCGTACAGCG  GCACCCGGAT  ACGAGCTGCC  GTCGACACAT  GCTCGAACAC
42001  CATCCAGTAC  GCACCAACCA  GCTTGTGAGC  ATCGCGGTTC  ATCGGGTGGG  GCCCATCGTG
42061  GTTGCCCAGG  ATCAGCCGTT  TGCGGCCTGG  CCGATCCGAG  ATCCACCCGA  GGGCATGTAT
42121  CTGCCCCTTG  GTGGAGCCAG  AGGAGATGTC  ACCTAGGATC  CAGACCGTGT  CGTCCTTGCC
42181  GACGACCGAG  TCCCACGCCT  TCGCCAGGGT  GGCGTCGTGC  TCTTCGACAT  CATCCGCCAG
42241  GTTGCGGATC  TCCATCAGCC  GCTTGTGTCC  GATGTGTAGA  TCGGACGTGA  ACCAGGTGTT
42301  GCTCATGGCT  TCCTTTCAGA  ACGGCGGGCC  GTACAGCTCG  ATCACCAGCG  CGTGCAGCTC
42361  CTCTGCCGCG  TCGTCACGCT  CGAATCCGCA  GCAGGAATCG  TGCCGGTCGA  GGATTGCGAC
42421  GATCTGGTCG  TAGAGGCTGG  GCCTCACTTC  ACCTTCTTCG  GATCGATCAA  GGCGTCGTGA
42481  ATCGGCCGAC  CGGCGCGAGC  CGCGTGCGTC  TCGGCGTCCA  AGGCTCGCTG  CATCTGGTTC
42541  ATCAGCCGGG  TGCCGCGCAG  CTTGAGGATC  TTCATGGTCG  CCCGACCCTT  GTATCCAGCG
42601  CGGTGCATCC  GTAGGACGCA  GGCTGTCTCG  TGCGGGCTA   TAGGTGACCT  CAGCGACGGG
42661  TGGTTTGGAT  CCCAGTTCGT  CATGTCTTCC  TCTCGGTGGC  TGTCAAGTTG  GTCACAGACC
42721  GAACTCTTCC  TGGTACTGCG  GGATGAAGTG  GCCGGCCGTT  CATGTTCGGC  TCGATACCTC
42781  TCGCGTCACG  AACTCCTGCC  CGTTCCATCT  CCGACCGTCC  TCGAACTCGA  TCACGATCTC
42841  TCGTCCGGGA  TGACGCACGG  CCTCCGCTTG  GGCAAACCTG  CGTGCAGCCT  CTGGGGTCGG
42901  GAACGGAAAC  TTCTGCGAGG  CGTACAGCTC  CTGGTGCCAC  TTCGGCTTGT  CAGGAATCGG
42961  CCCCATTTCC  ACGTACGTGT  AACCCGCGTC  GGGGTCGAGT  TCGAGCGTTT  TCTTGTATTC
43021  CTTCGTGCCT  GCCTTAGAGG  GAAGGTGAGT  ATCGGTGGCT  GTCAAGGTGA  CCTCACTTAA
43081  AAACAGGGCA  GCTGTAATTC  ACATCACAGA  AGCCGCATTT  GTCAGGTTCA  GGCAGAGGCT
43141  CGAAGTCACC  AGCCTGGATC  CGAGCCTCGA  CCTCATGGAA  CCTCTCGGTG  ATCCGCTCCC
43201  GCGTCCAATC  GGTCAGGTCG  TAGGGCGCAG  TGGGCTTCGC  CTTGATGCCC  TTCTTCCCCG
43261  CCATGAAGTA  GTCGCCCGTC  TTCGGAGCCT  CCACGTCATA  GGTCATCGCG  ACCGCGAGCG
43321  CGTACACGCC  GAGCTGGAAG  TCGTCACCCG  GCGAGTTGCC  GGTCTTGTAG  TCCCGGACTC
43381  GAAGCTCACC  GTTGACCACG  ACGACCGCAT  CGATGAACCC  TCGGACGCGG  ATGCCGTCCA
43441  GCTCGATGTT  GAACGGAAGC  TCGATGGCCG  GCTTGGGCTG  TTCACACTCC  TTGCAGTTGG
43501  TGTCTTTCCA  CGCCTCCGTA  GAGCAGATCC  CTCGCCAGG   GGTAGTCCAG  ATCTGCTGGC
43561  CCTTGTCCTT  CCGCCACGCG  ATGAACTTCT  CTACCTGCTC  CAGTCCAAGG  TGGAACCGGC
43621  GCTCGATGTC  ACGCTCACCG  TTGTACGGCC  CGGACCAAAA  CCACCACTCG  AAGTTCGGGG
43681  TTTCGTCGCA  CAGTGCTCCG  ATGTCCTTGG  CGTACTCCTC  GCGGAAGATC  TCTTGTGCCC
43741  GTTCGAGGCT  CATCTCGCGG  CCCTCGGCCA  GAGCCTTCTC  GTAGACCTCA  GCGACGGTGT
43801  GAAACGCGGT  GCCCTGCGGC  AACCACGCCG  CAGGACGAGC  CCATACCTTG  TCGATGCGAG
43861  CCAGCTTGTA  CGCCTGCGGG  CAACGTGTGT  ATTGGTTCAA  CTGGCTGACG  CTTCGCAGCG
43921  GCAGCAATGT  CTTGGTGTCT  GTCACGCAGC  GGCCATCCTT  CCCTTGCCTA  TCGTCTCGTT
43981  CAGCGCCCCG  TCGACAGCGA  CACTGAGCAG  TTTTGCGACC  TCCGACATGT  CAATCGGATC
```

-continued

SEQ ID NO: 1

| 44041 | CTTGGGGAAT | TGGTCAGCCT | GAGTCATCCT | GAGCACCATC | CACTCGGTGC | CCTTGTCGCA |
| 44101 | GTGGATCATG | GTCGGATCCT | TAATTAAGAT | CCTTTAGTGA | GGGTTAATTG | CGGCCGCGAA |
| 44161 | TTCTTGAAGA | CGAAAGGGCC | TCGTGATACG | CCTATTTTA | TAGGTTAATG | TCATGATAAT |
| 44221 | AATGGTTTCT | TAGACGTCAG | GTGGCACTTT | TCGGGGAAAT | GTGCGCGGAA | CCCCTATTTG |
| 44281 | TTTATTTTTC | TAAATACATT | CAAATATGTA | TCCGCTCATG | AGACAATAAC | CCTGATAAAT |
| 44341 | GCTTCAATAA | TATTGAAAAA | GGAAGAGTAT | GAGTATTCAA | CATTTCCGTG | TCGCCCTTAT |
| 44401 | TCCCTTTTTT | GCGGCATTTT | GCCTTCCTGT | TTTTGCTCAC | CCAGAAACGC | TGGTGAAAGT |
| 44461 | AAAAGATGCT | GAAGATCAGT | TGGGTGCACG | AGTGGGTTAC | ATCGAACTGG | ATCTCAACAG |
| 44521 | CGGTAAGATC | CTTGAGAGTT | TTCGCCCCGA | AGAACGTTTT | CCAATGATGA | GCACTTTTAA |
| 44581 | AGTTCTGCTA | TGTGGCGCGG | TATTATCCCG | TGTTGACGCC | GGGCAAGAGC | AACTCGGTCG |
| 44641 | CCGCATACAC | TATTCTCAGA | ATGACTTGGT | TGAGTACTCA | CCAGTCACAG | AAAAGCATCT |
| 44701 | TACGGATGGC | ATGACAGTAA | GAGAATTATG | CAGTGCTGCC | ATAACCATGA | GTGATAACAC |
| 44761 | TGCGGCCAAC | TTACTTCTGA | CAACGATCGG | AGGACCGAAG | GAGCTAACCG | CTTTTTTGCA |
| 44821 | CAACATGGGG | GATCATGTAA | CTCGCCTTGA | TCGTTGGGAA | CCGGAGCTGA | ATGAAGCCAT |
| 44881 | ACCAAACGAC | GAGCGTGACA | CCACGATGCC | TGCAGCAATG | GCAACAACGT | TGCGCAAACT |
| 44941 | ATTAACTGGC | GAACTACTTA | CTCTAGCTTC | CCGGCAACAA | TTAATAGACT | GGATGGAGGC |
| 45001 | GGATAAAGTT | GCAGGACCAC | TTCTGCGCTC | GGCCCTTCCG | GCTGGCTGGT | TTATTGCTGA |
| 45061 | TAAATCTGGA | GCCGGTGAGC | GTGGGTCTCG | CGGTATCATT | GCAGCACTGG | GGCCAGATGG |
| 45121 | TAAGCCCTCC | CGTATCGTAG | TTATCTACAC | GACGGGGAGT | CAGGCAACTA | TGGATGAACG |
| 45181 | AAATAGACAG | ATCGCTGAGA | TAGGTGCCTC | ACTGATTAAG | CATTGGTAAC | TGTCAGACCA |
| 45241 | AGTTTACTCA | TATATACTTT | AGATTGATTT | AAAACTTCAT | TTTTAATTTA | AAAGGATCTA |
| 45301 | GGTGAAGATC | CTTTTTGATA | ATCTCATGAC | CAAAATCCCT | TAACGTGAGT | TTTCGTTCCA |
| 45361 | CTGAGCGTCA | GACCCCTTAA | TAAGATGATC | TTCTTGAGAT | CGTTTTGGTC | TGCGCGTAAT |
| 45421 | CTCTTGCTCT | GAAAACGAAA | AAACCGCCTT | GCAGGGCGGT | TTTTCGAAGG | TTCTCTGAGC |
| 45481 | TACCAACTCT | TTGAACCGAG | GTAACTGGCT | TGGAGGAGCG | CAGTCACCAA | AACTTGTCCT |
| 45541 | TTCAGTTTAG | CCTTAACCGG | CGCATGACTT | CAAGACTAAC | TCCTCTAAAT | CAATTACCAG |
| 45601 | TGGCTGCTGC | CAGTGGTGCT | TTTGCATGTC | TTTCCGGGTT | GGACTCAAGA | CGATAGTTAC |
| 45661 | CGGATAAGGC | GCAGCGGTCG | GACTGAACGG | GGGGTTCGTG | CATACAGTCC | AGCTTGGAGC |
| 45721 | GAACTGCCTA | CCCGGAACTG | AGTGTCAGGC | GTGGAATGAG | ACAAACGCGG | CCATAACAGC |
| 45781 | GGAATGACAC | CGGTAAACCG | AAAGGCAGGA | ACAGGAGAGC | GCACGAGGGA | GCCGCCAGGG |
| 45841 | GGAAACGCCT | GGTATCTTTA | TAGTCCTGTC | GGGTTTCGCC | ACCACTGATT | TGAGCGTCAG |
| 45901 | ATTTCGTGAT | GCTTGTCAGG | GGGGCGGAGC | CTATGGAAAA | ACGGCTTTGC | CGCGGCCCTC |
| 45961 | TCACTTCCCT | GTTAAGTATC | TTCCTGGCAT | CTTCCAGGAA | ATCTCCGCCC | CGTTCGTAAG |
| 46021 | CCATTTCCGC | TCGCCGCAGT | CGAACGACCG | AGCGTAGCGA | GTCAGTGAGC | GAGGAAGCGG |
| 46081 | AATATATCCT | GTATCACATA | TTCTGCTGAC | GCACCGGTGC | AGCCTTTTTT | CTCCTGCCAC |
| 46141 | ATGAAGCACT | TCACTGACAC | CCTCATCAGT | GCCAACATAG | TAAGCCAGTA | TACACTCCGC |
| 46201 | TAGCGCTGAG | GTCTGCCTCG | TGAAGAAGGT | GTTGCTGACT | CATACCAGGC | CTGAATCGCC |
| 46261 | CCATCATCCA | GCCAGAAAGT | GAGGGAGCCA | CGGTTGATGA | GAGCTTTGTT | GTAGGTGGAC |
| 46321 | CAGTTGGTGA | TTTTGAACTT | TTGCTTTGCC | ACGGAACGGT | CTGCGTTGTC | GGGAAGATGC |
| 46381 | GTGATCTGAT | CCTTCAACTC | AGCAAAAGTT | CGATTTATTC | AACAAAGCCA | CCGAACGCCA |
| 46441 | GCAAGACGTA | GCCCAGCGCG | TCGGCCGCCA | TGCCGGCGAT | AATGGCCTGC | TTCTCGCCGA |
| 46501 | AACGTTTGGT | GGCGGGACCA | GTGACGAAGG | CTTGAGCGAG | GGCGTGGAAG | ATTCCGAATA |
| 46561 | CCGCAAGCGA | CAGGCCGATC | ATCGTCGCGC | TCCAGCGAAA | GGGGTCCTCG | CCGAAAATGA |
| 46621 | CCCAGAGCGC | TGCCGGCACC | TGTCCTACGA | GTTGCATGAT | AAAGAAGACA | GTCATAAGTG |
| 46681 | CGGCGACGAT | AGTCATGCCC | CGCGCCCACC | GGAAGGAGCT | GACTGGGTTG | AAGGCTCTCA |
| 46741 | AGGGCATCGG | TCGAGGAACT | TTCGGCGGCT | TTGCTGTGCG | ACAGGCTCAC | GTCTAAAAGG |
| 46801 | AAATAAATCA | TGGGTCATAA | AAATTATCAC | GTTGTCGGCG | CGGCGACGGA | TGTTCTGTAT |
| 46861 | GCGCTGTTTT | CCGTTGGCCG | TTGCTGTCTG | GTGATCTGCC | TTCTAAATCT | GCACAGCCGA |
| 46921 | ATTGCGCGAG | CTTGGTTTTG | CTGAAACCGA | CACACAGCAA | CTGAATACCA | GAAAGAAAAT |
| 46981 | CACTTTGCCT | TTCTGACATC | AGAAGGGCAG | AAATTTGCCG | TTGAACACCT | GGTCAATACG |
| 47041 | CGTTTTGGTG | AGCAGCAATA | TTGCGCTTCG | ATGAGCCTTG | GCGTTGAGAT | TGATACCTCT |
| 47101 | GCTGCACAAA | AGGCAATCGA | CCGAGCTGGA | CCAGCGCATT | CGTGACACCG | TCTCCTTCGA |
| 47161 | ACTTATTCGC | AATGGAGTGT | CATTCATCAA | GGACNGACTG | ATCGCAAATG | GTGCTATCCA |
| 47221 | CGCAGCGGCA | ATCGAAAACC | CTCAGCCGGT | GACCAATATC | TACAACATCA | GCCTTGGTAT |
| 47281 | CCTGCGTGAT | GAGCCAGCGC | AGAACAAGGT | AACCGTCAGT | GCCGATAAGT | TCAAAGTTAA |
| 47341 | ACCTGGTGTT | GATACCAACA | TTGAAACGTT | GATCGAAAAC | GCGCTGAAAA | ACGCTGCTGA |
| 47401 | ATGTGCGGCG | CTGGATGTCA | CAAAGCAAAT | GGCACGACAA | AAGAAAGCGA | TGGATGAACT |
| 47461 | GGCTTCCTAT | GTCCGCACGG | CCATCATGAT | GGAATGTTTC | CCCGGTGGTG | TTATCTGGCA |
| 47521 | GCAGTGCCGT | CGATAGTATG | CAATTGATAA | TTATTATCAT | TTGCGGGTCC | TTTCCGGCGA |
| 47581 | TCCGCCTTGT | TACGGGGCGG | CGACCTCGCG | GGTTTTCGCT | ATTTATGAAA | ATTTTCCGGT |
| 47641 | TTAAGGGCTT | TCCGTTCTTC | TTCGTCATAA | CTTAATGTTT | TTATTTAAAA | TACCCTCTGA |
| 47701 | AAAGAAAGGA | AACGACAGGT | GCTGAAAGCG | AGCTTTTTGG | CCTCTGTCGT | TTCCTTTCTC |
| 47761 | TGTTTTTGTC | CGTGGAATGA | ACAATGGAAG | TCAACAAAAA | GCAGAGCTTA | TCGATGATAA |
| 47821 | GCGGTCAAAC | ATGAGAATTC | GCGGCCGCAT | AATACGACTC | ACTATAGGGA | TCTTAATTAA |
| 47881 | GGCGCTTGAT | CAGGATCAGG | TCGATGGCTT | TGTTGTTCTC | CGGGCAGCGC | ACCGCCGTCG |
| 47941 | GAAACTCGGC | CTTGCCTTTG | GCGAACGTGG | TGTCGACGTA | GGCGATGTTG | ATGCCCTTGT |
| 48001 | CTTCCAAGAA | GCGCGCCACG | TCGATGTTGT | CCGGGTCTGC | GCTGAAGTAC | AGCGCCAGGT |
| 48061 | TGTCGAGCCT | CTGCGAGTGC | AGGTAGACAG | CCGCCGTCTG | AACCCTTGTG | TAGGCCCAGA |
| 48121 | ACTGGACATC | CGGGTTGTCG | CGGATGACTC | GACCCAAGC | GGCCACATAG | GTGGGGCTGA |
| 48181 | AGAAGTCTCC | ATCCCAGTGG | ATGCGGAACA | GCTTCGGAGC | CTTGCGACGG | TCGCAATCCT |
| 48241 | TGACGAACTC | GGCGACCATC | TCGGACAGCA | GCGTCACGGT | GTCTGTCAAG | TCAGCGTCAC |
| 48301 | GCAACAGTTC | CCAGTTGTGC | AGCAGGACCG | AGCTGACAGC | CTTGCGAACT | TTCTCCAGCT |
| 48361 | TGCCGGCGTA | GCACACCTTG | GCACAGAAGG | CCGTCGCGTC | CGGGCAGGAG | AAGCCTTGAC |
| 48421 | CGGAGGGCAG | GCCGATGCTG | TTGGCGATAC | CTACGGTGAC | GTTGCCGCCG | TGGTGACGT |
| 48481 | GGACGTAGTT | GGTGACCTTG | CGGTCGTTCG | AACGCTTCAG | CTTGCCCATA | CCTAGCCTTC |
| 48541 | CTTCGGTGGC | TGTCAAGTTG | TTGGATACAA | AGCGCCCGA | GAGGGAGTCG | AACCCTCACA |
| 48601 | CCGCGAACCG | TCGCGGGCC | ACCGTGCCTA | GTCGATAGAG | GTCACTCGAC | TCTCGTGGAC |
| 48661 | GTAGACCACG | GTGTTGCCTA | CGTTCACCGC | GTAGTACAGG | CCATCGGCAC | CTCGTAGCTT |

-continued

SEQ ID NO: 1

| | | | | | |
|---|---|---|---|---|---|
| 48721 | GTGCCGAACC | GTGCCCGACG | TGGCCGTCAT | GTCTTCGCCC | CAGTCGGCGT | TAGGTGCCCA |
| 48781 | GGTGACTCGC | ATGGTGATCC | CTTCAGTAGT | CGGTGGCTGT | CAAGTCAGCG | GATACGGACG |
| 48841 | TACCCGTTGC | CTCGAGCGAC | GTAGATCTTG | CCGTCGATGT | AAACGCGCTG | CTGCTGGTTC |
| 48901 | ATAATCCTAT | TCCTTTCGGT | GGCTGTCAAG | TCTCAGGCCC | AGCGACGAGT | CGTCGGCCGG |
| 48961 | GGGCGGCGCA | CCTTGGGCGC | GTTGGCTCGC | GGTGCCTTAC | GGATGGCGGT | GCCTACCGTG |
| 49081 | TTGTAATCGA | AGTCAGTCCA | CCCCTTCAGA | CCCTTCTCCA | GCTCGCGATC | CAACAGACGC |
| 49141 | GGAGCCGACA | GCTCAGGCGC | AACAAACGGT | GTCTTGACGC | TCTCGCGGGC | AGTAACCCGA |
| 49201 | ACCTCACGGT | GCTCAGCGAA | GACTGGCATA | GTTCACCCCT | TTGGTGGATG | TCAAGCCTGA |
| 49261 | GCACCAAAGC | TCAGGCGTAG | TGGGTAGTCG | GGAATCGAAC | CCGATAGCTT | CATAGCCACG |
| 49321 | TTCTACGGCT | CAGCCATAGC | TCAGCGATCA | TTCCATCGCG | CCAAGAGCTA | CCCTCCCGAA |
| 49381 | TGCCGAACCA | AAGCTCAGCA | TTCGTAAGTG | TGTATTCTCC | CCGTGGCTCA | GACAGTATCT |
| 49441 | ATCAGAACCT | AACCACAGGT | CTACATTTAG | TTATCCGCAG | TGCTCGCACT | TTAACGGCAT |
| 49501 | CGAGCTTCCG | CCGACCCTCA | GTCCTCTGGC | AGCGAACTAA | AGGTTTGAGT | CGGGCTGCGG |
| 49561 | CCCTTCTCGG | TCTTGCGTGA | TTCTCACTCT | ACCGGATGTT | TCGGTGGCTG | TCAAGCGGGC |
| 49621 | CGTTTTGGTG | TTGCAACGAT | GCCCTCGTTT | AGCGCCGCTG | GCGTAATGCG | CTACCCGCCT |
| 49681 | GATCTCACCG | GTCCAAGTTG | GTGATGCTTG | CAGCTTACCC | GATAACCGGG | TGGCTGTCAA |
| 49741 | ACCGGACAAT | CTTGCCGCCG | GATTTTCACC | GGCACCGGCA | CGATCCTCTC | GGATCCGCCT |
| 49801 | ACCGCCTTGC | TGCTGCGGTG | ACACAAGAAT | GCACTACTGG | CCGGGTGGCT | GTCAAGCCCT |
| 49861 | AATCGCAAAT | TGGTGCCCTA | GCTGCAGATA | TGGCGCGTTC | TCGGTGGCTG | TAAAGGGCAC |
| 49921 | TACGTGCCGC | TATCCGCTGG | TCACGCTGGA | CAGTCCCGGC | AGCCCGTGCC | GCGCATAGGC |
| 49981 | TGCTCACTAC | GTGCCCGGTA | TCGGCGTTGT | CGTGCCGCTG | TCGTGGTCGT | CGCCCCGTCG |
| 50041 | CTGTCGCTGG | TCTCGGTGGC | ATCGCTTGAC | AGTCGCCCCG | CTATCCCCCG | TTGCCGCTGG |
| 50101 | TCAGACGCTA | ATCCGCTTAT | TTCGCATAGG | CTGCTCACTA | TCGCATCGGT | ATGCGTATGC |
| 50161 | GCTGGTCACA | TATGCGTGTG | GTGGTGGTGT | GGTGTGCGTG | TGTTTGCGCT | GGTCAGCCGT |
| 50221 | GTGCGTACCG | TATCCGCACA | CTGTGCTTGT | GCGTTTGCTG | TGTGTCGAGG | CCGGCTCTCG |
| 50281 | CATCGTCGCA | TGTCAGCGCG | GGTATGGGCG | TGTATCGCAC | GCTTTGCTAG | CCGCGTGCCG |
| 50341 | C | | | | | |

EXAMPLE 3

Construction of L5 polymerase complementing M. smegmatis strains mc²889 and mc²890

Transposon delivery shuttle phasmids should not be able to replicate in the recipient strain to which the transposon is to be delivered. However, in order to maintain and propagate the shuttle phasmid, a conditional host in which this vector will be able to replicate should be available. In the case of phAE41 pol or phAE42 pol, this host should be one from which a high titer phage lysate can be obtained. Therefore, a trans-complementing derivative of M. smegmatis mc²155 carrying the L5 polymerase gene integrated in its chromosome was constructed. phAE41 was cleaved with PvuII and SacII and 7620 bp fragment containing the pol gene, was agarose purified and subsequently cleaved with AsuII. Cleavage with the AsuII produced a 2211 bp internal DNA fragment containing the intact pol-gene. As a cloning vector, an integration proficient expression vector pMV361 was used (see Stover et al., Nature, Vol. 351, pp. 456–460 (1991)). The cloning vector was digested with ClaI, dephosphorylated and subsequently transformed in E. coli DH5α from Bethesda Research Laboratories. Kanamycin resistant colonies were screened for the presence and orientation of pol gene downstream from the hsp 60 promoter. An E. coli clone was selected. Plasmid DNA was isolated and electroporated into M. smegmatis mc²155. Two types of kanamycin resistant colonies were isolated: small and large. The small colonies were designated mc²889, and the large colonies were designated mc²890.

EXAMPLE 4

Construction of int attP xis (phAE42) and pol (phAE45) deletion mutants of L5 shuttle phasmid phAE41

Since the entire sequence of the L5 genome is known the entire sequence of the shuttle phasmid phAE41 was deduced after determining the exact site of insertion. As discussed above, restriction analysis allowed for the determination of the site of insertion.

L5 shuttle phasmids have several advantages over L5 phages. Specifically, they are stable constructs for which the sequences can easily be deduced. In addition, they can be manipulated as cosmids in E. coli. These properties allow for easy manipulation of the L5 genome. Manipulation of the L5 genome of phAE41 shuttle phasmid was performed in order to produce shuttle phasmids phAE42 and phAE45, as described below.

In order to generate transposon delivery vectors, it is necessary that the delivery phage not be able to replicate in the recipient cell. Therefore, a derivative of phAE41 which was devoid of the integration functions of L5 was constructed. This construct was achieved by recombining a previously characterized mutant of L5, L5cd31 (see Donelly-Wu, et al., Molec. Microbiol., Vol. 7, pp. 407–417 (1993)), that contained a deletion of the region containing integration functions. In order to achieve this, the L5cd31 mutant and phAE41 were both cleaved with XbaI, an enzyme that cleaves each molecule twice. The XbaI-Fragment containing the deletion of L5cd31 was isolated and ligated to the purified arm containing E. coli cosmid of phAE41. These two fragments were ligated together and packaged into bacteriophage lambda heads. The resulting transducing particles were transduced into E. coli, and clones conferring ampicillin-resistance were identified. Two different orientations of the L5cd31 fragment were found in analyzed E. coli recombinants. The fragment in the correct orientation was capable of producing plaques following transfection of M. smegmatis mc²155 cells. Restriction analysis confirmed that phAE41 had acquired the deletion of L5cd31, thus generating shuttle phasmid phAE42, to which the integration genes had been deleted. Shuttle phasmid phAE42 was deposited with the American Type Culture Collection, Rockville, Md., on May 20, 1994 and catalogued as ATCC No. 69625. This demonstrates that novel L5 shuttle phasmid derivatives can easily be constructed by common cloning methodologies and cosmid technologies known to those skilled in the art, which methods employ packaging in vitro techniques.

It was then determined whether specific genes are essential for the propagation of the L5 mycobacteriophage. The first gene studied was the polymerase (pol) gene of mycobacteriophage L5. A deletion of this gene was constructed in order to determine whether it is essential for replication of the L5 phage in *M. smegmatis*. To achieve this, the 7.6 kb PvuII-SacII fragment containing the pol gene of L5 was cloned into a pKS Blueskript derivative vector. An internal deletion of the pol gene was then generated with by cleaving this molecule with CleI. This removed 290 bp of the pol gene. The 7.3 kb PvuII-SacII L5 fragment containing the pol deletion was then mixed with the other purified PvuII-SacII fragments of phAE41, ligated, in vitro packaged, and in transduced in *E. coli* selecting for ampicillin-resistant colonies. Plasmids were isolated and characterized by restriction analysis and one out of 20 was found to have the full complement of the phAE41 parent, except that the 7.6 PvuII-SacII fragment had been replaced with the 7.3 kb deleted PvuII-SacII fragment. One such mutant was denoted phAE45, which was deposited with the American Type Culture Collection, Rockville, Md., on May 20, 1994, and catalogued as ATCC No. 69628. This demonstrates that specific deletion can be readily incorporated into specific genes of L5 and that the genome of the resulting phasmid can be readily amplified for subsequent analyses in *M. smegmatis* and other mycobacteria. In addition, transfection of 1 μg of phAE45 DNA isolated from *E. coli* yielded no plaques following transfection of $mc^2155$ cells. In contrast, transfection of $mc^2155$ cells with 1 μg phAE41 DNA yielded 2800 plaques. This inability of phAE45 to form plaques on $mc^2155$ establishes that the L5 pol gene is essential for L5 propagation.

EXAMPLE 5
Construction of L5 Luciferase Shuttle Phasmids phAE43 and phAE44

Figure 5:
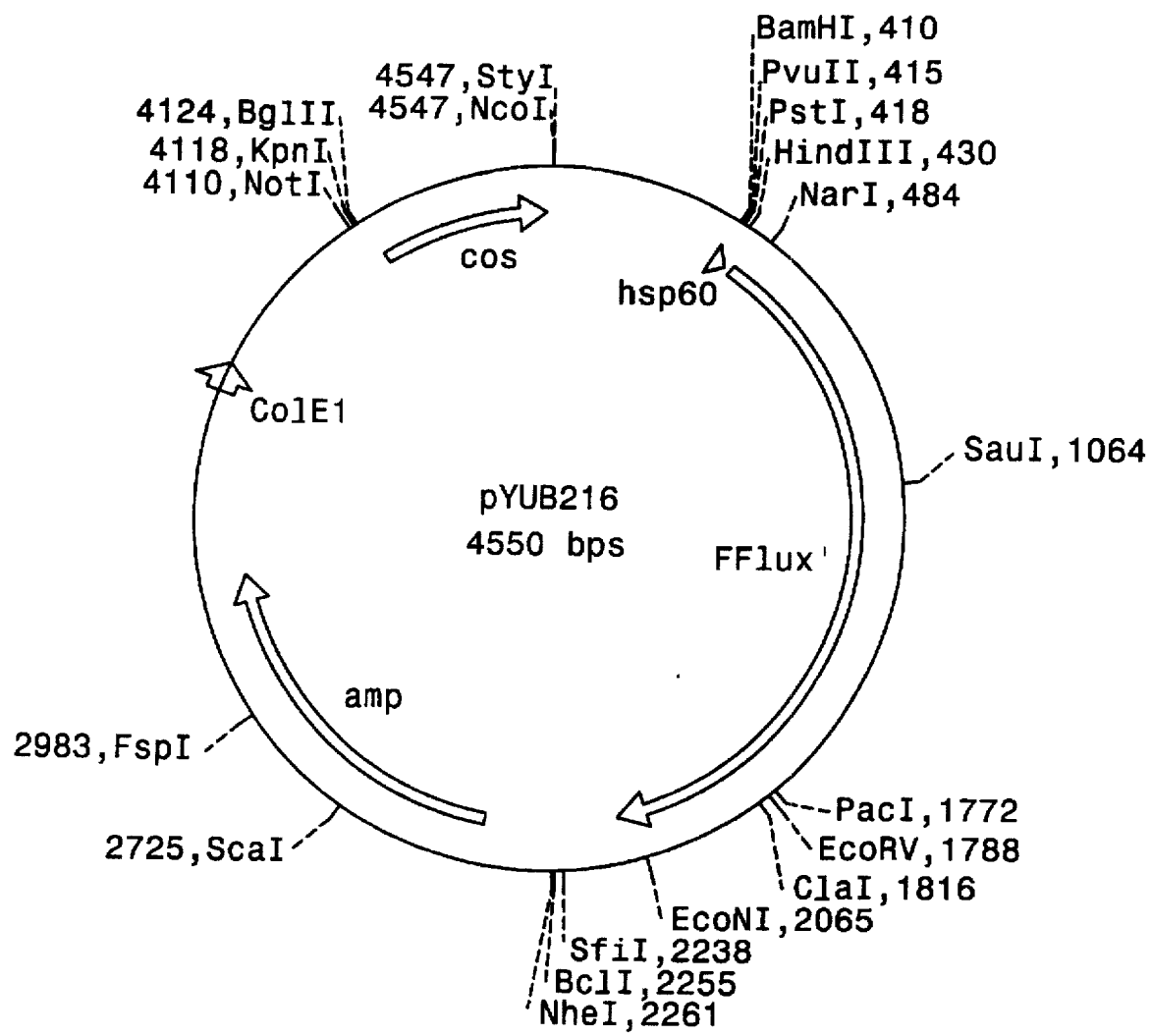
FIG. 5 represents the cosmid pYUB216 which contains the firefly luciferase gene fused to the hsp60 promoter of BCG.
Figure 6:
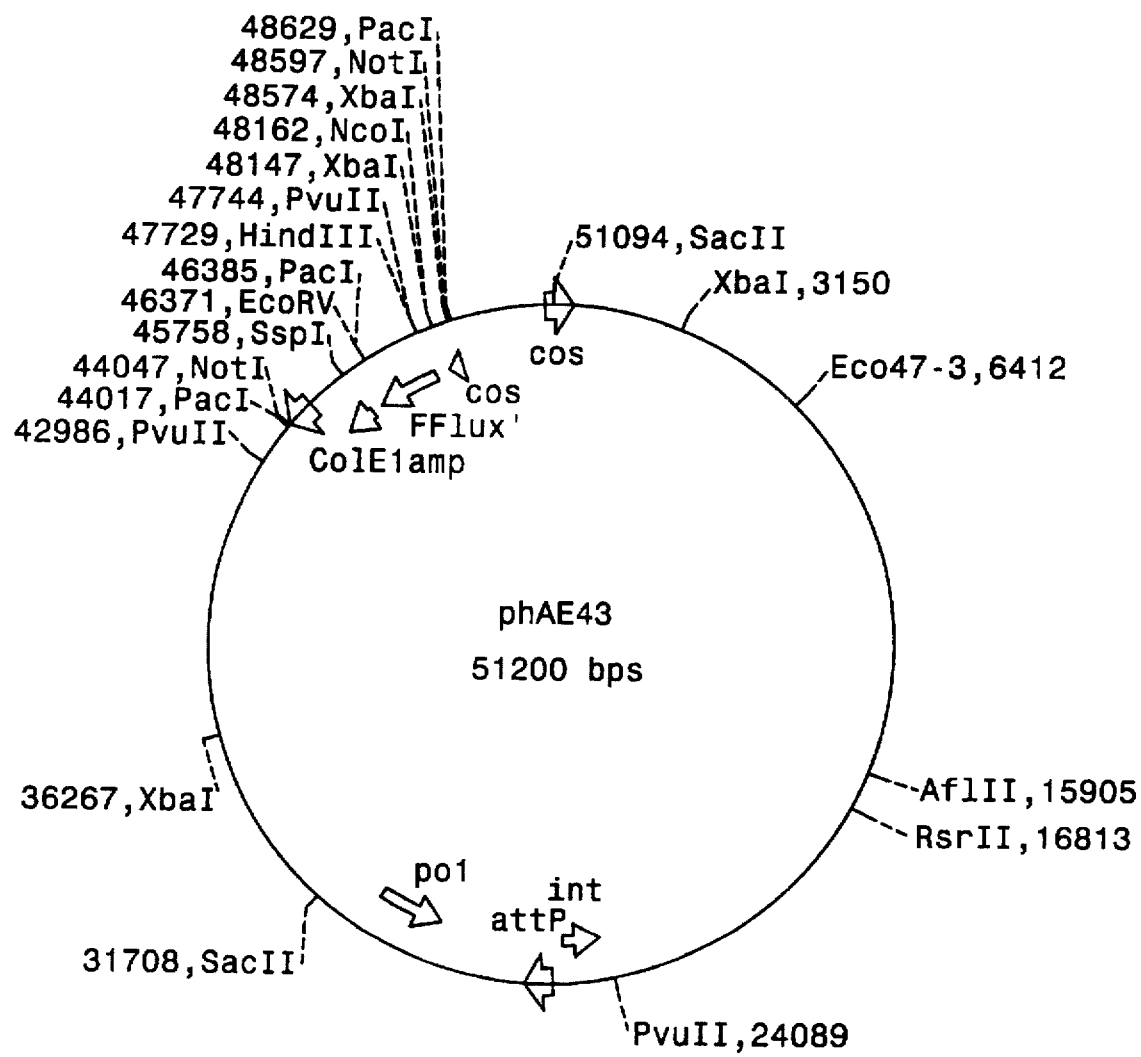
FIG. 6 represents the L5 luciferase shuttle phasmid phAE43 in which cosmid pYUB216 was inserted to replace pYUB328 in phAE41.

PacI, NotI and EcoRI sites flanking the unique BamH1 restriction site of pYUB328 were incorporated into L5 shuttle phasmids. Since L5 does not contain PacI, NotI or EcoRI sites, L5 shuttle phasmids can be cleaved with any of these enzymes in order to release virtually the entire pYUB328 cosmid. This facilitates the incorporation of any new cosmid into the L5 backbone. In order to demonstrate this, phAE41 and phAE42 were cleaved with NotI, and the L5 sequences were isolated away from the cosmid portion of these shuttle phasmids. A ligation was set up between the isolated NotI fragment of phAE41 containing the L5 sequences and pYUB216 (see FIG. 5) by the method described by Jacobs, et al., *Science*, Vol. 260, pp. 819–822 (1993). The resulting ligation was in vitro packaged into *E. coli* and ampicillin-resistant colonies were selected for. The resulting cosmid molecules were screened. It was found that pYUB216 had been introduced into both orientations into the NotI backbone of phAE41. Transfection of the set of 4 different phAE41 and phAE42 derivative plasmids revealed that only those cosmids in which the Hsp60 promoter was in the same orientation as the leftward promoter of L5 yielded plaques. A single plaque derived from phAE41, which was designated phAE43 (see FIG. 6), was deposited in with the American Type Culture Collection, Rockville, Md., on May 20, 1994 and catalogued as ATCC No. 69626. A single plaque derived from phAE42, which was designated phAE44, was deposited with the American Type Culture Collection, Rockville, Md., on May 20, 1994 and catalogued as ATCC No. 69627. Both phAE43 and phAE44 were then characterized.

Figure 7:
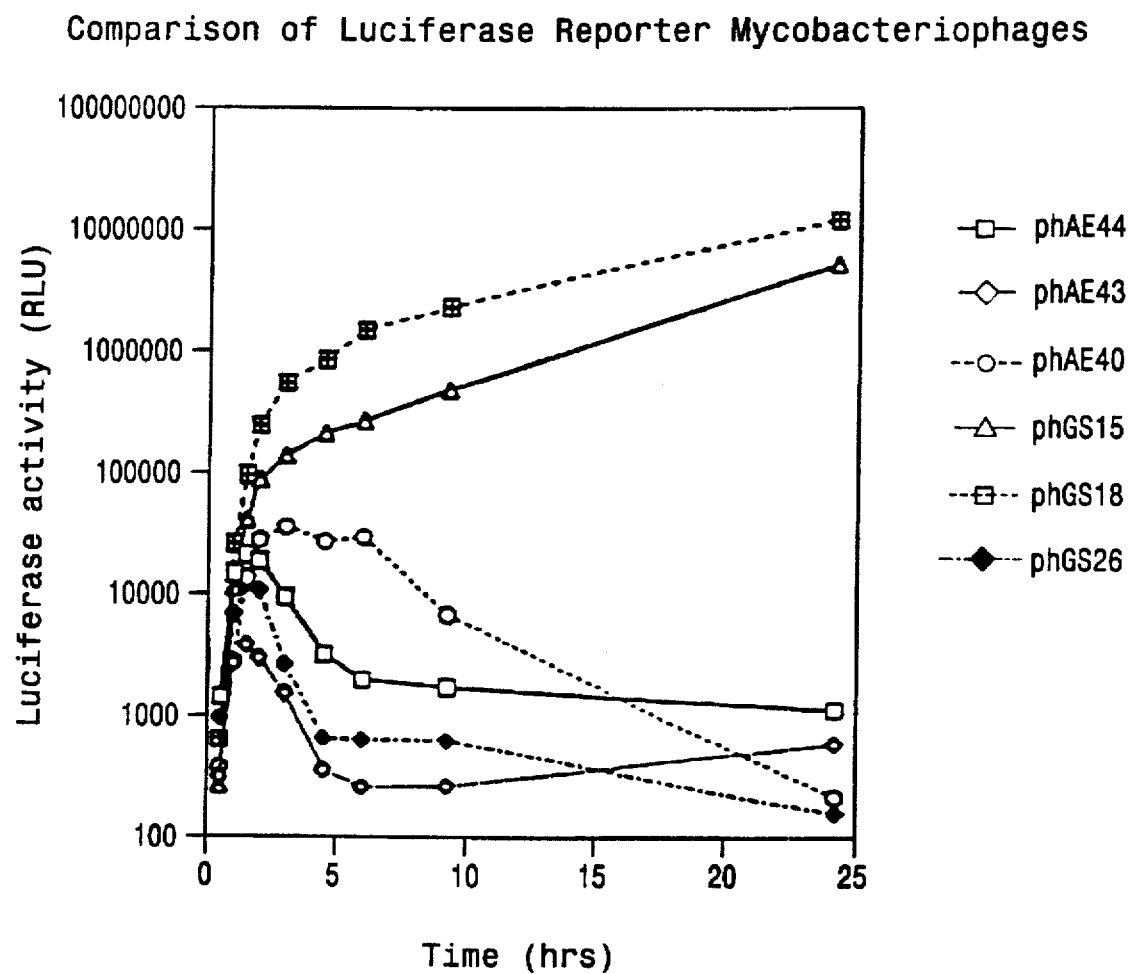
FIG. 7 represents the generation of light by the designated shuttle phasmids in *M. smegmatis* following infection with luciferase reporter phages and luciferase reporter shuttle phasmids.

The L5 luciferase shuttle phasmids, phAE43 and phAE44, were compared with the TM4 derived luciferase shuttle phasmid phAE40, which was deposited with the American Type Culture Collection, Rockville, Md., on Apr. 29, 1993, and catalogued as ATCC No. 75457 for their abilities to generate light in *M. smegmatis*. FIG. 7 demonstrates that both phAE43 and phAE44 luciferase shuttle phasmids yielded the production of photons in *M. smegmatis* in 1–3 hours post infection with yields surpassing the phAE40 yield 48 hours post infection. As a control, TM4-derived luciferase shuttle phasmid phAE40 yielded a very rapid burst of light, with maximal yields two to three hours post infection. This demonstrates that L5 shuttle phasmids can deliver luciferase genes to mycobacteria. In addition, this shows that L5 shuttle phasmids allow for the altering of every gene to determine the effect of each gene on luciferase production, and thereby provide tools for the further development of luciferase reporter phages.

EXAMPLE 6
Generation of insertion mutations with IS1096-derived transposons

As discussed hereinabove, it is desirable to obtain plasmids containing transposons for use in obtaining mycobacterial mutants. In order to perform this, several plasmids were utilized. Plasmids used in transposition experiments and their features are indicated in Table 1, below.

TABLE 1

Bacterial strains, plasmids and transposable elements

| Strain, plasmid, or transposable element | Relevant characteristics | Source or reference |
|---|---|---|
| *E. coli* DH5α | FΦ80dlacZΔM15 endA1 recA1 hsdR17 glnV thi-1 λ⁻ gyrA96 relA1 Δ(lacZYA-argF)U169 | Bethesda Research Laboratories |
| *M. bovis* BCG | Pasteur strain | Institut Pasteur |
| $mc^2789$ | *M. bovis* BCG[chr::Tn5367]met | This study |
| $mc^2797$ | *M. bovis* BCG[chr::Tn5367]leu-1 | This study |
| $mc^2798$ | *M. bovis* BCG[chr::Tn5366]leu-2 | This study |
| $mc^2826$ | *M. bovis* BCG#12[chr::Tn5367] | This study |
| $mc^2827$ | *M. bovis* BCG#13[chr::Tn5367] | This study |
| $mc^2828$ | *M. bovis* BCG#14[chr::Tn5367] | This study |
| $mc^2829$ | *M. bovis* BCG#21[chr::Tn5368] | This study |
| $mc^2830$ | *M. bovis* BCG#22[chr::Tn5368] | This study |
| $mc^2831$ | *M. bovis* BCG#23[chr::Tn5368] | This study |
| $mc^2849$ | *M. bovis* BCG#11[chr::Tn5367] | This study |
| $mc^2850$ | *M. bovis* BCG#15[chr::Tn5367] | This study |
| $mc^2851$ | *M. bovis* BCG#16[chr::Tn5367] | This study |
| $mc^2852$ | *M. bovis* BCG#17[chr::Tn5368] | This study |
| $mc^2853$ | *M. bovis* BCG#18[chr::Tn5368] | This study |

TABLE 1-continued

Bacterial strains, plasmids and transposable elements

| Strain, plasmid, or transposable element | Relevant characteristics | Source or reference |
|---|---|---|
| mc²854 | M. bovis BCG#19[chr::Tn5368] | This study |
| mc²855 | M. bovis BCG#20[chr::Tn5368] | This study |
| mc²856 | M. bovis BCG#24[chr::Tn5368] | This study |
| mc²857 | M. bovis BCG#25[chr::Tn5367] | This study |
| mc²858 | M. bovis BCG#26[chr::Tn5367] | This study |
| mc²859 | M. bovis BCG#27[chr::Tn5367] | This study |
| mc²860 | M. bovis BCG#28[chr::Tn5368] | This study |
| mc²861 | M. bovis BCG#29[chr::Tn5368] | This study |
| Bluescript ][ KS+/− | pUC derivative, Amp | Stratagene |
| pMV261 | contains oriE, oriM and αph genes | (38) |
| PYUB8 | pBR322 derivative containing oriE, αph and tet genes | |
| pYUB53 | pYUB8 derivative containing oriE, oriM, αph and tet genes | (22) |
| pYUB285 | ΔoriM, contains oriE and tet genes and Tn5367 | This study |
| pYUB297 | ΔoriM, contains oriE and tet genes and Tn5368 | This study |
| pYUB305 | ΔoriM, contains oriE and tet genes and Tn5367 | This study |
| PYUB312 | ΔoriM, contains oriE, αph and tet genes | This study |
| IS1096 | M. Smegmatis insertion sequence | (7) |
| Tn5366 | IS1096 derivative containing αph gene | This study |
| Tn5367 | IS1096 derivative containing αph gene | This study |
| Tn5368 | IS1096 derivative containing αph gene | This study |
| Tn5369 | IS1096 derivative containing αph gene | This study |

All plasmids have a ColE1 origin and an aminoglycoside 3′-phosphotransferase (aph) gene from Tn903 encoding kanamycin/neomycin resistance. This aph gene was PCR amplified from pKD348 (Derbyshire) to include a trp transcriptional terminator for use in transposon constructs. pYUB8 additionally has a tet gene; pYUB53 was derived from pYUB8 with the addition of the entire mycobacterial origin of replication from pAL5000; and pMV261 has a fully functional oriM, consisting of ORFs 1 and 2 from pAL5000. The remaining plasmids containing IS1096 were constructed as described herein. The DraIII deletion internal to the oriM was performed by digestion followed by T4 DNA polymerase treatment (Pharmacia). E. coli was transformed with plasmids by electroporation (Bio-Rad); or the CaCl₂ procedure using pretreated cells (Bethesda Research Laboratories). Plasmids were prepared from E. coli by both Birmboim/CsCl₂ and column (Quiagen) methods. M. bovis BCG cells were transformed by electroporation after washing in 10% glycerol, and then 4 mls complete media M-ADC-TW containing 0.5% casamino acids and 20 μg/ml tryptophan were added, followed by incubation overnight at 30° C. and plating on Middlebrook 7H10 with glycerol, ADC, cyclohexamide, amino acid supplements and kanamycin at 20 μg/ml. Colonies were counted after 3 weeks incubation at 37° C.

In order to perform Southern blotting and hybridization, single M. bovis BCG colonies were grown in 10 mls MADCTW containing kanamycin and expanded 1:50 for preparation of DNA. Whole DNA was prepared from 50 ml cultures, by a ten fold scale up of the CTAB method (see van Soolingen et al., J. Clin. Microbiol., Vol. 29, pp. 2578–2586 (1991)). DNA concentration was estimated by agarose gel electrophoresis and approximately 2 μg was digested with restriction enzyme and run on a 0.7% or 1% agarose gel at 40 V overnight. The DNA was transferred to nylon membrane (ICN). Hybridization was performed using plasmid pYUB285 as a probe labelled with [α-³²P]dCTP as described by Cirillo et al., J. Bacteriol., Vol. 173, pp. 7772–7780 (1991). The sizes of fragments hybridizing on KpnI and BamHI Southern blots were estimated using the mobilities of standard DNA markers run on each gel.

In order to isolate integrated transposons and perform sequence analyses, KpnI-digested fragments containing the integrated transposon were cut from an agarose gel and cloned into Bluescript II KS+ (Promega) using kanamycin selection. Outward primers based on the sequence of IS1096 were used with the Sequenase version 2.0 and the Longranger (United States Biochemical) acrylamide gel reagents. Sequences of the insertion sites were obtained for both DNA strands.

Auxotrophs were then isolated. Colonies obtained on pYUB284 and pYUB297 transformation were picked using wooden sticks into 96-well plates containing complete medium. They were grown up and washed twice in minimal (M-ADC-TW) medium before being replicated onto agar plates with and without amino acid supplement using a 96-prong template (Dankar). Candidates were further streaked from the original 96-well plate to check their auxotrophy, and auxonographic analysis was performed on washed cultures as described by Kaplana et al., Methods Enzymol., Vol. 204, pp. 139–180 (1991).

IS1096-derived transposons were constructed. The kanamycin resistance gene (aph) from Tn903 was PCR-amplified and cloned into the unique SalI, MluI or NcoI sites in the insertion sequence IS1096. This created a set of three transposons, having the aph gene in each of the open reading frames of IS1096, as well as between them. The elements are shown in FIG. 8. Tn5368 has the aph gene inserted into ORFR. Tn5369 has the insertion in ORFA, and in Tn5367, the aph gene does not disturb either ORF. Tn5366 is identical to Tn5367 but has the aph gene in the reverse orientation. TnpA and TnpR have been denoted ORFA and ORFR, respectively.

In order to construct transposon delivery plasmids, IS1096, with its adjacent lacZ sequences, (100–200 base pairs on each side), was cloned in both orientations into the multicloning site of pGEM7Zf+ (Promega) to create plasmids pYUB234 and pYUB235, thereby enabling excision of the element with EcoRI and HindIII. A third vector, pYUB272, was constructed, with EcoRI and HindIII sites, as well as origins of replication for E. coli and mycobacteria and a tetracycline resistance, tet gene. This plasmid was derived from pMV261 by replacement of the NotI-PstI fragment with a tetR gene obtained by PCR from pYUB53. The transposons Tn5368 and Tn5369 which were created on pYUB234 were inserted into pYUB272 by ligation after digestion with EcoRI and HindIII. In order to obtain a delivery plasmid which is unable to replicate in mycobacteria, the mycobacterial origin of replication (oriM) was inactivated in each of the constructs by an internal deletion using DraIII, which removed 556 base pairs of DNA and a significant part of an open reading frame in the origin of replication.

Tn5367, having an aph gene in the MluI site, was created after ligation of the IS element to pYUB272. Insertion of the aph gene into the MluI site of the IS element necessitated a partial digestion since there is also an MluI site in pYUB272. The construct obtained from insertion into this second site provided a plasmid having the aph gene outside the transposon, which could then be used as a control to monitor any illegitimate integration of the plasmids. DraIII deletions within the oriM were also performed on these two plasmids. The four plasmid delivery constructs, pYUB285, pYUB297, pYUB305 and pYUB312, are shown in FIG. 9.

*M. bovis*-BCG with transposon delivery constructs were transformed. The numbers of kanamycin-resistant colonies resulting from five transformation experiments are shown in Table 2, below. In addition to the transposon delivery plasmids, three additional plasmids were used as controls. The efficiency of transformation was determined with an oriM-containing vector. Either pMV261, or pYUB53 and any illegitimate integration was monitored using either one of two plasmids: pYUB312 with oriM deletion but the aph gene outside the insertion element; or pYUB8 which has no insertion element or mycobacterial origin, but has an aph gene. A control of cells alone having no plasmid was also electroporated and plated in an identical fashion to the samples to estimate the level of spontaneous resistance to kanamycin ("background").

transposition and is likely to be the transposase. There is no evidence of illegitimate integration of plasmids since transformation with pYUB312 or PYUB8 yields numbers at background levels.

In order to perform analysis of kanamycin-resistant colonies using Southern blotting, twenty colonies arising from transformation of pYUB285 and pYUB297 were picked at random, grown up in the presence of kanamycin and examined by Southern blotting using three different enzymes and plasmid pYUB285 as probe. The Southern blot results of six of such clones, strains $mc^2826$–$mc^2831$, are shown in FIG. 10. Using KpnI, one fragment hybridizes in each clone (see FIG. 10A), since there is no KpnI site in the transposon. To verify that insertion was random, BamHI was also used. This enzyme cuts once within the transposon, and when probed with plasmid, two bands are seen, corresponding to fragments obtained from the transposon's insertion into the chromosome (see FIG. 10B). These fragments appear to be of random size, and indicate that $mc^2830$ and $mc^2831$, which yield similar-sized KpnI fragments, are not identical clones.

Digestion with PvuI and hybridization with plasmid was carried out in order to determine whether any plasmid sequences were present which would suggest either the presence of cointegrate intermediates or an illegitimate recombination event. The results are shown in FIG. 10C. Digestion of the delivery plasmids with PvuI yields several fragments, including one internal to the transposon (see FIG. 9). If transposition had occurred by simple insertion rather than replication and cointegrate formation, the expected bands from the transposon-containing clones would include this internal fragment and two additional bands resulting from the insertion of the transposon into the chromosome. Three bands were seen with Tn5367 insertions $mc^2826$, $mc^2827$, $mc^2828$, each with expected internal band as well

TABLE 2

*M. bovis* BCG transformation

| | Plasmid | | | | | | |
|---|---|---|---|---|---|---|---|
| Experiment[a] | pYUB285 | pYUB297 | pYUB305 | pYUB312 | pYUB8 | none | oriM⁺/μg[c] |
| 1 | 255 | — | — | — | 14 | — | $4.5 \times 10^4$ |
| 2 | 155 | 104 | — | — | 16 | 31 | $1.5 \times 10^4$ |
| 3 | 426[b] | 225 | — | 59 | — | 60 | $5 \times 10^4$ |
| 4 | 67 | 98 | 18 | 3 | — | 6 | $4.4 \times 10^4$ |
| 5 | 325 | — | 60 | 41 | — | 36 | $1.3 \times 10^5$ |

[a]Within each experiment, the same amount of plasmid was transformed; Experiment 1: 02 μg; Experiment 2:5 μg and Experiment 3-5: 400 ng, except;
[b]1 μg plasmid was used.
[c]For the oriM⁺ control plasmid, 0.2 μg-0.4 μg was used, and numbers are represented as transformants per μg. Two different plasmids were used; Experiments 1 and 2: pYUB53 and Experiments 3-5: pMVV261.
[d]Recoverey conditions after electroporation were 37° C. instead of 30° C.
—Dashes represent data not obtained.

The results show that in each experiment there is a transformation frequency of $10^4$–$10^5$/μg with the oriM-containing plasmid, and a number of kanamycin-resistant colonies arising from transformation with pYUB285 or pYUB297. These numbers are well above background from any of the controls and shows transposition. Furthermore, while pYUB285 contains Tn5367 having both ORFs of the IS element intact, pYUB297 carries Tn5368 in which ORFR is disrupted, implying that this ORF is not required for transposition. In addition, the numbers of colonies obtained for pYUB305, the construct carrying Tn5369, in which ORFA is disrupted, are sharply reduced to close to background levels, suggesting that this ORF is required for as two unique bands of differing size. Results for the clones transformed with Tn5368 show that one of the clones ($mc^2829$) gives three bands, but the other two ($mc^2820$ and $mc^2831$) display only one additional band along with the expected internal fragment, suggesting that deletions of the transposon are occurring. The absence of extra bands, however excludes the possibility of plasmid integration.

Of the 20 colonies analyzed in total, one clone did not hybridize on Southern blot, suggesting that its kanamycin resistance was due to a spontaneous mutation. The results of Southern blots of the remaining 19 clones with KpnI and BamHI were analyzed and are represented graphically in FIG. 11, to illustrate the random nature of insertion of Tn5367 and Tn5368 into different restriction fragments in each clone. The KpnI fragment sizes were plotted in descending order and the BamHI fragments corresponding to each lone are superimposed. This representation of the data was chosen so that results for each enzyme could be combined to show that the insertion site of the transposon differs for each clone. Even clones showing similar sized KpnI fragments differ in the size of the BamHI fragment into which the transposon was inserted. No plasmid sequences were detected after Southern blotting using PvuI.

Insertion junctions were then sequenced. IS1096 was previously found to create 8-base pair direct repeats on insertion into its target site (see Cirillo et al., *J. Bacteriol.*, Vol. 173, pp. 7772–7780 (1991)). Therefore, sequencing was performed on the six clones ($mc^2$826–$mc^2$831) described above in order to confirm that the transposons retained this property, and in order to investigate any target-site preference. The sequences of the duplicated target sites are given in FIG. 12. There is a weak consensus at the insertion junctions of XXXTA/TXC/GX, where T always stands at position 4, and there is a preference in the target site for an AT-rich center and GC-rich ends. No similarities were seen between clones comparing 50 base pairs of flanking DNA.

Auxotrophic mutants were isolated and characterized. 923 kanamycin-resistant colonies resulting from the first and second experiments (see Table 2) were arrayed in 96-well plates, grown up, washed and tested for auxotrophy by patching onto plates lacking amino acid supplement. Candidates were tested in auxonography and three auxotrophs were found, one for methionine ($mc^2$789) and two for leucine ($mc^2$797 and $mc^2$798). The leucine mutants appeared to be distinct, as $mc^2$798 grows more slowly than $mc^2$797. The growth of all three auxotrophs could be supported in liquid or solid minimal media by the addition of the relevant amino acid.

A transposon capable of random insertional mutagenesis in the *M. tuberculosis* complex allows for the isolation of auxotrophic mutants of *M. bovis* BCG and *M. tuberculosis*, which can be used for vaccine development and in new approaches to the study of virulence, such as in vivo expression technology (IVET). It also facilitates the analysis of mechanisms of invasion and survival in the host, and can lead to the identification of new drug targets in *M. tuberculosis*. The ability to mutate genes and locate them easily, is essential in the *M. tuberculosis* complex where gene replacement by homologous recombination prior hereto, has been is difficult.

The inventors have shown that transposons derived from IS1096 do transpose in BCG. The products of transposition appear to be the insertion of one copy of the transposon, with no cointegrates or plasmid sequences. The inference that ORFA is a transposase, and should be referred to as TnpA, is also supported by the recent isolation of insertion element IS1001 from *Bordetella pertussis* and ISAE1 from *Alcaligenes eutrophus*, which both have an open reading frame with homology to ORFA of IS1096 (see Van der Zee et al., *J. Bacteriol.*, Vol. 175, pp. 141–147 (1993) and Kung et al., *J. Bacteriol.*, Vol. 174, pp. 8023–8029 (1992)). Tn610 from *M. fortuitum* and transposon derivatives of IS900 from *M. paratuberculosis*, transpose by a replicative mechanism which can involve cointegrate formation (see Martin et al., *Nature*, Vol. 345,k pp. 739–743 (1990) and England et al., *Mol. Microbiol.*, Vol. 5, pp. 2047–2052 (1991)). It is not uncommon for insertion sequences to exhibit more than one open reading frame. These can be involved in the transposition mechanism, or in the regulation of transposition. If ORFR is indeed a resolvase, it is not required for transposition or resolution in *M. bovis* BCG. However, two of the clones analyzed by Southern blot using PvuI showed evidence of deletions, and both of these clones were derived from transformation with Tn5368, having an insertion in ORFR.

In nineteen out of twenty clones isolated at random, the transposons were found in different sites in the chromosome, as evidenced by restriction fragment size on Southern blotting. In each of the six insertions sequenced, a target duplication of eight base pairs was seen on either side of the element. The DNA sequence of the insertion site differed in each clone analyzed, with only a weak consensus, indicating that there is little constraint on insertion site. Two of the clones have the sequence ATAA at the center. The related IS1001 and ISAE1 both recognize AT-rich targets. IS1001 recognizes runs of As or Ts, and ISAE1 has a preference for A or T at the ends. Both bacteria are also high %G+C organisms. The random nature of the transposition and the ability of the transposons to insert into coding regions is also demonstrated by the isolation of methionine and leucine auxotrophs in BCG.

EXAMPLE 7

Characterization of methionine and leucine auxotrophs of BCG generated by IS1096-derived transposons IS1096-derived transposons are able to transpose in BCG. In order to show this, a library of approximately 1000 random insertions of IS1096-derived transposons in BCG was screened for the ability to grow on minimal media after originally selecting on media containing casamino acids. Three auxotrophic mutants of BCG were identified. Auxonography analysis revealed that two of the auxotrophs were leucine-requiring mutants, and one was a methionine-requiring mutant. The reversion frequencies were determined to be between $10^{-7}$ to $10^{-8}$, as shown in Table 3, below. When the BCG auxotrophs were then grown in mice, it was determined that the auxotrophs possessed very properties. The methionine auxotroph resembled BCG when inoculated in mice. In contrast, both of the leucine auxotrophs were cleared rapidly from both the spleens and lungs of the mice (see FIG. 13). This confirms that the IS1096-derived transposons caused different mutations in BCG.

TABLE 3

*M. bovis*-BCG Strains

| Strain | Genotype | Phenotype | Reversion Frequency |
|---|---|---|---|
| BCG-Pastuer | wild-type | prototroph | NA |
| $mc^2$797 | leuD1::Tn5367 | leucine auxotroph | $1.6 \times 10^{-7}$ |
| $mc^2$798 | leuD2::Tn5366 | leucine auxotroph | $2.0 \times 10^{-7}$ |
| $mc^2$789 | met-2::Tn5367 | met auxotroph | $1.0 \times 10^{-7}$ |
| $mc^2$796 | zzz::Tn5366 | prototroph | NA |

EXAMPLE 8

Construction of L5 transposon delivery vectors phAE46 and phAE47

By utilizing the cosmid replacement technology in L5 replacement shuttle phasmid phAE41, the pYUB328 cosmid was replaced by the cosmid pYUB435. The pYUB435 cosmid was cloned into the EcoR1 site of both phAE41 and phAE42 in order to generate L5 shuttle phasmids phAE46 (see FIG. 14) and phAE47 (see FIG. 15), respectively. The resulting transposon delivery vectors phAE46 and phAE47 were deposited with the American Type Culture Collection, Rockville, Md., on May 20, 1994, and catalogued as ATCC Nos. 69629 and 69630, respectively. Both of these vectors contain the IS1096-derived transposon Tn5367 which was shown to be able to transpose and make mutations in BCG (see Examples 6 and 7).

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 50341
        ( B ) TYPE: nucleic acid
        ( C ) STRANDEDNESS: single
        ( D ) TOPOLOGY: linear ( i i ) MOLECULE TYPE:
        ( A ) DESCRIPTION: L5 shuttle phasmid sequence ( i i i ) HYPOTHETICAL: No ( i v ) ANTI-SENSE:

( v ) FRAGMENT TYPE:

( v i ) ORIGINAL SOURCE:
        ( A ) ORGANISM: L5 mycobacteriophage
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( v i i i ) POSITION IN GENOME:
        ( A ) CHROMOSOME/SEGMENT:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION: None
        ( A ) AUTHORS:
        ( B ) TITLE:
        ( C ) JOURNAL:
        ( D ) VOLUME:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO: 1:

```
GGCGCTCTCG   CATCGCATCG   AGTGTTTGCT   GTGTCTCTCA   TCGTCGCAGG   TCAGAAGGGG        60

TAGGGGGGTT   CCCCCTAGGG   GTCGGTCCTT   GACCGGTCGG   TTAGGTCGGT   TATGCGGCCG       120

AGCCATCCTG   TACGGGTTTC   CAAGTCGATC   AGAGGTAGGG   GCCGGCACAG   AAACCACTCA       180

CATCAGGGCT   GTGCGCCTCC   AGGGCGCGTG   AACTCCCACA   CCCCGGTGTA   GTTACATCCC       240

GGAATTGTCT   CAGCGCCTCT   CAGGGCGCTT   CTCATAAACA   GTGATCTACG   CCACTCCTGA       300

CGGGTGGCTG   TCAAGGATAC   TCACCTTCCC   TACTAATGAG   GGGCTAAGAG   CCCCTCTCTA       360
```

| | | | | | |
|---|---|---|---|---|---|
|TAGAGCGCCG|CACAGGCGGC|GCGATAAGAG|CGCCACCAGG|CGCTCATCTA|AAGACCGGCC|420|
|TTGAAGGGCC|GGTCATAGAG|ATCTATTCGA|TCCGGCAACC|GCCGGATCTC|AAGGCCGCGC|480|
|CAGTGCGCGG|CCCTATAGAG|GGGTGACTCA|ACTGTGCATG|GCACTCGCTC|GAGTGCCAC|540|
|TGGAGCACTC|AACCGGGGAA|GTTCGACGTT|CTCAACCTGC|GAATGACGTT|TGAATCGTCA|600|
|TCCGCGTACG|AAATCCCCGA|TCTGCGGCCG|ACCGACTTCG|TGCCGGCCTA|TCTCGCGGCC|660|
|TGGAATATGC|CGCGTCACCG|CGATTACGCC|GCCAAGAACG|GCGGCGCGCT|GCACTTCTTC|720|
|CTTGACGATT|ACCGGTTTGA|GACCGCGTGG|TCGTCCCCCG|AGCGCCTTCT|CGACCGCGTA|780|
|AAGCAGGTCG|GCGCTGCACT|CACGCCGGAT|TTCAGCCTCT|GGACGAACAT|GCCGAAGGCG|840|
|GCGCAGCTAT|GGAACGTCTA|CCGCTCCCGC|TGGTGTGGCG|CGTATTGGCA|GTCGGAAGGA|900|
|ATCGAGGTGA|TTCCGACGGC|GTGTTGGGCG|ACTCCCGACA|CGTTCGATTT|CTGTTTCGAC|960|
|GGGATCCCGA|TGGGATCGAC|CGTCGCAATT|TCTTCGATGG|GCATTCGCTC|TTCAAAAGTC|1020|
|GACCAGGAGC|TTTTCCGGTA|CGGACTACGC|GAACTCATCG|ATCGCACTCA|ACCGCAACTG|1080|
|CTTTTGGCAT|ATGGCCAGCT|TCGGCATTGC|GACGACATGG|ATTTACCAGA|GGTCCGCGAA|1140|
|TACCCGACCT|ACTGGGACAG|ACGACGAAAG|TGGGTAACTG|CCGATGGGAG|GCCGGGGAAG|1200|
|TAAAGGCGGC|CCCGGTCCCG|GAACCGGAGC|ACGCAACCGC|AGAGGCGCTG|GAGCCCCCGG|1260|
|ATCGGGCGGC|GTAGGCGGCG|TCGGAGGCGG|GGGTGGAGCT|GCAGGGAGCA|GCGGAGGCGG|1320|
|CAAGGGAACG|GCAGCGCCGG|TACCGGAGGC|GTCACCGGTG|GCGGCGGAAG|TGGAGCCGGC|1380|
|GGCGGTGGCA|GCAGCCCCAA|CACCCCGGTG|CCCCCCACCG|AGCTGGAGAA|GAAGCGCGGC|1440|
|GAATACAACC|AGATCGCCAT|CGACGCCCAG|AAACAGCACG|CGCCCACCGA|TGAGAAGCGC|1500|
|GAGGCCAAGC|GCAAGCAACT|GATGGATCGA|GTCGGAGGAG|ACTGGCAGGC|TTTGGACCCG|1560|
|GATCACCACG|ACGCCATCAA|GGTGGCGATG|GATGACGCCA|TGCGGAAGAT|CCTCTCCGAG|1620|
|GAGGAGATCG|TCCACCGCAC|CAAGCACTTC|GGCGACCTAC|TCGACTCCGG|TCGACTCAAG|1680|
|TCGCTGTTCG|AGGTCGGCTT|CTCAGCCGGT|GGCGACACCC|CGACCGAACG|CGCCCTCCTC|1740|
|GAGGACGCCT|GGTTCGGCGC|AGGCAAGGTT|CCCCCGATCT|ACTCGGCAAT|CGAGTTCAAC|1800|
|GGCGCTCCGA|CAGCCGGCCT|CGGCATGTAC|GGCGGCACCA|AGCTCTACAT|GAAGGACTCG|1860|
|GTCAAGGACC|GCGTCACCGT|GACCATCGGC|GACTCGCTGA|TGTCGAGCTG|GACGTATTC|1920|
|CCCGGCCGTC|CTGGCGACGG|CGTGGGCTG|TGGGCCAGCC|TGTCGAAGAT|CGAGGGGCTG|1980|
|GTCGATCCGA|GCAAGACCCG|CGAAGAGAAC|ATGCAGGCGG|TGTACGACTC|GTTCAAGAAG|2040|
|TACGGCACCC|TGGACGGCTT|CATCGAGGCG|CAGATCCACG|GCGGCGTCCT|GGTCGAGGAC|2100|
|ATCAAGAAGG|TCGTGTTCAC|GCAGCCGCCG|AGCCCGATCT|TCACCGATAA|ACTGGACGAA|2160|
|CTTGGAATCC|CGTGGGAGGT|GCAGTAATGG|CGCAGATGCA|GGCGACACAC|ACAATCGAGG|2220|
|GGTTCCTGGC|TGTCGAGGTG|GCCCCTCGGG|CGTTCGTCGC|AGAGAACGGC|CACGTACTGA|2280|
|CCCGGCTGTC|GGCCACGAAG|TGGGCGGTG|GCGAGGGTCT|CGAGATCCTC|AACTACGAGG|2340|
|GTCCAGGGAC|CGTCGAGGTC|TCCGACGAGA|AGCTCGCCGA|AGCCCAGCGG|GCCAGCGAGG|2400|
|TCGAGGCTGA|ACTTCGCCGC|GAGGTCGGCA|AGGAGTGAGC|TGGGCCGGCT|CAGGCCGGCG|2460|
|ACAGGAACTA|CCAGAGGACT|GGGAGCTGAA|TTACCGGCTC|CCGGTCCTTT|CTGCTGCCAA|2520|
|CTGGCTTTGC|CAGATCAACG|GTCCCGGATG|CGTAAGGGCC|GCAACCGATG|TCGACCACAT|2580|
|CAAGCGCGGG|AACGACCACA|GCCGGTCCAA|TCTGCAGGCA|GCCTGCCATG|TCTGTCACGG|2640|
|CAAGAAATCA|GCCGCCGAGG|GCGTAGCCCG|ACGGCGGGAA|CTTAGAGCCC|GGAGGAAGCG|2700|
|ACCACCCGAA|CGCCATCCTG|GGCGTCGATA|AGCGGGCCAG|GTGCCCGCTC|CACCCAGGAG|2760|

```
GTGAACAGTG GGCACGCGAG GCCCAATCGG AAAACGAGAT GAAGAGCGGG TTCGTCGGAA     2820
CACCCCGGAC AGTCCAACCG ACACGATCCA GATGCCCGGT CTGGTGACGA TCCCCGAGAT     2880
GGGCGATCTA AGCCACGACG GCCGCACGCA CCAGCTCGTC AAGGACATGT ACGAGTCGAT     2940
CAAGCAGTCG GCAGCCGTGA AGTACTACGA GCCGACCGAC TGGCAGATGG CCCGACTCGC     3000
CCTCTACACA CTTAACCAGG AACTCATCGC AGCCGAGAAC AACGGCAAGC CCGTGGGCGC     3060
GATGAAGCTC ACTGCCATCA ACCAGATGCT CTCCGCGCTG CTGCTGACCG AAGGTGACCG     3120
ACGCCGCGTC CGACTCGAAG TCGAACGAGC ACCCGCTGAC CCGACAGGCG GGAAGGTCGT     3180
TGACGTGACC GACGTGCTCA AGCAGCGCCT CGCCAAGGCG AGCGGCGGGA GCTGATGGTC     3240
CCCCGAGGGG TTTCTAGAGC CGCTGCCGCT ACCAGCCGCT CCCCCTCGGG GTAGACATCG     3300
AAAGGAACCA CATGGCCGAC CTCGGCAACC CACTCGACCT CGAGATGCTC TGCCTGGTCA     3360
CAGGCCGGGA CTTCCGCTGG ACCATCGATT ACCCGTGGGG TCCGGGAGAG CTGTTCCTCG     3420
AACTCGAGAC CGGCGGCGAA CACAACGCGC TGCATCAGGT CTATGTCACC GGGGCGACCG     3480
GAGGCACGTA CACGCTGAAC GTCAACGGCA CCAACACCCC GGCCATCGAC TACAACGACG     3540
TGTCGGAGAA TCCGCAGGGG CTGGCAGGCG ACATCCAAGA CGCTCTGGAC GCAGCCGTCG     3600
GAGCCGGAAA CGCTGTCGTG CATCCGGTCT CGCTGTTCCC TGCGTGGACA CTGAACTTCA     3660
ACCTCAACGC CAGCAAGCCG CTCACCGAGC AGTTGGTCAA CACGATCAAC AAGGCCGCGA     3720
ACGACTTCTT CGACACGTTC GACCAACTAC TTGGGGTCGA CGTGGAGATG ACGGTCACCG     3780
ACACCCTGAA CTTCAAGCTC AAGGTGACCT CGCGGCGCTC GTTCGATGAG GTCGGTGTCG     3840
TCACGTTCGC GGTCGACGTG ACCAGCCAGG CAGTCATCAA CTTCTTCAAC TCCGTCGCCG     3900
AACTCACCGG AGCGGTGAAC ACCGTCAACG TCGACTTCTA CTGGAACCGG ACGTATGACA     3960
TCGAGTTCAC CGGATCCCTT GGGCTGCAGC CGATTCCGGC TACTACAGCC GACATCACCA     4020
ACCTGGCGGG TACCAGCAAG GCCGTCTCAG TCACGGTGGT CGAGCCAGGA AAGAAGAGGC     4080
TGACCATCTG GCCGTTCACG GTCAACGGTG AAACCGCAAC CATCAAGGTC GAGTCCGAAG     4140
AGGCCGACAA GATCCCCAAC CGCTGCCGCT GGCAGTTGGT TCACATGCCG ACCGGCGAGG     4200
CAGCCGGCGG CGATGCAAAG CAGCTCGGCC GCGTTTACCG ACAGCCGAGG TAACACCGCA     4260
CCCATCAGAG ATGGTGGGCC AGACGGCCTT CGGGCCGTCC CCTGACGTGT AGCTCAATGG     4320
CAGAGCGCCC GACTGTTAAT CGGGTGGTTG AAGGTTCGAG TCCTTCCATG TCAGCGAGGG     4380
CTGAACCGGA CCCGTGTCCG GTGTAGGCAC TTTCCGCAGG CGGTTCCCCA GAGCGTGGGG     4440
AGCCCCTGCC CTGTACACGT AGCTCAATTG GTAGAGCAGC GGTCTCCAAA GCCGCCGGTT     4500
CCAGGTTCGA CTCCTGGCGT GTATGCACAC ACCCTGACT CCTGCTAGCG GAGTGTTCGC     4560
CTTTCGGGCC TGGGGTCTTT TTCCCCGTTC GTCTAATCGG TAAGACACCC GGCTCTGGAC     4620
CGGGCAATTG AGGTTCGAGT CCTTGGCGGG GAGCCAACTT GACATCCACC GAAAGGAAC     4680
AACATGACCT TCACAGTCAC CCGCGAGAGA GCGCAGTGGG TCCACGACAT GGCCCGCGCT     4740
CGCGACGGTC TCCCCTACGC GTACGGCGGG GCGTTCACCA CAACCCGAG GGTGTCGACT     4800
GACTGCTCTG GCCTGGTGCT GCAGACCGGG GCTTGGTATG GAGGTCGCAC CGACTGGGTC     4860
GGAACCGTT ACGGCTCAAC CGAATCGTTC CGGCTCGACC ACAAGATCGT CTACGACCTA     4920
GGGTTCAAGC GGATGCCCCG AGGCGGGCCA GCGGCCTTGC CGATCAAGCC GGTGATGCTC     4980
GTCGGGCTCC AGCACGGAGG CGGCGGGGTC TACTCGCACA CCGCTTGCAC GTTGATGACG     5040
ATGACCACC CCGGTGGCCC GGTCAAGATG TCCGACCGAG GCGTCGACTG GGAGTCCCAC     5100
GGCAACCGCA ACGGCGTAGG CGTCGAACTT TACGAGGGCG CACGGGCATG GAACGACCCT     5160
```

```
CTGTTCCATG ACTTTTGGTA CCTGGACGCA GTCCTCGAAG ACGAAGGAGA CGATGACGAA    5220
TTGGCTGACC CAGTTCTAGG GAAGATGATC CGCGAGATCC ACGCGTGCCT GTTCAATCAG    5280
ACCGCGTCGA CCAGCGATCT GGCGACCCCT GGTGAAGGCG CTATCTGGCA GCTACACCAG    5340
AAGATCCACT CGATTGACGG CATGCTCCAC CCGATCCACG CTGAGCGGCG CGCTCGCGCA    5400
GGCGATCTCG GTGAGCTGCA CCGAATCGTG TTGGCCGCGA AGGGCTTGGG CGTGAAGCGC    5460
GACGAGGTGA CCAAGCGGGT CTACCAGAGC ATCCTCGCCG ACATCGAGCG GGACAACCCC    5520
GAAGTACTTC AGCGATACAT CGCAGAAAGA GGTGGCCTAT GAGCCCAAG ATCCGACAGA     5580
CCATCTACCT GCTCGGCACC GCCGCCCGG CACTGCTGGG CATCGTCCTG ATCTGGGGCG     5640
GGCTCGACGC TGAGTCGGCG GCTGACCTCG GTGACATCAT TGCGGGCGTC GTGTCGATAC    5700
TAGTCTCCGG TGCGCCGGCC GTAGCGGCAG GCACCGTACG CAGCCAGCGC AAGGACGGCA    5760
CGTTGTCCAC CAGCCCGGTG GATCAGGTCA CCAAGGGCGT CGAGCAGGTG CTCGCGGCCA    5820
GGCAGAGTGC CGAGGCTGAA GTCGCGAAGG TCAAGCAGGC GCTGGAGACC GCCGTCAGCG    5880
GTTCTCTCCC CCAGCTCGGC CCGCTGGCCA CGCAGATCCT CAACGTGGCT GACGACACCG    5940
TCTGGCGTCC ATGAGCAAGC CCTGGCTGTT CACCGTCCAC GGCACAGGCC AGCCCGACCC    6000
GCTCGGGCCT GGTCTGCCTG CCGATACCGC ACGGGACGTA CTTGACATCT ACCGGTGGCA    6060
GCCCATCGGC AACTACCCGG CAGCGGCGTT CCCGATGTGG CCGTCGGTCG AAAAGGGTGT    6120
CGCTGAGCTG ATCCTGCAGA TCGAGCTGAA GCTGGACGCA GATCCGTACG CGGACTTCGC    6180
GCTGGCCGGC TACTCGCAGG GAGCCATCGT GGTGGGCCAG GTGCTCAAGC ACCACATCAT    6240
CAACCCGAGA GGTCGACTGC ACCGGTTCCT GCACCGGCTC AGGAAGGTCA TCTTCTGGGG    6300
TAATCCGATG CGGCAGAAGG GCTTTGCCCA CACCGACGAG TGGATTCACC AGGTCGCTGC    6360
CTCGGACACG ATGGGCATCC TCGAGGACCG ACTGGAGAAC CTCGAGCAGT ACGGCTTTGA    6420
GGTCCGCGAC TACGCGCACG ACGGCGACAT GTACGCCTCC ATCAAGGAGG ACGACATGCA    6480
CGAGTACGAG GTGGCCATTG GCCGAATCGT GATGAGCGCT AGGCGATTCA TCGGAGGTAA    6540
GGACTCCGTC ATCGCCCAGC TCATCGAGCT TGGACAGCGT CCGATCTGGG AGGGAATCGC    6600
GATGGCCAGA GCCATCATCG ACGCCCTCAC GTTCTTCGCC AAGTCGACCC AAGGCCCGAG    6660
CTGGCCGCAT TTGTACAACC GCTTCCCGGC GGTCGAGTTC CTACGACGAA TCTGAGAAAG    6720
GAGGCGGGGT GAGCCTCAAC AACCACCACC GGAGCTTGC CCCGTCTCCC CCTCACATCA     6780
TCGGCCCGTC CTGGCAGAAG ACGGTCGATG GTGAGTGGTA TCTGCCTGAG AAGACCCTCG    6840
GCTGGGGAGT CCTGAAGTGG CTCTCCGAGT ACGTGAATAC CCCTGGCGGG CATGACGATC    6900
CGAACCGTCT GGCGACGTTG ATCGCGCTCT CCGAGGCAGG TCTTCTCGAC AACGAGAACA    6960
TGTTCATCCC CACCGACGAG CAGGTACGCC TGGTCCTCTG GTGGTACGCA GTAGATGACC    7020
AGGGCCAGTA CATCTACCGC GAGGGCGTGA TCCGCCGGCT CAAGGGCTGG GGCAAGGATC    7080
CGTTCACCGC CGCGCTCTGC TTGGCGGAAC TCTGTGGCCC CGTAGCCTTT TCACACTTCG    7140
ACGCCGACGG TAACCCGGTC GGCAAGCCGC GTTCAGCCGC GTGGATCACC GTCGCGGCCG    7200
TCAGCCAGGA CCAGACGAAG AACACGTTCT CGCTGTTCCC GGTGATGATC AGCAAGAAGC    7260
TGAAGGCCGA GTACGGCCTG GACGTGAACC GCTTCATCAT CTACTCCGCA GCCGGTGGCC    7320
GTATTGAGGC AGCGACCTCG AGCCCGCGT CGATGGAGGG TAACCGCCCG ACGTTCGTCG     7380
TCCAGAACGA GACGCAGTGG TGGGCCAAG GCCCGACGG CAAGGTCAAT GAAGGCCACG      7440
CGATGGCAGA GGTCATCGAA GGCAACATGA CCAAGGTCGA GGGCTCCCGC ACCCTGTCGA    7500
TCTGCAACGC CCACATCCCC GGCACCGAGA CGGTCGCCGA GAAGGCATGG GACGAGTACC    7560
```

```
AGAAGGTCCA GGCAGGCGAC TCTGTCGACA CCGGGATGAT GTACGACGCG CTGGAAGCGC    7620
CGGCCGACAC CCCGGTCTCC GAGATCCCCC CGCAGAAGGA GGATCCCGAG GGATTCGAGA    7680
AGGGCATCGA GAAGCTCCGC GAGGGCCTGC TCATCGCCCG AGGCGACTCC ACCTGGCTGC    7740
CGATAGACGA CATCATCAAG TCGATTCTGT CGACCAAGAA CCCGATCACC GAGTCGCGGC    7800
GCAAGTTCCT GAATCAGGTA AACGCCGCTG AGGACTCGTG GCTCTCACCG CAGGAATGGA    7860
ACCGGTGCCA GGTCGACCTG GCCAAGTACC TGGATAAGCA CGGCAGGGAG TTCGCTCCGC    7920
TGCAGCGCGG TGACCGGATC ACCCTCGGGT TCGACGGGTC GAAGTCCAAC GACTGGACCG    7980
CGCTCGTCGG CTGCCGTGTC AGCGACGGCC TGCTGTTCGT CATCGACATC TGGGATCCCC    8040
AGAAGTACGG CGGGGAGGTT CCCCGCGAAG ACGTTGACGC CAAGGTCCAT TCGGCGTTCG    8100
CCCACTACGA CGTGGTGGCG TTCCGCGCCG ACGTGAAGGA GTTCGAGGCG TACGTCGACC    8160
AGTGGGGCCG GACCTACAAG AAGAAGCTCA AGGTCAACGC CAGCCCGAAC AACCCGGTGG    8220
CGTTCGACAT GCGCGGACAG CAGAAGAGGT TCGCGTTCGA CTGCGAGCGA CTCGAGGACG    8280
CGGTCCTTGA GGGCGAGGTC TGGCACGACG GCAATCCCGT TCTGCGCCAA CACGTTCTGA    8340
ACGCCAAACG ACACCCAACG AACTACGACG CCATCGCGAT TCGCAAGGTC ACGAAGGACT    8400
CCAGCAAGAA AATCGACGCT GCAGTCTGCG CTGTCCTCGC GTTCGGGGCG AGACAGGACT    8460
ACCTCATGAG CAAGAAGGCC CGTAGCGGCC GGGTGGTGAT GGTTCGATGA CAGCACCGCT    8520
CCCCGGTATG GAGGAGATCG AAGACCCCGC AGTCGTACGA GAAGAGATGA TCTCGGCCTT    8580
CGAGGATGCT TCCAAGGATC TCGCCAGCAA CACCAGCTAC TACGACGCTG AGCGCCGGCC    8640
AGAGGCCATC GGCGTCACCG TCCCGAGAGA GATGCAGCAA CTGCTGGCTC ACGTCGGATA    8700
CCCCAGGCTC TACGTCGACT CAGTCGCCGA GCGCCAGGCC GTCGAGGGTT TCCGCCTCGG    8760
CGATGCCGAC GAGGCTGACG AAGAGCTGTG GCAGTGGTGG CAGGCCAACA ACCTCGACAT    8820
CGAGGCACCA CTGGGCTACA CCGACGCTTA CGTTCACGGC CGGTCGTTCA TCACGATCAG    8880
CAAGCCAGAC CCGCAGCTCG ACCTGGGTTG GGATCAGAAC GTCCGATCA  TCCGCGTCGA    8940
GCCGCCCACC CGAATGCACG CCGAGATCGA CCCCGGATC  AACCGGGTGT CCAAGGCCAT    9000
CCGAGTCGCA TATGACAAGG AGGGCAACGA GATTCAGGCT GCCACGCTGT ACACGCCGAT    9060
GGAGACCATC GGCTGGTTCC GCGCTGACGG TGAGTGGGCT GAGTGGTTCA ACGTCCCGCA    9120
CGGTCTGGGC GTCGTTCCCG TTGTGCCGCT TCCGAACCGG ACCCGGCTCT CGGACCTGTA    9180
CGGCACCAGT GAGATCACGC CCGAGCTTCG GTCGATGACC GACGCGGCGG CGCGCATCCT    9240
CATGTTGATG CAGGCGACCG CCGAGCTGAT GGGTGTCCCC CAGCGCCTGA TCTTCGGCAT    9300
CAAGCCCGAA GAGATCGGCG TCGACTCCGA GACCGGCCAG ACGCTGTTCG ATGCGTACCT    9360
GGCCCGGATC CTGGCGTTCG AGGACGCTGA GGGCAAGATC CAGCAGTTCT CTGCAGCCGA    9420
GCTGGCCAAC TTCACCAACG CGCTCGATCA GATCGCCAAA CAGGTCGCTG CGTACACGGG    9480
ATTGCCTCCC CAGTACCTGA GTACCGCCGC AGACAATCCG GCCTCCGCTG AGGCGATCAG    9540
GGCCGCTGAG AGCCGACTCA TCAAGAAGGT CGAGCGGAAG AACCTGATGT CGGCGGCGC    9600
ATGGGAAGAG GCCATGCGGA TCGCCTACCG GATCATGAAG GGCGGCGACG TTCCCCCGGA    9660
CATGCTCCGC ATGGAGACCG TCTGGCGAGA CCCGAGCACT CCCACCTACG CGGCCAAGGC    9720
CGACGCAGCC ACGAAGCTGT ACGGCAACGG CCAGGGTGTC ATCCGCGTG  AACGTGCTCG    9780
CATCGACATG GGCTACTCCG TCAAGGAGCG CGAAGAGATG CGCCGATGGG ACGAGGAAGA    9840
GGCCGCAATG GGTCTCGGCC TGTTGGGCAC GATGGTCGAC GCCGACCCGA CGGTCCCAGG    9900
CTCCCCGAGC CCCACGGCAC CGCCGAAGCC ACAGCCGGCC ATCGAGTCGT CTGGTGGTGA    9960
```

```
TGCGTGACCG CAGAGGAGTA CGCGGCGGCT CAAGCCGCGA TCACTGCGGG TCTTGCCACA    10020
TACGTCCAGA GGTTCGCTTC GCTCTTCGTC GGTCCAGCTC TCGCTGTAGG TGAGTGGCTG    10080
CGACTGCTGC AGGTGCTGTT CCCCGAAATC AACGGCGGT ATGCAGATGC TGCCGCCTTG    10140
GGCAGGGACT TCTACGACTC CCAACGCGCA CTACACCACC CAGAGCTGCC CCGGAACGAG    10200
AGGTTCCGGG GAGAGCTTCG GTGGGAGTGG TTCGTCCAGA ACATGGAGCC CGCTCGAAAA    10260
GAGATGTCGC AGGCCGACTC TCCGCCGAGT GCGACCTCTA AGTTGGCTCT GGCCGCAGTT    10320
CGCGAAGTGG AGATGGCAGC ACGCCGACAG ATCATCGGCG CTGTCAAGAA CGATCCGGCC    10380
CCGCAGATCG TGCAGGGCTG GGCGAGGGTC GCCACCGGGC GCGAAACATG CGCCTGGTGT    10440
CTGATGCTCA TCTCACGGGG TGCCGAGCTG AATCACAAGG GCAACTTCGC CTACAGCTCA    10500
GCGGAAGCCG CAGGGCTCAA CCTCGATGAC GAGACCGTGA TCGACCTCTG GAACGAGTCC    10560
GGTCACGACC TTGAGAAGTT CCGCGAGGAG ACCAGAGAGG ACTTCGAGAA GTGGCACGCA    10620
GGGTGCGACT GTCTGGTGGT CCCGGTCTTC GATGTGCAGA ACTGGCCCGG AAGAGACGCT    10680
GCCCTACGGG CGCAGCAACT TTGGATCGAA GCCAGCGACG AAGCTGACGA CCTCATTGCG    10740
TCAGGCAAGG CCCGCTCCAA GAACAAGAAC ACGGAGACGC TCAACGCGCT CCGACGCCGC    10800
CTAGCACGCG GCGAAATCAC CATGTCCAAC TACGCCCTCG CTGCGTAGTC CCTCGAACCC    10860
CAGGTGGGTT CTCTCAACAT GCCCAGGAGG CGAAAACACA TGTCCGACAA CCCCACTCCC    10920
GAGAGCACCC CAGAGGCCGA GACCCCGGAG GTCGAGAAGC CGATGGAACC GCAGGGCAAG    10980
GTCTTCGATG AAGCGTACGT TCAGTCGCTT CGCCAGGAGG CTGCAGCCGC TCGGGTGGCG    11040
AAGAAGGACG CCGTAGAAGC GGCAGAGGCT CGAGTGAAGG CCGAGTACGA GGCCAAGCTC    11100
GCTGAGCGCG ACACCGCTTA CACCGAACTG CAGAACCAGT GGGACAGGC GTGGATTGAG    11160
CTGGAGAAGG TCTACCTCTC TCTCGACGCC AAGGTGCCCA ACGACAAGGT TCGGGCGTTT    11220
GTCGAGATCC TCGAAGGCAA CGACAGGGAC AGCATCGCTG AGTCAGTGAA GTCCCGTCTG    11280
GAGCTGGTCG GCGGATTCGG CAACAAGACC CCGAGTCCTG CGTTCGACCC GTCTCAGGGT    11340
CGCGGCGGTA AGCCGCCGAT CCCGCTGAAC GGTGACCCGA TCCTCGAGGC CATCAAGGCC    11400
GCTGTCGGGA TCAAGAAGTA ACCCACCCAA CAGATCTCAA GGAGAGATAA ACAATGGCAG    11460
TCAACCCTGA CCGCACCACG CCGTTCCTCG GCGTGAACGA CCCCAAGGTC GCGCAGACCG    11520
GCGACTCGAT GTTCGAGGGC TACCTCGAGC CCGAGCAGGC CCAGGACTAC TTCGCCGAAG    11580
CGGAGAAGAT CTCCATCGTC CAGCAGTTCG CCCAGAAGAT CCCGATGGGC ACGACCGGCC    11640
AGAAGATCCC GCACTGGACC GGCGACGTGA GTGCGTCGTG GATCGGTGAA GGCGACATGA    11700
AGCCCATCAC CAAGGGCAAC ATGACCTCGC AGACCATCGC CCCCACAAG ATCGCGACGA    11760
TCTTCGTGGC CTCGGCGGAA ACCGTCCGTG CGAACCCGGC CAACTACCTG GCACCATGC    11820
GGACCAAGGT CGCGACCGCC TTCGCGATGG CGTTCGACAA CGCCGCGATC AACGGCACCG    11880
ACAGCCCGTT CCCGACCTTC CTAGCGCAGA CCACCAAGGA GGTCTCGCTG GTGGACCCGG    11940
ACGGCACCGG CTCCAACGCC GACCTCACCG TCTACGACGC GGTCGCCGTC AACGCCCTGT    12000
CGCTGTTGGT CAATGCCGGC AAGAAGTGGA CCCACACTCT GCTGGACGAC ATCACCGAGC    12060
CGATCCTCAA CGGCGCGAAG GACAAGAGCG GTCGCCCGCT GTTCATCGAG TCGACCTACA    12120
CCGAGGAGAA CAGCCCGTTC CGCCTCGGTC GGATTGTGGC CCGTCCGACC ATCCTGAGCG    12180
ACCACGTCGC CTCGGGCACG GTCGTCGGCT ACCAGGGTGA CTTCCGCCAG CTCGTCTGGG    12240
GCCAGGTCGG CGGCCTGTCC TTCGACGTGA CGGATCAGGC GACTCTGAAC CTGGGCACCC    12300
CCCAGGCTCC GAACTTCGTC TCGCTGTGGC AGCACAACCT CGTCGCAGTC CGAGTCGAGG    12360
```

-continued

```
CCGAGTACGC CTTCCACTGC AACGACAAGG ACGCGTTCGT CAAGCTCACG AACGTGGACG    12420
CCACCGAAGC CTGATCCAGG CTTGACATCC ACCGGGAGGG GGCTCCTTCG GGAGCCCTCT    12480
CCTGATGTGG AGCAGGAAGG ACCACATGCG AATCCAGTCC ACCCTCAACG GCGGTTTCGC    12540
CGAGGTTTCC GAGGAGTTCG CCAAGCAGTT GATCGCCACT GGCGGCTGGA AGGTGCCCCG    12600
GAAACCGCGC AACACCAAGA CCAAGACCGC TCCTGAGGAG CCCAAGAACG AGGAGTAACC    12660
CGTGGCCTAC GCGACCGCCG AAGACGTTGT GACGTTGTGG GCCAAGGAGC CTGAGCCCGA    12720
AGTGATGGCG CTGATCGAGC GCCGGCTCCA GCAGATCGAG CGCATGATCA AGCGCCGGAT    12780
CCCCGACCTG GACGTGAAAG CCGCTGCGTC GGCGACGTTC CGGGCCGATC TGATCGACAT    12840
CGAAGCTGAT GCTGTTCTGC GCCTCGTGCG TAACCCGGAG GGCTACCTCT CGGAGACCGA    12900
CGGTGCGTAC ACCTATCAGC TCCAGGCCGA CCTGTCGCAA GGCAAGCTCA CCATCCTCGA    12960
TGAGGAGTGG GAGATCCTCG GGGTCAACTC CCAGAAGCGC ATGGCGGTCA TCGTCCCGAA    13020
CGTGGTGATG CCGACGTGAG CGCGAGCGAC CGACACCGCG CCCCGATTGT CTATCCGCCT    13080
GGCACTCAGG CGGTTACGCC GGATCGGGTC AACGCGTTTG ACTGCGATCA CGAAGCTGAT    13140
CCTCCGGTGT GCCGGTGCGT CCACGACTGG CGCATCGAGT GGGGAAACGT CAAGAAGGCC    13200
ACCGCCAGAT CACGGTCGGC GGTGCTCTGA TGAGCCTCCT CGACACCGGT GCCCGGTACC    13260
AGACCTGCAT CGTCTACCCC GAAGAGATGG TCATCGACTC CGATGGCAAC AAGCGGACCA    13320
GGCCGTCGAA TACCGGCATC CCGGCCATCG CACGGTTCCA GGTAGCCAAC CAGTCTGGTA    13380
CGTCGGCACG ACGTGCTGAG CAGGACAACG AGGGGTTCGA GACCGAGAAG GTCTACCGGA    13440
TGCGGTTTCC CCGCTCGTTC ACCAAGGAGC ACGGCATCCT CGGGGCCCAG TCCCAGATCG    13500
AGTGGCGAGA CCAGCGGTGG GCGCTCTTCG GAGACGCCAC CGTCTACGAC TCATCCCCTG    13560
CGTTGGCGCG GGTCGACTAC ACGATCAAGA GGTACTGATG GCCAAGGTCT ACGCGAACGC    13620
GAACAAGGTC GCGGCCCGGT ACGTCGAGAC GAGGGACGCC GTCCGAGACG AGCGGAACAA    13680
GGTCACCCGT CGAGCCAAAG CCAATCTGGC GCGGCAGAAC TCGACCACCC GCATCACCGA    13740
CGAGGGCTAC TTCCCGGCCA CCATCACCGA GCAAGACGGC GATGTCGACT TCCACACGAT    13800
CCTCAACGCG CCCAACGCGT TGGCGCTTGA GTTCGGCCAC GCGCCGTCTG GCTTCTTCGC    13860
TGGCACCGAC ACGAAACCAC CGGAGGCCAC TTACATCCTC ACCCGAGCCG CCATCGGCGG    13920
CACCGTCTCA TAAGGAGGTC ACATGGCGCG AATGCCTCGC GTCCAGGCAG TAGCGGCCCC    13980
GATCCTCCGG TCAGACCCCC GACTGGAGGG AGTGACGGTC ACGACATGGG TTCCAGACGT    14040
GGACTTCCGA GAGTTCCCGA TGATCAACCT CCGCCGCATA GGCGGGACGA GGAACCCCAA    14100
CGCACCGACG CTGCACACGC TGCCGGTGGT CGAAATGACC GCCTACACCA GAGACGGTCT    14160
CATCGAGACT GAGGAGCTGT ACGAGACCGC GCTAGAGGTT CTCTACGACG CGGTGGAGAA    14220
CGGAACACAA ACTCCCGCAG GGTATTTGAC CTCCATCTTC GAGACGATGG GCGCCACTCA    14280
GTTCAGCTCC CTCTACCAGG ACTCCTGGCG CATCCAGGGT CTGATCAGGC TCGGCGTCCG    14340
CAGACCGAGA ACCACCCTCT AACCGAAAGG TAAAGCCACA TGGCTGAAAA CGACGACGCA    14400
GTGTTGACTG CGGCGGTCGG CTACGTGTAC GTCGGTGCTG CAGGCACCGC TGCTCCTACG    14460
CCGGCCTTGC TCAAGACCAT CGACCTCAGC AAGCCCGAGA CCTGGACCGG TGCTACCGGT    14520
TGGACGAGCG TCGGCCACAC CAGCCGAGGC ACGCTCCCTG AGTTCGGCTT CGAAGGCGGC    14580
GAGTCCGAGG TCAAGGGCTC CTGGCAGAAG AAGAAGCTCC GCGAGATCAC CACCGAGGAT    14640
CCCATCGACT ACGTCACGGT CCTACTGCAC CAGTTCGATG AGCAGTCGCT GGGTCTGTAC    14700
TACGGCCCCA ACGCCTCTGA GACTCCTGGT GTGTTCGGTG TGAAGACCGG CCAGACCAAC    14760
```

```
GAGAAGGCCG TGCTGGTCGT GATCGAAGAC GGCGACATGC GCCTGGGGCA TCACGCCCAC    14820
AAGGCTGGAG TTCGCCGCGA CGACGCGATT GAGCTGCCCA TCGATGACCT GGCTGCGCTG    14880
CCCGTCCGGT TCACCTACCT GGACCACGAA GACGAGCTGC CGTTCTCCTG GATCAACGAA    14940
GACCTCTTCA ACGTGCCCGA GGTTCCCGAG GGCTGATCCC AACTTGACAG CCACCCGGCT    15000
GTCTACCCCG GAGGGGGAGG TTTCCTTGGC GGGCCTGGCC TCCCCTCCT CCCGCCACTC     15060
ACAGACCCGC CGACACTGAA AGGTTCGCCA TGACAAACGT ATTCACCATC GACGCATTCC    15120
GCGAAGAGGT CAAGAAGAAG TACGCTCCGG TCCTCATCGG CCTGTCCGAC GATGTGACCG    15180
TCGAGCTGAA GCCGCTGCTG AAGCTGGGCC AGAAGGCCCG CGAAGCGGTG GTCGAGGTGT    15240
TCAAGGAGTT CGCGGACATC CCCGACCTCG AAGAGGACGA CGACGACGAG TTGGTCGATG    15300
AGTACTCGCT CCAGGTCTGC GACATCATCG CCAAGGCGTT CCGGCTGATC GCCACGAAGC    15360
CCAAGAAGCT GATCGCCGCC TTGGACGAGG AGCCGGATCC CCGTATCCGC GCAGAGCTGT    15420
ATGCAGCGGT ACTCAACACC TGGAAGCGAG AGACGCAACT GGGGGAAGCC GCGCCCTCGC    15480
CGAGCTGATC GACAAGTTCG GCGGGGCGAT CCTCGCAGAC CTGCTCCAGT ACTACCGGGT    15540
AGACCTGCGC GACCTGTTCC GCGACGAGGA TCCGCTTTCG CCGAGATTCG TTCTGTCCCT    15600
GGTGCTCTGC CTTCCCAAAG ACGGCGCGTT CTACGCAGAA CGTCGTGGTG GGCAGCAGTA    15660
CCGGGGCTGG ACCGAGGACC GCTACGCGCT CGCGGACATC TACGACGCCA TCCAGGCGGG    15720
CAACCACATC CTGCTGCTGG CGAATCGTGA TCCGAAGAAG CCAAAGCCCA AGGCACCCAA    15780
GTCATACCCG CGTCCCGACG ACCTAGAGAA GACCACACCG AAGCCGGGTT CGTTCGCCGC    15840
AATGGTCGTG CGAGCGAAGA AGGCGGCTCG AGAGAGAAGG GAAAGGGAGG AGGAGAGTGC    15900
CGAATAGTGC TGGCGTAGAA GTCGCCCGGA TCTCGGTCAA GGTCAGCCCG AACACCAAGG    15960
AGTTCCGCCG GGAACTCAAG ACCGAACTCG AGAAGATCGA GCGGGAGCTT AAGGGCGATG    16020
TCGAGATCAA CGGTCATCTC GATGCGGCCC AGGCCAAGGC CGACTTCAAG CGCATGATGA    16080
TGCAGCTCAA GACCGAAGCT GCCAAGGGCG TTCACGTCCC GGTCGACGTA ACCGTCGACA    16140
AGAAGAGCAA GAAGGGAGGT CTCCTCGGAG GTCTCCTCGG CGGCAGCCGG GGGCTCGGAG    16200
ATCTAGGCGA TGACGCCGAG AAGGCGTCGT CTCAAGTACA ACACCTTGGC AAGTCGTTCC    16260
TGGGCCTCAC ACGAGCCGCC TGGATAGGCG TAGGCATCGT CGCCGTAGCA GCTCCGCTGG    16320
TCGGCATCGT GGCCGGTCTG CTGGCCGGTC TGCCGTCGCT GCTGTCTGCG TTCGGAGCCG    16380
GCGCTGGCGT AGTCGCGCTC GGCATGGACG GCATCAAGGC AGCCGCCTCG ACGCTGGCCC    16440
CGACGCTGGA GACGGTCAAG GCCGCTGTCT CCTCGACGTT CCAGCAGGGA CTCACCCCGG    16500
TGTTCCAGCA GCTCGGCCCG ATGCTGACCG CGATCACCCC CAACCTGCAG AACGTGGCCT    16560
CGGGCCTCGT GAACATGGCC GGGTCGATCA CCGACGTGAT CACCCAGGCT CCTGGTCTGC    16620
AGCAGATCCA GAACATCCTC ACCAAGACCG GAGAGTTCTT CACGGGCCTC GGCCCTGTGC    16680
TCGCTACCGG CACGCAGGCG TTCCTGACGC TGTCCAACGC CGGCGCGAAC TCGTTCGGCA    16740
CGCTCCTGGC TCCCCTGCAG GAGTTCACCA CGGCTTCAA CGACATGGTC AACCGAGTCA     16800
CGTCCAACGG CGTGTTCGAG GGTGCCATGC AAGGGCTTTC GCAGACGCTG GGCAGCGTCC    16860
TCAACCTGTT CAACCGGCTC ATGGAGTCCG GTCTGCAGGC GATGGACAG CTCGGCGGTC     16920
CGCTGTCGAC GTTCATCAAC GGGTTCGGAG ATCTCTTCGT CTCGCTGATG CCGGCGCTGA    16980
CTTCGGTCTC TGGTCTGATC GGCAACGTCC TCGGACGCT GGGCACACAG CTCGCTCCCA     17040
TCGTCACGGC GCTCACGCCG GCCTTCCAGA CGCTGGCGAG CACGCTCGGC ACGATGCTCA    17100
CCGGAGCCCT CCAAGCTCTG GGTCCGATCC TGACTCAGGT CGCTACGTTG ATCGGCACGA    17160
```

```
CGCTGAACAC GGCGCTGCAG GCTCTCCAGC CGATGCTGCC GTCGCTCATG CAGAGCTTCC    17220
AGCAGATCTC CGACGTACTG GTGACCAGTC TGGCCCCGCA CATCCCGGCG CTGGCGACGG    17280
CCCTCGGCCA GGTCGCAGGC GCGGTGCTGC AGCTCGCTCC GACGATCATC TCGACGTTGG    17340
TTCCGGCGTT CGTTCAGTTG GTCCCAAAGG TCGCTGAGCT AGTTCGACC  ATCGTCAACC    17400
TGGTCCAGTC GTTCGCCAAC CTGATGCCGG TGGTTCTGCC CCTGGCGCAG GCTCTGGTCA    17460
GCGTTGCTGG CGCGGTGATT CAGGTGGGTG TCTCCATCGG CGGCGCGCTC ATCGGCGCGC    17520
TGGCGAACCT CACGGAGATC ATCTCCAACG TCATCAAGAA GGTGTCCGAG TGGGTCAGCA    17580
GCTTCTCCAG CGGAGCCCAG CAGATCGCTG CGAAGGCAGC GGAACTGCCG GGATGATCC     17640
AGTCGGCTCT CGCCAACCTG ATGGCCATCG GCCTGCAGGC CGGTAAGGAT CTCGTCCAGG    17700
GCCTGATCAA CGGCATCGGC GGGATGGTCA GCGCAGCGGT CAACAAGGCC AAGGAGCTGG    17760
CGTCCAGCGT GGCTGGTGCA GTGAAGGGCT TCCTGGGCAT CGAGTCCCCG TCGAAGTTGT    17820
TCACCGAGTA CGGCCAGTTC ACCGCCGAGG GATTCGGCAA CGGCATGGAG GCAGGGTTCA    17880
AGCCCGTCAT CGAACGGGCC AAGGATCTCG CGGCTGAGCT GTCCAGGGCG ATGGAGTCGG    17940
GCACCGACCC CTCCGGGATT CTCGCTGGGC TGGATCAGAA TGAGCTGAAG CAGATGCTGG    18000
CGGCTCTCGA AGAGGAGCGC AAGCGACTCA AGGTCGAGAA GAACGGTATC CCCAAGGGAG    18060
ACAAGGCAGG CCGAGAGGCG CTGCAGAACC AGCTCGACCA GATCCAGGCG CAGAAGGACA    18120
TCCTGTCCTA CCAGCGTGAC CGCATCAAGA ACGAGTCTGA GTACGGCGAC ATGGCCGGCG    18180
AAGACCCGTT GGTGAAGGCA GCCTCCGGGC TGATGAGCGC ACCGGTCGAC TTCGCGAAAG    18240
CGACTGGCAA GCAGTTCCTT TCGGACATCG GCATCAGCGG AGATGGGTTC ATCTCGAAGG    18300
CCATCACCGA GGGCATCCAG TACATCTTCC AGATCGGCTC TGTCGATGAG GCGCTGTCGA    18360
TCAAGGACCG CGAGGAGTCG AAGAACGCGC TGTCCGTCGT TGGCCGCTGA CTTGACATCC    18420
ACCAGGAGGT AAGCATTGAT CACCGACACC ATCGTTGAAC TCGAGGGTGT CAATGGTGAG    18480
CGTTTCAACT TGACGACCGG TGACCAGGGT GTGTACCTGG CCACAGACGT GGAGGGTTGT    18540
TTCTACGACC CTCCCGTCAA GGTCGTTGTT GAAGAGCCGG GGAACTACCC CGGCGCTCGC    18600
TACTTGTCCC ACCGAGCCCT GAAGCGAGAC ATCGTCTTTG GGGTCGTCAT CCTCAACGAC    18660
GCGAAGCAGG GGCCGCGCTC CTGGCTGTCG CGAGACTCCG AGTGGCGCAA GGCGTGGGCG    18720
TTCAACCGCA CCTGCAAGCT CTACGTCACC ACCCCGGACT CCGGTACCCG CTACCTGAAG    18780
CTGGCGCTGT TCGAGTCCCC CACCGTCAAG ATGGACACCG ACCCAAGAGG TAAACCCCTT    18840
GAGGTCACGG TGATGTCGTG CATCGCGTAC GACCCGTTCT GGTACGAGGA CGACAAGGTC    18900
TTCTCGGCCA AGACCAAGAC CGACACCCGG TTCGACCCGT CGTTCTGGAC GCCGCCGTGG    18960
CCGTGGGAGG AACTGCCCAA GGAGACGCTG CGGATCAAGG TCGGCCGCGA GCAGGGTGGG    19020
CTAAACCCCA CCGACCAGTA CATCTTCCCG AAGTGGACCG TTCCCGGCTC CACCGAGAAG    19080
GTGCCGAACT TCCCCTGGCC GTTCCCCCCG AACGTCCCGA TCCCGTGGGA GACAGCACCG    19140
TTCACTCAGT TCGTCATCCC GGACTACTCG TTCGAGGATG AGGAGTTCCG CAACCGCCGG    19200
CTCAAGACGC CGGGGTTGAT CTACGGCGAG AACTGCGTCA TCGACACCGA CCGGCGCGAG    19260
GAGCAGATCG CTTCCGAGTC GGGCTCCCCG GTGTGGGCTC GGATGAACGG TGTCCGGTTC    19320
CGCAACTCGA TCCCGCCCTA CACCGAAGAG GCTGAGTTCG TCATAGACGC ATCGGGATGC    19380
GCTCCGGGAC AGGTAGTTAC CCTCCGGCTC ACGAGGCCGT GGTCGCGCTG CTGGGGGCTA    19440
GAGTGAGTGG TCTGACGAGC GTTCGTGAGG CCGAAGATCT CTGGCAGAAG ATCCAATTGC    19500
GGCGCTGCAA GCGCGAGCAG GAACGGCTCA AGCATCCCGA CGTAGAGCTG CGCGATGGCG    19560
```

-continued

```
ACTTCCGCCT GCGCGGCCTG GTCGCTGGCG AGCGGGTGCT CGAGTGGGAG TTCATCGAGA  19620
ACGAGACTGG CACCTGCACC TTGCAGCTCT CACTGAGCCA TTACCTGGCG AAGTGGGTGA  19680
TGGACCACCG GGGTCGAGCA AAGCGCAACG TCATCATCAA CATCGAGAAG CAAGGCGCTC  19740
GATGGACCGG GATGATGGAC CACTACCGGG TCATCAAGAC CGACGCAGGG GACGCCTACA  19800
TCGAGATCGT GTTTTTGCAC GACTTCGAGC AGACCAAGCA TATCCGGGTA TGGTGCAACC  19860
CGTTCCTACG CCCCGAGCTG CAGTTCCCCA AGGTGTGGAT CATCTTCGGG CCGGCCAAGT  19920
GGTGTTTGCT GGTGACACTG TTCGTCAACC TGCTCAGGCT CGAGACGAGC TTGTGGACGC  19980
TGCCTGATGA CCCCACGGAC ATCAACGAGT GGATGGGTCC GAGCTTCAAC CCAGCAAATT  20040
GGCGGAACAT CGTCAAGCCG TTCCCGTTCC TGGCCGACAA CTCACCGGTC ACGATGGTGT  20100
TCAGCCGGTT CGGGACGTTC TACGACACCG CCAAGAAGAT CCTCGAAGAC CATCAGCTCA  20160
CGCTGACGTG TCGTCGGTAC ATCAAGGACC GCGACCCGCA TCCGTTCGAA GATCTCAAGG  20220
GGCTCTGGGG AATTGATCCT GTCGAAGACC TGCTGCAGAA GATCCCGCTC CGGGACGGCT  20280
GCGTGGTCTG GGACATCGAG GACAACTCAG GTTGGGGCAC TCAGACCGCG TTCGGCGGTT  20340
CGTGGCTGAC CGGGTTCGTC CGAGGGATGG TCCAACTGGC CGGCGACGGC CAGGTCGAGG  20400
GCGTCGATGT GTTCACCGGG GACTACACGT TCCCAGGCGA GTACTACTCC CCCTGGTTCA  20460
TGGGCACCAG CCCGATAGCA CCCCACGTCG TGTTCGAAGA AGGACCGCTG ACCGGGATCA  20520
AGTCGTCGGA GTTCTCGTAC TACGAGGCCA CCGACACCAG CTTCCTGGCT GGTGGACAGA  20580
GCGCACCTGG CATCAACGAG GGCATCTCGG CCCTGGTGAA CATCGGTGGC GACCTGCTGA  20640
CCTCGTTCAT CAACAGCCAG CTCGCCGCGC TCGGCGCGGT CGGTGGAGCG ATTGACCTCC  20700
CGCCTCTGGG CGGTCTGCTC GATGCGGTGT GCAGCCTCT GTACTCCGAT GTGTTCGGCG  20760
CGTTCATGGA AGTTCCGACT CTGCGTGCGA TGGGCATCTC GCTCCCGATC TCCGGGCTCG  20820
AGGACATCGT CACCGGACTG GGCGACTTCC ACTACTTCGA GAACATGGCC GACGGGGCGA  20880
TGAAGGCGTT CACGCTGTCA GCGTTCGCAG CCATCGCATC GCAGATCCAC AAGACGAGGG  20940
CTCGAACGAC CCACACCCTC AAGGTGTCTG ACGCCGCTCC GTACATCTTC GCGCCAAAGC  21000
CCTACGGGCA CTGCTGGATC GGAGATCGCG TCGGCACGTC GGTCCTCGGC TACCCGGTCG  21060
AGCACCAGTT GTTCGTGGAG CGCATCCGCA AGGTGAAGTA CCGCATCGAC AAAGACGGCA  21120
TGAAGCCGTT GGAGATCGAG ATCGGTTACC GCGAACCGAA GAACCCAGCA CTACACATCC  21180
TCGAAGAGAT CAAGCGCGTC AACGGCGCTC TTGGCACTGC GGGGATTCTC TAAACCGAAA  21240
GGCACGCCGC ATGATTCCCT CACAAGAGTC TCACAATCCG AACGACCCGC GACAGCACGT  21300
CATGTGGGCG CTACGCAATC TCCCGATGAT TGCTGGCGTC GGGGCGATCA CGCATCCGGG  21360
TTACCTGGCG GATTGGTCAG AGCACTTGTG GAAGTGCGGC TTTCGGCACG TCGACTGGCT  21420
CCGGGAGCTG GCTGATGAGG ACGGCAACAT CCACGTCAGT CAGCTTCCTG ACCAGGAGAT  21480
CAAGTTTCAG CAGCCCTTCC GGGGCCAGCG AAGCGACTAC AACAACGCAG CTCGATGGGT  21540
CGGCAAAGAC GATCCTGACC CAGAGCCCGT GCGTATTCCA GACATTCGCA AGCTCACAGA  21600
CCAGGAGAAC AGAGCGATGA TCGCGCAGTA CGAACGAGAC GGTTGGATCA AGGATGGATC  21660
CCCCGGCCCA GCGATAGCCG AGGTCGTGGA GTGACCCCGT TCAACCCAGA CTCCATAGGC  21720
GACTACGTGA CACTGCTCGG CGTTGCGTTC CTGACCTTCT CGGTTCCCGC ATGGTTCACC  21780
GGACGAGCAC GCAAGCACAG CAGTGACATC GGCGAAATCA AGGAACAGGT ATGTAACACC  21840
CACGACACGA ACCTGCGCGA TGACCTCGAC AGCGTCAAGG CAGACATCAG CGACTTGAAA  21900
GAGATTGTGT TGCAAGGGTT CCACCAGGTG AACGAGTCGA TCAACCTCGA GCGCCGTGAG  21960
```

```
CGGATCGAAG GAGACCGCCG AAAGGAGGTT GCGTGACCTA CCCCACCAAC CCACTAGAGG    22020
CCATCGGCGC TGACGGCGCA TTCGAGATCG GTGGGGGCGA CTGGAGCTTC GGCCAGGACT    22080
ACACCGAACA GGCCATCCGG GCTCTGTTCA CGATGCCAGC GGTCACGATG GAGAACGCTC    22140
TCGGCCTGCT CGAAGAGCAC CTGCTGAAGC TGCCTCTGGA GGCGCTGCAG GGCTTCAAAG    22200
ACATGATCCC GGACTGGGTC GAAGGAGCAT TCGACACGGT CACCGGCGCT GTGCAGGCGA    22260
TCATGAACGC GCTCCAAGAC GGCCCGCTGT TCCTGAAGTT CGCCGAGTTC CAGCTCTTCC    22320
TGCAGCGTCT GCTGAACAAC CCGGCCGAGG TCATCGGCGA GATCCCCCAG ACGTTGATCG    22380
ACGGCCTACA GGACGCGCTC AACACCGTCA CAACACCAT CCAGACCATC GTGGACATGC    22440
TCCTGCAGGC GCTGGGCATC ACCCCGGAGG GGGAGCTGAT CGACCGGATC TTCGACCTGA    22500
GCGATGAGAT GGAGTGGCTG CAGACCGCAG CCTCGAATGC AGCTACCGGC ATCCAGGACA    22560
CCTGGAACAA GTTCTGGGGA GCCCTCACCG GGCGCGTCCC AGACCAGGAC CAGACCGTCG    22620
CTGAGCCCGC CGAGCGTATC GGCGAGCTGG CCGGCACCAC GTCTGCTAAC TCGTCTGCCA    22680
TCGCGGAGCT GCAGCGTCGA CTGGACAACC AGCAGAACGC TGGCGGCGTG GCCGGCGGTG    22740
ACGACTTCGA GCGACTGAAC ATATCCGGTT GGGACATCAG GTATTCCAAC GGATCCAGCG    22800
GCCGAGGGTA CTACCGTGCC GACGGCCACC AACTGGTCTG GATGGACGAA GGCAACCAGC    22860
AGAACACCGC GACGTTCGTC CGCACCAACC CCGCAGACGA GAAGACAGCC ACCGACTACC    22920
AGAAGATGAC GTTGGTCGTC GGGACTATCT CCGGTGAGGT ACAGACCGTG TTCCCGCCGC    22980
AGGGAGGTTC GCACACCCGG CTATGGGTCC GCGTCAACGA CAACGCTCCG ACCGTCGGCA    23040
TCACCGACGG CGTGTTCGTA GAGATCGGCG GCGTATCGAA GGCCCAGATC GGCTACCGCC    23100
GCAACGGCAA TGACACGTTC GTCGGATCTA TGGTCGACTG CACCTGGGGT GCTGGATCGA    23160
TCTTCGCTCT GACCGCCGGC ACGGCCAACG GTGCTGAGAA GTTCGAGGTC TCGAAGAACG    23220
GCCCCGTGCT GGCCACATGG TCGGACGACG GCGTCGTCTC CGCGATGGGT GCGAACTACC    23280
GCCGCTGGGG CTGGGAAGGC CAGGCTCGTA ACCGCAACCT CGGCCAGGGC ACTCCGAACT    23340
CGGTCACCCG AGTGACGATC ACCGACAACG ATCCTACCGG CGCAGGCGGT GGAGCTGTCA    23400
ACGTCGGAGG AGATGTCGTA GGTGTACTCC CCATAGAGAA CGGAGGCACC GGAGCTTCGA    23460
CAGCTTCGGC AGCCCGTACC GCTCTCGGAA TCGATGACCT GGTCGAAGAT ATGTCCGACG    23520
TAGTTCGTGG ATCCGTCGAA GGACTCCCGT TGATACCGAA GATCTGGGTA GGAACAGAAG    23580
CTCAGTACAC GGCTCTCGCC ACCAAGGATC AGTCCACGCT ATACTTCAGG ACCGCTTAAT    23640
GACTGGTATC TCGTTGGGTG TCAACGACAT CCGCAACCTC TCGATATTCT TAGGCGTCAG    23700
CAACAAGATA TTGAAGGTCA GTCTAGGCAC AGAAAAGGTC TGGCCTGCGT TCACCCCGGT    23760
GCTGACCACG TTCGCCACGG TCGGCACGTA CACCTACAAC ATCCCCGACG GGGCCAAGTT    23820
CATCGACGTC ATCCTCCTCG GAGGAGGCGG CGGGGGTAAA GGCATGGCCC TGGCTGACGG    23880
CTGGGGCAGA GGTGGAGACG CCGGAAGCTG GCTATCGTC ACTCTCGAAC GCGGGGTACA    23940
CATCCCGTTG TCGACCAAGA CGATCACCGG GCTCGTCGGA GCTGGAGGCG CAGCGGGAGC    24000
TGGCTCTGTA TTCTCAGGCA AGGCCGGAGG CCCTGGAGGA AACACCACGG CGTCCGCTGT    24060
CGGATGGTCA GGTTTGACCG CAACCGGCGG TCCCGGAGGC TCTGTGATCG ACATCCTCAG    24120
CGTCGCCGGA AAGTCGCCTG GAGATCGGAC CTACAACGAC CAGCTCTACA TAGGCGGCGC    24180
ACAACAGAAC TCAGCTGGCG GGAACGGCAA TGCTCCTGGC GGCGGCGGGG CTGGTGCCCA    24240
GGTCTCCGCA CAGAGCGGCG GTGCTGGCGC TCGCGGCCAG GCGTGGTTCT TCGCGTACTG    24300
ACAAGAAACC CCCCTCTTTA GGACTCAGTG TCCTTGGGAG GGGGGCTTTT TGCGTTTCAG    24360
```

```
GAGGTCTTGG CCAGCTTGGA CATCGCCTCA GCGATAGCCT CGTCGCGGGC CTCAGACGCC    24420
ATCTGGTACT TCATCGCCAT CCTAGGAGTC GTGTGACCGA GACGGGCCAT CAGCTCCTTG    24480
GTCGTCGCAC CTGCCTGAGC GGCGAACGTA GCGCCGACAG CGCGGAGGTC GTGGATGCGG    24540
AGTTCCGGCC GACCGATCTT GGCGTAGCCA CGCTTCAGCG ACTTGGTGAA CGCGGACTTC    24600
GACAGCCGGT TGCCCTGCGT CGTGGTCACC AGGAATGCCT CGGGGCCCTT GTTCATCTTC    24660
GTACGGTCCT TCATGTGCGC TCGGATCATC TCCGCGACGT GAGGCGGAAC CGTCACAGGA    24720
CGCTTCGACC GGACGGTCTT GGCGTTGCCA CGACGATCT  TGTTCCCAC  GCGGGAAGCG    24780
CCACGGCGCA CCCGGAGCTT CATCGTCATG CCGTCGTCCA CGATGTCCTT GCGGCGAAGC    24840
TCGATCAGCT CTCCGAACCG GAGGCTCGTC CACGCCAGGA TGTATGCCGC GATCCGGTAG    24900
TGCTCGAAGA TCTCAGCGGC GACGATGTCC AGCTCCTCAG GCGTCAGCGC CTCTACGTCG    24960
CGCTCATCGG CTGCCTTCTG CTCGATCCGG CACGGGTTCT CTGCGATCAG CTTGTCCTCG    25020
ACCGCTGTGT TCATCACCGC CCGGAGGACG TTGTAGGCAT GCCGGCGGGC AGTCGGGTGC    25080
TTCCTACCCA TCCCGGCCCA CCACGCACGC ACCAGAGCTG GCGTCATCTC TGTGACCGCC    25140
ACTTCACCTA GCACCGGGTA GATGCGGCGC TCCGCGTGCC CGCTGTACAG ATCCCTGGTG    25200
CCGTCTGCGA GGTCGCGCTC CACGAGCCAC TTCCGGGTGT ACTCCTCCAG CGTGATGGCG    25260
CTGGCGGCTG CCTTCTTCGC CCGGTCCTGT GGAGGGGTCC AGGTCTCCAT CTCGATGAGC    25320
CGCTTCTCGC CCGCGAGCCA GGCTTCGGCG TCCATCTTGT TGTCGTAGGT CTGCAGCGCG    25380
TAGTACCTCA CACCGTCCTG CGGGTTGACG TATGAGGCTT GGATCCTCCC GCTGCGCTGA    25440
GTCTTCAGCG ATCCCCATCC GCGACGTGCC AACTAGGTCT CCTCTCGTCG TGAACAAGGC    25500
TACCGGGTTG CAACTCCTGT GCAACTCTCA GGCTTCAACG CGCTTCTACG ACCTGCAATT    25560
TCTTTCCACT TAGAGGATGC AGCCGAGAGG GGGTAAAAAC CTATCTTGAC CGGCCCATAT    25620
GTGGTCGGCA GACACCCATT CTTCCAAACT AGCTACGCGG GTTCGATTCC CGTCGCCCGC    25680
TCCGCTGGTC AGAGGGTGTT TTCGCCCTCT GGCCATTTTT CTTTCCAGGG GTCTGCAACT    25740
CTTGTGCGAC TCTTCTGACC TGGGCATACG CGGTTGCAAC GCATCCCTGA TCTGGCTACT    25800
TTCGATGCTG ACAAACGAAT AGAGCCCCCC GCCTGCGCGA ACAGACGAGG GGCATTCACA    25860
CCAGATTGGA GCTGGTGCAG TGAAGAGAAT AGACCGGGAC AAGGTTGCAC CGGGAGTTGC    25920
AGCGGTCGGA ACCCTCGCCG TCGGCGGGCT GGCGTTCGCC CTGTCGTTCA CGGCTCTCAG    25980
CGAGCTGGCT GCGGCCAACG GGGTGGCCCA AGCAGAGATG GTGCCCTTGG TGGTCGACGG    26040
CCTGACGCTC GTCGCCACGG TCGCCACAGT GGCCCTCAAG CAGAACAGTT GGTACGCGTG    26100
GTCGCTGCTG ATCCTGTCCA CCGTCGTATC GGTGGCCGGC AACGTGGCAC ACGCCTACCC    26160
CCACGGCATC ATCGCGATGG TGATCGCTGC GATCCCTCCG CTCTGGCTAC TGGCGTCGAC    26220
CCACCTAACC GTGATGCTGG CGAAGCAGCA CTCGGAGCAC GCCGAAGTAC CTGTCTCGCG    26280
GCCAGAACCC GCGCCTCGGG GCCTGGAGCC CGCTGCCGCT TGACTGCGCC CGACCGGGAC    26340
AGAAATACAT AGAGAACCTA TGGATGTAGG AGGCACAAAA AAATACCCCC CGAGCCAGCC    26400
CGAAGGCCAG CCCAGGGGGC ATGGTTCTGC TTCAGTAGAC CTTGCGAGTC CGACCCGAGT    26460
TGATCATCGC CATGATGACC CAGACGGGCA ACCACATTCC GCAGGTGATG AGCGAAAGCA    26520
ACAGGTGCAT CGCGTGGTTC GTCCTGACAG GCATGACAGT GGGCTGCGGC ATCGGAGGAG    26580
GCGCGACCGG GTACGGCGAG CCCGCGTACC ACTGAGGTCG ATCTTGTTGG GGCGGATACT    26640
GATTGGTCAT CCCGACAGCC TACTTGCCGA TGGGTCGCAT CAGCTCCTCG ACCGACTCGC    26700
GCTCCACGCG GATCAGCCGG GGACCGAGCC GAACGGCCTT GAGCCGGCCG TCGGCGATGT    26760
```

```
AGTTGCGGAC GGTCTTGGTG CTGACACCGA GGTAGTCAGC GGTCTCCTGG ATGGATGCTC  26820
TCGGGGGCAT CAGCGCGGTC CTCCGTGCTT CATCGGTTGT CTCCCGAACC CTGGATCACG  26880
CCACGATCCT TGCGGCTCTG GAGCTTGTTG AGGTTCCTCT GGGTGACGGT GCTCAACCAG  26940
ACATCGAGCT GGTTGGCTAG CTGGGCGACG TACCACATCA CGTCTCCGAG TTCCGCCTGG  27000
AGGTCGTCTC GGTTCTCCTG GGTGATGACA CCGTCTTTAT CCCGGAGGAT TTCTTGACC   27060
TTGTTGGCGA TCTCGCCGGC TTCGCCTACG AGACCCATCG TCACGTAGGA GAGACCCTCG  27120
ATGCTGTCGC AGTCGCCTGC ACCGGGGTAG ATCGCTGTGT CGCTCGCGGC GATCTGGTAG  27180
ATGTCGACGT GCATCAGATC ATCACCGGGA ACAACTGGCC ACCGGGCATC TGGATGAACA  27240
CCGGGACGCT GGGGGTGTAG TCCGACGAAC CCGTGCCGCC CTCACAGGCG GACAGGCTCA  27300
GGGTGGCGGC AAGGCCGATG ATGGCTGCTG CGATGGTCTT CTTCATCTGT TGCTCCAGTA  27360
GCTAAGTTCG GACTCCAGTT CGCGGATACG CTCCTGTAGC CCTTGGTTTT CCAGGTACGC  27420
CTCGGCGAGG TTGGCCTCGG CGCGGTCACG GGCCTCGTCC TTCGACGTGG CCTCATCGAT  27480
TGCCTCGTGT AGCCGGCGGA TCAGATCTGG GATGGCACCG TGCAGACCGC ATATGAAGTC  27540
GGCGTCTGCC TCGGAGAGGT GGGACGCCAC CAGATCCTTG TCCTGGGTCT CCTGGTTGAC  27600
CGCCCAGATG ACGTGATCCT CTAGCCCGTG GTCGGTCTCG CAGATAGAAG GCGGTTCTAC  27660
CTCCTCTGGC ATCCAGTAAG TCTTCTCAGC CCCGGTGGAC TTCGCCCACT GCTGGTAGAG  27720
GATGTCGAAG AACTCGTGGT CCTGTTCGTC GGCGGTAATC ACAGATCGTC CTCTTCATCC  27780
CATTCGTCGT AGTAACACGT ACAGCCGCAG CAGGTGCAGC AGCCGCACTC GTAGGTGCCG  27840
TAGTCGTAGT CATCCCAGTC GTCTTCGTCC ATCTAGCTGT ACTCCTTCAT GATTCGGTCG  27900
AACGCACGCG TCTGCACGCG CATCTCCAGG TCGACCGTTC GCTTCAACCA CGCCCATTCG  27960
CCGTCGTGGT TGATCTCCCA CTGGCTCTTG AATGTCGCTG TCTCAACGAG GAACTCGACA  28020
GTCAACGTGT GCAGTCCGTT GTTGCTGGGC TGGAATCCGA TACCGTCCTC AGCGATGTAC  28080
CAGGGCAACT CCTGGCCGTC GAAGTAGACG GCCTTGTCGG TCACCAGTAC TTCAGGGAAG  28140
GTGTGCTCGG TCAACGGCGT CCCAGGTATG GGATGACGCT GGCCCGGAAC TCAAGGAACA  28200
CCATGTTGTC CGGGCAGTCC TCGGGGACGT TGTCGGGGCG TTCGGCGGTG TAGACGCCGA  28260
TCTCGTTGCC CTCCAGGGTT CCAAGCTCGT TGAGCTTGTA GATCGCCAGA CCCATCAGCT  28320
CTTCATCGAG ACCGTTCGGT GCTGGCAGTA CAACTTTGGC TTGTGGCATT AGCCCTCCCT  28380
CGGAATTACG TATGCGCTGA ACTCGACGGC CGTAATGCCG TCTGGCAGTT GGAATCCGAA  28440
CCGCTCTTCG AACTCCTCGT TGGTGATGGG GCCGTACTCG AAGGTTCCGG GCACTACCTC  28500
GCCCTCCCCC TCGATCAGGA GGTACGCACC GGCGGCGTAC ACCTCCTCGT CGTTCGGCCA  28560
TCCGACTACG GTCCCGAGGA CCGTGAACTT CCTCGGCTCC ATCAGGGCAC GTCCACTTCG  28620
TTGATGAGGA ACCGCATCGG AGGTGGAGTG AGCATTGCCT CGGCTATGGC GATGAGGGCG  28680
TTCAACTGAC CCTTCAGCAG CTTCTCCTCG TCGCCTGCGG GAAGGTGGCG CACTCGGCGC  28740
TCCATCTCCT TGGCGCGTTC CAGATATTCG GTGGCTGTCA AGTTGTCCTC CTTAGTAATC  28800
AGCGCCGTAG AGCGAACCCC ACGAACGCTT TCCGACCTCG GGTCGGTGC CAACCAGCAC   28860
CGGACCCATC TGTTCTTGCA TCAGGTGGCC AATGTGTGCA GCGGCTCTCT CAGCCTCTGA  28920
GGCGGGCAGA GACGCGACGA TCTCGTCGTG GATAGGCAAC CGTAGGTACG GGTGTATCC   28980
GGCCTCGTGG AGGCGAATCA GAGCCCGACA GGTCACGTCC CGCGACGACG ACTGGATCAT  29040
GTAGTTCAGC GCGGAGTATG TCCGCGAGCT GTCCACCGGC AGCCGCCGGC CCATCGCGTT  29100
GACGATGTAG CCGTTGCGGC CAGCTTCCAT CGCCAGCTTC TTGCTCAGCC GCTCCACACC  29160
```

```
GGGGTATGTC GCAGAGAACG CCTCATGAAC TCGCTTGGCC ACAGGGATCG AGATCCCCAC    29220
TGCCTCAGCG AGAGCCTTCG CCCCACCGCC GTAGACCTTC TGAAAGTTGG CGGTCTTCCC    29280
AACCTTTCGC GGCACCTGGG CTGCGTCAGC GGTCATCTGG TGGAGGTCCG CACCGTTCTC    29340
GAATGCCTCG ATCATGTTGC GGTCGCCCGA CAGCGCCGCC AGGACGCGAA GCTCCTGCGC    29400
CTGGTAGTCG ACTGAGGCCA TCACATCGCC TGGCTCAGCG ATGAAGCATC GCCGCACGAT    29460
CCAGTCCGAC GACGGCAGCG TCTGCGCCGG GATGCCGGTG ATCGACATGC GCGAGGTCCG    29520
CGCCTGCAGT GGGTTGATGA ACGTGTGGCA GCGGTCCTCA GAGTCCCTGG TGTCGATGAA    29580
CTTCTGGACC CAGGTCTTCC GCCACTTCCC CAGCTTCTTA GCCTCCTGAG CGATGGCGGC    29640
AAGCTCGTTG CCATCTTCGA CCAGCTTGTC GAGCAGAGCC GCGTTGACCT GGCGCTTGCC    29700
AGTCTCGGTG CGACCGGTGA TCTTGACGCC CATCTCCTCA AGCCCCTCGG CCAGATCCTC    29760
GGTCGAGTTG ACCTTCTCCA CGCCGTACTC GGTGAAAGCG ATTGCCTCCC AGACCTCCTG    29820
ATCGGCCAAC CACTTCTCGG CGAGCGACCG CGAGTACTCC ACATCGAGCA GGAAGCCCTG    29880
CCTGTCGATG TAGCTGCAGA TCTCACTGAT CTTGTGCTCG TACGGCACCA GCGACCGACT    29940
CACGTCGGGC ACCAACGGTG TCAGGCTCTT GCAGACCCTC GCGGTGAAGA TCGTGTCCAT    30000
CCCGGCGTAC AGCAGGTACT CCGGGTGGAA CAGGTCGATG GTCGACCAGA TCTTGGCCTT    30060
GGTCGTCTTG TGCTCGGCGG CTAGCTTGGC CATGAGCTTC TTGACGTTCT CGGCCTGGTC    30120
CTCGGAGATG AACTTCGCGA TCAGCTCTTC GAGCGAGTGC CCGAACCCGC CGGCCTCGAA    30180
GGGCCGGGGG TCCACCAGCT TCGCCAGGAT CTGCGTGTCA AGCACGCGGG CCACAGACC    30240
CTCCATCTCG ATCCCGAAGC ACTGGTCGAG CACCTGGAGG TCGAAGGAGG CGTTCTGGAG    30300
CACCATGCGC TTGAGAGCGC CGATGGCGAT CCGCACGTCC TCGATGAACA CGTCTCCCAG    30360
CTCCACCGGC ACCACCCAGG CTTCGTCCTG AGTACCGAAC TGGACGAGGC GGCACTCGAA    30420
GGTGTCGCTG TAGATGTCCA GCCCGGTGGT CTCAGTGTCG ACGGCGAGGC AGTTCAGGTG    30480
AGCCCGGATG AAGTTGCGGA AGCCTTCCAG ATCCTCTGGG GTTTCAACGA CGTTGACGGT    30540
GACGAGGTCT CCCTGAACCT CATGCCGCAG CTCGATCAAA ATGCTCTCCT ACTGGAAGTA    30600
CTGAGGCGGA ATCCAGGTGG CTGAGGCCAT CTCCTTGATG GCCTGCTGCA TGGCCGCTTC    30660
GAACGGACAG TCCGGGTCGA TGTCCGGCTT GTAATGGGTG ACGATGATCC GGCTGTTGCC    30720
GCCGAAGTCG TGGCTGACCA AGCCCTTTGG GGGCAGCTTC TTCAGCGCCT TGATCAGTTC    30780
CTCAACCGTG GTCCCGGTAG GGGCCTTGCC GTCAGGCAAT GCCTCCCCTC CGTACGGCAC    30840
GTCCAATGGG ATCGTGTACC GCTCAACGTC TTTGATCTTC ATCGAGCCTC TTCCTCTTCG    30900
ACTACCTCGT CTACCCGGCG GAATAACTCC GCTAGTTCTG CGGGTAGCAA TACTGGGTAC    30960
TTCTCTCGGG CTTCCTGCAT CGCTACCGCG ATCCCAATCA GGGCAGCGAG CAGTTCATTG    31020
ACGGAGTACG CCAACAGCTC TTCGCGGATC TCTTCTCGGG TCATTAGTGG TAGATCCCCC    31080
GGACGGTGCG CGAGATCGTG GCAGGGTTCA CGCCGTAGTT CTCGGCGAGA TCCTTCTGCT    31140
TCATACCGCC CAGGTACGCC TGGCGGATGT CCTTGACCTC GCGCTCGGTG AGCTTCTTGC    31200
GGTTCGGCCG GCTCGGGCCG GTCTCAGGCT TGACCTGAGC CAGCGCCTTG CCGAACAGCT    31260
CGTTCTGCGT CCGCTGCTTG ATCGCGTACC GACGGTTCGC TGCAAGCACC TCGTTGAGCC    31320
GCTGGGACAA CTTGACATTG GCCTCACGCA CTACCTCGAC CTCTCCGAGC AAGTTCGTGA    31380
TCCGGTAGTC CTTGTCCTGG TTCTCGATGG CCAACCGGTT GTTCTCCTCG GAAAGCATCG    31440
AGACCTTGTA TTGCGCCTCT CCCAGCGCAG CTTTCAGGTG CTTCTTCCTC ATTCAGCGCC    31500
CCTCTCTCGG CGGAACTGTT CGTACTCGTC TTCGGTCATG TAGTAGTAGT AGTCAACGAC    31560
```

```
CTTGTCCCAG TTGAAGGTTC GGGACGTGCC GTCATCGAAC GCGATGATCA GGACACCCTC    31620
TTGGGTGTCT AGGATCGGCT CGCCAGCCAC GACGTGGAAG CGGTCCTCGA GGGTCACCGC    31680
AGTCGCTCTG CGTGCCATGT CAGTTCCTCT CAGTAGCTGT AGGGGACATC CGGGATGTCC    31740
TGGTAGGTGT TGGGTGCGAT CTGTCGGAGC TGCCGAAGCA ATTCCCTGC CAGCTCACGG     31800
ATCTCGGCAT CCGCGGCCTC GTGCCAGCGG GCCTTGATGA CGTACCGCCA CGCCCGATGG    31860
TTGCCCGTGA CGACCATCGG TGAGTTCGTC ATGTTCGGCA GGACAGCTCG CGCTGCCTCG    31920
CGGGCCTGCT TGCGCGGCAA GCCCCGGTCA GCCAGCCGGT TGACGATGTG TTCGTAGACA    31980
GCGTCAATCT CAGAGCTGAC GGACTCCATG ATGTGGACGA GGTCGTCTCG GTCGTCGGGG    32040
TGGAGCTTGA ACAGAGCCGG GGGCAGATGG ATGCCAAGGT CGGTCGGATC CACATATCGC    32100
TGAGACACCA CCGAGAAGCT CAAGTGACGG TGACGCTCCA GCTCGGTCAG CACCGACCTG    32160
CTGGCCTCGA TGTAGAACGT CGCCGAGGCG TGCTCGAACA CGCTCTCGTG GCCCAGATCG    32220
ATGATGTGGT TGAGGTAGTC CTCGTTCTCG GCAGTTGCCG GGTTCGGTCG GTGGAACGAC    32280
CGGTAGCAGT TCCGGCCCGC GAACTCGGCC AGCTCGTCGG CATCGAAGTC GCCGAAGTAG    32340
GGATCTTCGT CCTTGGATTC TTCGAAGTCA TCGACCTCGA ATCCGATGTC CCGCAACGCA    32400
CCCGGATCGA TCTCGGTGGC AGCGATCAGT TTGGCTTTCA TACTCTCCGC TCAGAGTTGG    32460
TGGAACGAGG TCAGCCAGGG GGCAGCGAAG CCCTTCTACA GCTCCCCTTG GCTCGTTACC    32520
GGCTTCTCGA CCTCGGTGGA TGTCAAGTAG TCGAGATGAC TACTTCTTGT CGGGCCATTG    32580
CGCGTCACAC TGCTGATCGC GAGGTGCGGT GCAGGAGAAC AGCGCGTACG GCTTGCCCGT    32640
CTTCTTCGAG ACGCCCGACT TGTAGACCAT CTCGCCGTGC TGGCAGTACC GCTTCTCGCC    32700
ACCAGGCGCT TCCTGAGCTG CCTGCGGGGC GCGAGACTGC TGCTGGCCAC CGCCGCCGCC    32760
GTTGGCCGGC GCGGATCCAC CGGAGCCTGC GTAGTGGCCT GCGATCTGCT GGACCTTGTC    32820
CATCAGCGCC TTGAACTCGG CGGTGTTGAC CTTGGCCAGC ACGTCGGCCG GGTCCGCACC    32880
CTTCACGACC ACCCACGGGT CGCTGTACTG ACCGGCGAAC TTGAACGTGG CCGACACCCC    32940
ATCGGTGGAG TGCTGGACCG CCATCGAGTC GCGCACAGCA GCCGAGGCCG TCGTCACCGT    33000
CGCCGACGGC GCGGTCTCAG GCTCAGGAGC CGGGGCCGGC TCGGGCTGGG CAGGGGCGGT    33060
GCTCCACGGA TCGTCGTAGG ACAACTGGTT ACCTTTCACT TAATGGGGCA TGCGCCGTTG    33120
GCGCACTCTT CATCGACACC GTCTTCGACG GCTTTGGCCG CAGCAGATTC GTACTGCTGC    33180
TTGGTGATTC GCTCGTACGG AGCCTGCGGG AAGCTGGACT CCGGGAAGAT CGTGGAGCCC    33240
TTGATGAGCC CCGCGAACCT CTTGAGATCG GCTGCGACAT CCTCGGCCTC GTAGGCGTCT    33300
GGATGGACGT TGGCGGTGAA CGACACCGCG TTGTCAGCCC AGCACATCTG GTAGAGCGCC    33360
TGGAACGCCA GGAGCTGGTG GAGGGTCAAC TCGTCGGCTG ACTAACGAT CTCCTCGTCC     33420
CAACCGAGTT CCTCGACAGC CTGGACCAAC GTGTCCTTGG TCGGGATCGA AACCACCTCG    33480
GTGTTCGGAG CGAAGAGATC CTTCTCGATC TCGTAACCCT CGGCTGCCAA CCTCCGCAGC    33540
TCGGCCATGT CGCTGTTGAG GTTGAACCGC ACACGCCGGA TGAAGTACCG CGAGAAGATC    33600
GGGTGGATCC CCTCGGAGAC TCCTGGCATC TTCGCCACCG TGCCTGTGGG AGCGATGGTT    33660
CGCTTCTTCA CCGGGACAGG GATCCTCAGA TCATGGGCGA ACCGTTCGGC CTCTGAGTCG    33720
ACCTCAGCGG CCATCTCCCG CAAGAACTGG GTGAACCGCT TATCTCCGGG TGCCTCGGAG    33780
TACCTGCTAC CTGTGAGGGC CAAATAGGAG GCAACTCCGA GATGACCCAC GCCGATGCGA    33840
CGGTTTCGGT CCAGAACCTC CCGGCTCTTC GGTCGGCCA CTTCCGAGAA CGTCGCCCGG     33900
ATCAGGAATC TCGTCATCAG ACGATGCGCC CGGATCAGGT CGAGGTAGTC GGTCTTGCCG    33960
```

```
GCCGGCGTCA CGAACGCCGC CAGGTTGATG TGGCCGAGGT TGCACGGCTC CCACGGTTCG   34020
AGAGTGATCT CGCCGCATGG GTTGGTGCAG ACCACCCGGT TGGGCTCACC GACGTTGGAC   34080
AGTGACGAGT CCCACATCCC CGGCTCTCCG TTGCGTACGG CTCCCTCGGA GAGTGCCTTG   34140
AGCACTCGGT GGGCTCGCTT CTGCTTGGGC ATGTCCTCGC GGGCGACCGC GAAGCTGCCG   34200
TAGCCCTCCT TGGCCAGACG CCAGAACTCG TCGTCAACCT CGACCGAGAT GTTCGTCGTC   34260
CAGTGCTCGC CCGTGCTCGC CTTGATGTTG ATGAACTTGT CGATCTGGTA GTCGTCCCAG   34320
TGCATCATCG ACATCCGCGC CGACCGGCGC ACACCGCCGG CCACAACACA CTGAGCGATG   34380
GCGTGGTCGA CCTCCATCGC GGCGATGCCG TCGAGCGTGA TCCCTGCGTA CTCCGAGAAG   34440
ATGTTGGCGA CCTTCTGCAG CATCACAGCG AACGGCAGCG GGCCGCTGGC CACTCCACCG   34500
AACGTCTTGA GCTTGGCCCC TTGCGGCCGG ATGCGGCTCA CGTCGTACAC CCGCTGGTAG   34560
TGGACCGTGC CGGGTCGGTA GTGCGTGTCG ATCAGATCGA CCAGCGCAGC AGCCCAGCCC   34620
TCTCGTGAGT CCTCGATGGC GTAGGCACCG GCCAGTCGT GGCTGTAGTG CTCCGACAGA   34680
ATGCCTACAT CCTTCATCGC CTGGTAGTCG ACATGCTCTG GATCACAGAC GATCTCGACC   34740
CGCAGGGGGT TTACGACCTC GGGGTAGCCT TCGAGGTAGT GGTTCGAGTA GTTCGCCCCG   34800
ACTCCCCCGC CCTCCATCAG GCGCATGAAC GTGAACTGGA AGTGGTCCGA GATCTTCTCG   34860
GGCCAGCCAG CTACCCAGCA GTTGAAGAGG TGCTGCGCGT TCTTGACCCC CGAGGCCCAC   34920
AGATGCCGAC CTGCCGGCAG CACCTTGAAC TTGGTCATCA GACGAACGAG ATCTTCTCGC   34980
TCTCCTTCCA ACATATGTCG CCGGTCGACA AGAGCAAGAT TGCCGTCCAC GACCCTCTCG   35040
ACCGTTTCCG GCCAGGTTTC CTTCGAGCCG TCAGGCTTGG TCCTGGCGTA GGTTCGGTTG   35100
TAAACGAGTT CACCGGTTGG TCCCCAAGGG ATTTCGTCAG TCAACTACTT CCTCTCAGTC   35160
AGTTCGTATC GCTTGAAATA GGCGTCGGCA GAGTCGCCGC CAGAGAACGA GACCCCGTAC   35220
TCGACCGGGC CTGCACCACG CACCTCGCAG GTAACGACGC CCTTCCTTCC CCGGAACATC   35280
GGCCAGGTTC CCTTGGAGGG GTGCTTGGTC TCGTCCCGCT GGACGATGAC CTTGGTGCCC   35340
TTCTTCATGC CGACTTCCGT TCTCCGTAGC CGGGAGTGAA GCAACCCCCG ACGTACAGCT   35400
CGAGATCTTC TTGCGACCAG TTCTCCAGTC GCATCGGCGG CTGGTGCGGG AACAGCTCCG   35460
GGAACACCTC GGCCCGGTAC AGCTCCGAAC CGGGCATCCC GTTGAACGTC GGATCAAGAA   35520
TGTTGTGCAT GGCACCTCCC TCCCAAGAAC TCGGAGATCG GCGGCTCGTA GAGGTAGCCA   35580
TCGCGCAGCT CGGGGTTCTC GATGAGCATG ATCGCGATGT TCGCTGTGGG GTCAGAGTGC   35640
CCATCCCCCT GCGACTTTCG GATGTCTGGG AAGATAGCGT GCTTGCTGCC CGGACCATCC   35700
TTGACGATGA CCTTGCCCTT GTCGTCCTTC TCCACGCCAG CCGTGATCGC GATGATGTTG   35760
ACGTGCTCGG TCAGCGACTT GTGAGCGCGG AACAACCGGT TCTGCCCGCT CTTATCCTTC   35820
GGGGAGATCC CGTCGGTGTA GCGGCTCCTG ATCGCCTCTG CATAGCCCCC GTTCTGAGCG   35880
TCCAGAGCCT TCATCGCCAG CGGGAGGATG TCGACCAGGT ACCGATTGGT CGACTCCCCC   35940
TGCAGAGCCT CTTTGACGTT CTCGGACGAG TAGTGGCTGC GCTCCTGGAA CAAGTCGCGG   36000
GCCTTGGCCG CTCCGACAG GATGTTGCGA ACCTGATTGC GTACGTAGTG AACTGCCTCA   36060
CCACGGTGCA AGCTCTCCAG CGTCTTCTGG ATGTACGGGC TCTCGAGGTA CCAGACCCAC   36120
AGCTCTTGGA TGATCTCCTC GGCTGTCAGG TTGGTCTCCC AACCGATCAG CGCCTTCCGG   36180
GTGGCCCTGC TGAACAGCTT GCTGATGTCG TCGGTCAAGG CATCACCTTT CGTAGGTACT   36240
CCTCCCGGTC CAATCGGCGG TCGAGGTGTC GAGTGACCTC CTCCGCGAAG ACCTCGCGGA   36300
CTTCGCTGGA GGTGATCTGG CGCGAACGTG CGTTCTTGTG CAGGTACGGC AGCTTGGTGG   36360
```

```
CTGTCAAGTT CTAGACCTCC CAGACTCGGC CGTCGACCGA GAACCGGCCT CCGACAATCG    36420
GAACAAGCTC AGGCTTGACG TGCTGGCCGT CGACCGTCAG CAGAGCAAAA CCACTCTGCC    36480
AGTTGGCTGT TGCACCCTTG AGGTACTGAG CTAGCTTCAT GTTCATCAGG TTGCCGACCT    36540
CCATCGACCA CAGCACCTTC TGGTTGCCGC CGTAGCCCAG CGTGTGTGGC TTGATGCCCT    36600
GGCGGTGGGT GTGTCCGATG ATCACCGACG TGCCGAACCG CATCATCGCG TTGTACGCGG    36660
TGTCAGCGGA CTTCTGCGTC ACCCGGACCC CACCACGGTG GCCGTGGGTG GAGATCCAGC    36720
CTGGAGCGAT CTTGTAGAAC TCAGGCAGCA CGTCAACACC GAACCCGTCG AAGTCCAGCA    36780
GGTTCTGGAA CTGGAACGAG CTGACGTACT CGACCAGCGC CGGGGCGAAC TGGTGCAGGT    36840
AGTCGACTGG CCGGCGGTCG TGGTTGCCCT CGTGGACACC AACCGGGCCG TCGTAGACCT    36900
GGCGCAGCGG CTCCAGGAAC CGCCGCTTGC ACTGCTCGGA GTCGGGCTTG ATCCGCTGAG    36960
CGAACTCTTC CTTGGTGCCC TTGGTCCACC GAGACGGGCT CGGGTAGTCC ATCAGGTCAC    37020
CGATGTGGAC GACCTCGTCA GGCTGGGTGT CCCGATGTA GCCGATGACC GCCTTCAACT    37080
GCTTGCGATC ATCGAACGGA ATCTGGGTGT CCGAGATGAC GACGATGCGC TTGCTCACTC    37140
AGCGACCTCG GTGAAGGGGC CCGCATACG TTCCTCGTGG GAGCTGGCGT TGCCTCCTGA    37200
CCAGCGTCGC TTGCCCACCT TGGTGTGGTG CAACCCGTTG GGGTAGTAGA TCCACTTCAC    37260
TCCTGTGGCG TTGGTGACGG TCTTCACATC GGCAGGAACG TCCAGCAAGG TGTCCCACTG    37320
GCGAGGCCCC TTGGGATACC GCTCGTCCTC GGGGAGCTGC ATCTTCTCCA GAACGCCTGC    37380
GTAACCGGCG ATGTCGACCA CCGTGTCCTG GTGGTAGCCG TTCTCCATGA ACCGGGCGAT    37440
CTTCAGCAGG ATCATCATGA CGGCCACGTC CTCCGGGGTG AACTCGACGC CGCGCTTGTA    37500
CGCGCCCCAC AGGGTCGCGA TGCGTTCGTG GTTCTCCTTG GCGTCCCCGT AGTCCTGGGC    37560
TCGCTGTCCG TTGATGATCT CTTCGGCGGT GGTCAGAATG CTCACAGTCC AGTCTCCGAT    37620
GCGGTGTAGT AGTCGATCAG CTCATCGAGC TGGTCCGGTT GATAGCCGAG GATCGGCTTG    37680
TGGGTGTCAG TGACGACGAC GGGAACCGAC ATCGCGTTGA GCACCTTGGT GACGTAGTCG    37740
TACGCCTCCG AGTTGGCCGT GACATCGACT GCGTCGAAGT CGATCCCGGC AGCCGTCAGC    37800
TTGTCTTTGA CTCGCTCGCA TGGCTTGCAG CCGGGACGGG TGTACACCGT GACCGGCGCG    37860
AACAGCGTTC TCACGTGAGC ACCATCCAG TCGATGTATC GGTCTCCATA CATCAGATCC    37920
TTTCCAGCAG AGCAGCTTTG CCCTGCGATG TGACTAGTGA GTTGACATCC TCGCCTTCTG    37980
GCATCGGGAT GATTCGGGCG TTCGGCAGCG TCTTCGCCAC CGACCGGGCG AACTCCATAC    38040
CGGCGTCGTC GCCGTCGGCC AGGATGTTCA CGTTGCGGTA GCCCAGGAAC AGCTCTCGGA    38100
AGTACGGCTT CCACTTCTGG GCTCCGCTGA GCCCCACCGT CGGCAGCCCA CACAGCTCGG    38160
CGGTGATCGT GTCGAGTTCT CCCTCGCAGA TCGCCATGTC CTTGCTGTAT TTGGTCAGCG    38220
CGTAGGTGTT GTAGAGCCGG TCCTTCTCCC CTGGCATCGA CAGGTACTTC GGTGTGCCAC    38280
CGTCGATTCG GCGATACCGG ATCGCAGCTA CCGTCCAGTG ACGCCAGGGC GACCACCGCA    38340
TATACGGAAT CGCCAGGCAG CCCCGGTACA TCTCATGTCC AGGGAGTGGG TCGTCCACGA    38400
ATCCCAGACC GAACCGGCTT AGTTCCGCTC GGCCGGCCAG CCCGCGACTC GCCAAATACT    38460
CGTCGGCTGG GCTTCCGGGC AGGCTTTCTC TGTACCGGGA CGTTGCCTCC CACAGATAGG    38520
TTCTCTGCGA TTCGCTTAGC CTCTGCAAAT GTCACCTCCT CTTCGTGACG AATGATCGAG    38580
ATCACGTCTC CACGGACCCC GCAGGCCATG CAGTTGTAGC CCTGTAGGTC GTAACTGACT    38640
GCGGCAGACG GCGTTTCGTC GCCGTGGAAG GGGCACAGGC ACTTGTTCCA CTCGTGGTGG    38700
TCAGGTGGTG GTTCCCAATC CGGGTGGTAG CGAAGAATCG CCCTCGCGAT GGGCGAGTCG    38760
```

```
TTCATTCGTC CTCGTCAAGC TCCTCGGGAG AGAGCCCTTC GAAGATCCCG TTCAGGACGG      38820
CGGCGAAGCC CTCGCCGGTC TCCGCTGCGT CGAGCATCTC TGCAATCGTC TTTGCCATGT      38880
TTCCTCCTGG TGGATGTCAA GTTCGAGACA GCTTGTCAGC CTCGACTGGA GCGATGCGCT      38940
CCCCGATGAC TTGGACGGCC GGCGGGTTCA GCAGGTACTC GATGGCCCGT TTGAAGAACT      39000
CGATGCAGTC CCTCGCCCAG CCCAGCGTGT ACTTGTTGCA CATCGTGCAG AGCAACCCTC      39060
GGACGATGCC TGTCTTGTGA TCGTGGTCGA CCGACAGGCG CTTCTTCTTA CCGTTGGCTC      39120
GCTGGCAGAT GTAGCACCGA CCACCTTGGA ACTCGTAGAT CTGCCAATAC TCATCGCCGG      39180
TGATGCCGTA GGTGGCCAGG ATCCGGGTCT CCCAGCTCGT AGAGCTGCGA GCCGTCCTGA      39240
ACTCTCGGTG ATGAGTAGCG CATCGTGGCC CTGGATACTT GGCGTCTCGC GTGAGCGGGA      39300
GCCCCTGTGC GACACAGTCT TTGCAAGGCT TCCGCTTGTG CTTACGGTTC TGCACCCGGT      39360
ACCCCGGAGA CCTCTTCGCC GCCCTCGGCA CGCGCGTCCT CCTCCCGGTT CTCCATCACC      39420
ATGCAGAACC ACGACAGCAG CCCTGCCAGG GAGATGTAGA AGGCCACCAG AACTTGGCCG      39480
CTCACTTCAC CATTCCTCGA ACCCACCAGC GAGACAGCGC CTTACGCCCT TTGTCGAGCG      39540
GGGTCAGCTC GCGCTCATCG TCCTCACCGA AGTCGAACTC GATGCTGGCG ATCTCGTAGC      39600
CGAGGATCTT GAACGACACG TTCATAGGCG GTCTCCGAAG TTGATGACGG GAATGCCGGC      39660
CCTTTCGGCC TCTCGCATGC AGTGCCGGGT GCCGACTGAG TTGCCGAGGG GGAACGCCAG      39720
ACAGATGTCC GCACCGGCCC TGACCATCTC GATGTTGCGG AGGATGCCAG CCCGCTTGCC      39780
GTAGCGTTCC CAGTCGGCTC GGTGCAGCTC GGGGAGCACG TCCCATCCCT CCTGCTTCAT      39840
CCCCCAGGCC CAGCGGTCTG CGATGTCGTC AGCGCCGCGA GCGCCGCCGT GGACGACCGT      39900
GAGACCGGAG AAGGACCGGT GGTACTCAGT GGCCAACGCT TCCCAGACCG TGGTGCGGTC      39960
CTTCCAGATC CGAGATCCGG TGATCAGTAC TCGCCGCATC AGATCGCCTC CCACTGCAGG      40020
CCGTCGTGCG ACGTGACCAG CTCCGCTTCG TAGACGCCGT AGCGGGTGGC CAGGAACTGG      40080
ATCATCTGCG CCTGCTTGTA CCCGAAGGGA CATTCGTGGA CGCCGCTGAT CGGGTATCTG      40140
ACTCCGTATT TCACTTGATC CACCGCTTCG CGATTCGGTC GACGTTCTCC TCGGAGACGT      40200
TGCGGGCGAG GCCGGTGAAC TCCTGGCCGT GGACCTTGGT CTCGATCACG CGAGGCTTGC      40260
GGGGATCCGG GCTCTCCGGG TCGATCCGCT TGTGGGTCCA GACGGTCGGC TTCGTCTTGA      40320
TCAGAGCGCC CAGCACCTGC TGGCGCAGTG GGTTGGTCTT GCGGGGCATA GCGTTTGGAG      40380
TGGTCATCTG GATCCTTTCC TCGGTGGCTG TCAAGTCGGT GTGCGTAGTG AAGCCCCCC      40440
AGGCATGCGC GCCCCGCCTG GGGAGAGTTG ATCAGCGCAG TTCGATGTCG GCAGGATCG      40500
CCTGCGGCTT GAAGTTGACC TGGTAGAAGT CGGTCGAGAC GTTTGCGCCA TCGACCTGCT      40560
CCATGAAGTA GGAGACGTTG TCCGACAGGC CCAGGAAGTG CTTCTTGATC CCGTCCTTGG      40620
TCTTGCAGGT CACGTCGAGC TTCTTCGACG CGGTGTCCGC GTTGATTGAG CACCGGCCCT      40680
GGATCTCGAG CAGGTACTTG TCCGTGATCC CGTTGAAGAA CACGATCCGG CGATTGATCT      40740
CGAAGTTGTC AGCGGCCTTG CTGACGTTCT CCGATGCGAC GTCGGCGTCG GAGGTACACG      40800
CGGAGAGGCC CAGGATCGCC GATCCGGCGA TGAGTGCGGT GGCGATGATC TTCTTCATGT      40860
TCGCTACTTT CTGTTTGGTG GATGTCAAGT TAGTGACCGA AGTCGTTGAT CTGCATAGTG      40920
TCTCCGACGA ACTCCAAGGA AGCGAAGTCT TGTCCCGACG GGTCGACTT CCCCCCTCGG      40980
TTCTTGACCG TGGAGACGTT GAGCATGTCC GGGCCGAACC CGTCCGATAC TCGGTGGAGA      41040
GTGAGGATCA TCTCAGGAAC ACGCCCGATC TGACCTTTGA TGCCCGACAA CGGGATCGGC      41100
TTGTCGCCGT CGTTGTGCGG GCCGGTGACG TGGTGGAGCC CGACGACGCA TGAGCCTGTC      41160
```

-continued

```
TCACGGCCCA TCTCGTGTAG GTAGTCCATC AGCGACTCCA GACCCGAGAA CGGGTCGTCT    41220
CCCTCGCTTG AATCGGTGCG GACGTTGGTG ATGTTGTCCA CGACGATCAA CGCTGGGAAG    41280
TCCTCGTACA GCGCGTCATA CGCGGCCAGA GCGTTCTCGA TCTCGTCCAA CGACGGTGAT    41340
GCCTTGTAGT TGAACCGGAT CGGGATCTCG TCTAGTGAGT CAGCTACCGC GTCCTCGATG    41400
TTCTGCTCGC GAACAGCCCG CGTAGCTCGT TCGAGCGACC ATCCGCTGAG GATGGACACC    41460
GAACGGGAGA GCTGGGTGAA CGCATCAGAG TCGGCCGAGA AGTACAACGT CGGCACCTTC    41520
GACTTGAGCG CGTAGGCGAG GACGAACGCC GACTTCCCGG TGCCGGGGCC GGCGCAGACC    41580
AGGACTAGCT GGCCTCGTCG GAGATGTGTA CCTTTCTGGT CAAGCGCGGC CCAGACCGGG    41640
GGTAGCGGAT CCCCCGCCGA CCCTCGGATG TAGAGCGATT GTCTAGGTGT GTACACCTTC    41700
CTCCTCGTGG ATGTGATTGA CCAGGTCATA GATCTCGTCG CGAGAGACCA GCCGGCCCCA    41760
GGCGTCGATC CCCACGTGGA TCTGTCTCCG GTGGATGTGT CGGGACAGGA TCATCGGCGA    41820
ATGCGTGTGC CCGTGGATCA GGATCTTGCC ATCGTCACGG AGCCTCCACT GGGTGTGTCG    41880
GTCCTCGCTG GTGTGGTCCC CGACGTATGG GAAGTGGCTC AGCAGAACAT CTGTGTGCCC    41940
GCCAGCGTCC CCGTACAGCG GCACCCGGAT ACGAGCTGCC GTCGACACAT GCTCGAACAC    42000
CATCCAGTAC GCACCAACCA GCTTGTGAGC ATCGCGGTTC ATCGGGTGGG GCCCATCGTG    42060
GTTGCCCAGG ATCAGCCGTT TGCGGCCTGG CCGATCCGAG ATCCACCCGA GGGCATGTAT    42120
CTGCCCCTTG GTGGAGCCAG AGGAGATGTC ACCTAGGATC CAGACCGTGT CGTCCTTGCC    42180
GACGACCGAG TCCCACGCCT TCGCCAGGGT GGCGTCGTGC TCTTCGACAT CATCCGCCAG    42240
GTTGCGGATC TCCATCAGCC GCTTGTGTCC GATGTGTAGA TCGGACGTGA ACCAGGTGTT    42300
GCTCATGGCT TCCTTTCAGA ACGGCGGGCC GTACAGCTCG ATCACCAGCG CGTGCAGCTC    42360
CTCTGCCGCG TCGTCACGCT CGAATCCGCA GCAGGAATCG TGCCGGTCGA GGATTGCGAC    42420
GATCTGGTCG TAGAGGCTGG GCCTCACTTC ACCTTCTTCG GATCGATCAA GGCGTCGTGA    42480
ATCGGCCGAC CGGCGCGAGC CGCGTGCGTC TCGGCGTCCA AGGCTCGCTG CATCTGGTTC    42540
ATCAGCCGGG TGCCGCGCAG CTTGAGGATC TTCATGGTCG CCCGACCCTT GTATCCAGCG    42600
CGGTGCATCC GTAGGACGCA GGCTGTCTCG TGCGGGGCTA TAGGTGACCT CAGCGACGGG    42660
TGGTTTGGAT CCCAGTTCGT CATGTCTTCC TCTCGGTGGC TGTCAAGTTG GTCACAGACC    42720
GAACTCTTCC TGGTACTGCG GGATGAAGTG GCCGGCCGTT CATGTTCGGC TCGATACCTC    42780
TCGCGTCACG AACTCCTGCC CGTTCCATCT CCGACCGTCC TCGAACTCGA TCACGATCTC    42840
TCGTCCGGGA TGACGCACGG CCTCCGCTTG GGCAAACCTG CGTGCAGCCT CTGGGGTCGG    42900
GAACGGAAAC TTCTGCGAGG CGTACAGCTC CTGGTGCCAC TTCGGCTTGT CAGGAATCGG    42960
CCCCATTTCC ACGTACGTGT AACCCGCGTC GGGGTCGAGT TCGAGCGTTT TCTTGTATTC    43020
CTTCGTGCCT GCCTTAGAGG GAAGGTGAGT ATCGGTGGCT GTCAAGGTGA CCTCACTTAA    43080
AAACAGGGCA GCTGTAATTC ACATCACAGA AGCCGCATTT GTCAGGTTCA GGCAGAGGCT    43140
CGAAGTCACC AGCCTGGATC CGAGCCTCGA CCTCATGGAA CCTCTCGGTG ATCCGCTCCC    43200
GCGTCCAATC GGTCAGGTCG TAGGGCGCAG TGGGCTTCGC CTTGATGCCC TTCTTCCCCG    43260
CCATGAAGTA GTCGCCCGTC TTCGGAGCCT CCACGTCATA GGTCATCGCG ACCGCGAGCG    43320
CGTACACGCC GAGCTGGAAG TCGTCACCCG GCGAGTTGCC GGTCTTGTAG TCCCGGACTC    43380
GAAGCTCACC GTTGACCACG ACGACCGCGT CGATGAACCC TCGGACGCGG ATGCCGTCCA    43440
GCTCGATGTT GAACGGAAGC TCGATGGCCG GCTTGGGCTG TTCACACTCC TTGCAGTTGG    43500
TGTCTTTCCA CGCCTCCGTA GAGCAGATCC CTCGCCCAGG GGTAGTCCAG ATCTGCTGGC    43560
```

```
CCTTGTCCTT CCGCCACGCG ATGAACTTCT CTACCTGCTC CAGTCCAAGG TGGAACCGGC    43620
GCTCGATGTC ACGCTCACCG TTGTACGGCC CGGACCAAAA CCACCACTCG AAGTTCGGGG    43680
TTTCGTCGCA CAGTGCTCCG ATGTCCTTGG CGTACTCCTC GCGGAAGATC TCTTGTGCCC    43740
GTTCGAGGCT CATCTCGCGG CCCTCGGCCA GAGCCTTCTC GTAGACCTCA GCGACGGTGT    43800
GAAACGCGGT GCCCTGCGGC AACCACGCCG CAGGACGAGC CCATACCTTG TCGATGCGAG    43860
CCAGCTTGTA CGCCTGCGGG CAACGTGTGT ATTGGTTCAA CTGGCTGACG CTTCGCAGCG    43920
GCAGCAATGT CTTGGTGTCT GTCACGCAGC GGCCATCCTT CCCTTGCCTA TCGTCTCGTT    43980
CAGCGCCCCG TCGACAGCGA CACTGAGCAG TTTTGCGACC TCCGACATGT CAATCGGATC    44040
CTTGGGGAAT TGGTCAGCCT GAGTCATCCT GAGCACCATC CACTCGGTGC CCTTGTCGCA    44100
GTGGATCATG GTCGGATCCT TAATTAAGAT CCTTTAGTGA GGGTTAATTG CGGCCGCGAA    44160
TTCTTGAAGA CGAAAGGGCC TCGTGATACG CCTATTTTTA TAGGTTAATG TCATGATAAT    44220
AATGGTTTCT TAGACGTCAG GTGGCACTTT TCGGGGAAAT GTGCGCGGAA CCCCTATTTG    44280
TTTATTTTTC TAAATACATT CAAATATGTA TCCGCTCATG AGACAATAAC CCTGATAAAT    44340
GCTTCAATAA TATTGAAAAA GGAAGAGTAT GAGTATTCAA CATTTCCGTG TCGCCCTTAT    44400
TCCCTTTTTT GCGGCATTTT GCCTTCCTGT TTTTGCTCAC CCAGAAACGC TGGTGAAAGT    44460
AAAAGATGCT GAAGATCAGT TGGGTGCACG AGTGGGTTAC ATCGAACTGG ATCTCAACAG    44520
CGGTAAGATC CTTGAGAGTT TTCGCCCCGA AGAACGTTTT CCAATGATGA GCACTTTTAA    44580
AGTTCTGCTA TGTGGCGCGG TATTATCCCG TGTTGACGCC GGGCAAGAGC AACTCGGTCG    44640
CCGCATACAC TATTCTCAGA ATGACTTGGT TGAGTACTCA CCAGTCACAG AAAAGCATCT    44700
TACGGATGGC ATGACAGTAA GAGAATTATG CAGTGCTGCC ATAACCATGA GTGATAACAC    44760
TGCGGCCAAC TTACTTCTGA CAACGATCGG AGGACCGAAG GAGCTAACCG CTTTTTTGCA    44820
CAACATGGGG GATCATGTAA CTCGCCTTGA TCGTTGGGAA CCGGAGCTGA ATGAAGCCAT    44880
ACCAAACGAC GAGCGTGACA CCACGATGCC TGCAGCAATG GCAACAACGT TGCGCAAACT    44940
ATTAACTGGC GAACTACTTA CTCTAGCTTC CCGGCAACAA TTAATAGACT GGATGGAGGC    45000
GGATAAAGTT GCAGGACCAC TTCTGCGCTC GGCCCTTCCG GCTGGCTGGT TTATTGCTGA    45060
TAAATCTGGA GCCGGTGAGC GTGGGTCTCG CGGTATCATT GCAGCACTGG GGCCAGATGG    45120
TAAGCCCTCC CGTATCGTAG TTATCTACAC GACGGGGAGT CAGGCAACTA TGGATGAACG    45180
AAATAGACAG ATCGCTGAGA TAGGTGCCTC ACTGATTAAG CATTGGTAAC TGTCAGACCA    45240
AGTTTACTCA TATATACTTT AGATTGATTT AAAACTTCAT TTTTAATTTA AAAGGATCTA    45300
GGTGAAGATC CTTTTTGATA ATCTCATGAC CAAAATCCCT TAACGTGAGT TTTCGTTCCA    45360
CTGAGCGTCA GACCCCTTAA TAAGATGATC TTCTTGAGAT CGTTTTGGTC TGCGCGTAAT    45420
CTCTTGCTCT GAAAACGAAA AAACCGCCTT GCAGGGCGGT TTTTCGAAGG TTCTCTGAGC    45480
TACCAACTCT TTGAACCGAG GTAACTGGCT TGGAGGAGCG CAGTCACCAA AACTTGTCCT    45540
TTCAGTTTAG CCTTAACCGG CGCATGACTT CAAGACTAAC TCCTCTAAAT CAATTACCAG    45600
TGGCTGCTGC CAGTGGTGCT TTTGCATGTC TTTCCGGGTT GGACTCAAGA CGATAGTTAC    45660
CGGATAAGGC GCAGCGGTCG GACTGAACGG GGGGTTCGTG CATACAGTCC AGCTTGGAGC    45720
GAACTGCCTA CCCGGAACTG AGTGTCAGGC GTGGAATGAG ACAAACGCGG CCATAACAGC    45780
GGAATGACAC CGGTAAACCG AAAGGCAGGA ACAGGAGAGC GCACGAGGGA GCCGCCAGGG    45840
GGAAACGCCT GGTATCTTTA TAGTCCTGTC GGGTTTCGCC ACCACTGATT TGAGCGTCAG    45900
ATTTCGTGAT GCTTGTCAGG GGGGCGGAGC CTATGGAAAA ACGGCTTTGC CGCGGCCCTC    45960
```

-continued

```
TCACTTCCCT GTTAAGTATC TTCCTGGCAT CTTCCAGGAA ATCTCCGCCC CGTTCGTAAG      46020
CCATTTCCGC TCGCCGCAGT CGAACGACCG AGCGTAGCGA GTCAGTGAGC GAGGAAGCGG      46080
AATATATCCT GTATCACATA TTCTGCTGAC GCACCGGTGC AGCCTTTTTT CTCCTGCCAC      46140
ATGAAGCACT TCACTGACAC CCTCATCAGT GCCAACATAG TAAGCCAGTA TACACTCCGC      46200
TAGCGCTGAG GTCTGCCTCG TGAAGAAGGT GTTGCTGACT CATACCAGGC CTGAATCGCC      46260
CCATCATCCA GCCAGAAAGT GAGGGAGCCA CGGTTGATGA GAGCTTTGTT GTAGGTGGAC      46320
CAGTTGGTGA TTTTGAACTT TTGCTTTGCC ACGGAACGGT CTGCGTTGTC GGGAAGATGC      46380
GTGATCTGAT CCTTCAACTC AGCAAAAGTT CGATTTATTC AACAAAGCCA CCGAACGCCA      46440
GCAAGACGTA GCCCAGCGCG TCGGCCGCCA TGCCGGCGAT AATGGCCTGC TTCTCGCCGA      46500
AACGTTTGGT GGCGGGACCA GTGACGAAGG CTTGAGCGAG GGCGTGGAAG ATTCCGAATA      46560
CCGCAAGCGA CAGGCCGATC ATCGTCGCGC TCCAGCGAAA GGGGTCCTCG CCGAAAATGA      46620
CCCAGAGCGC TGCCGGCACC TGTCCTACGA GTTGCATGAT AAGAAGACA GTCATAAGTG       46680
CGGCGACGAT AGTCATGCCC CGCGCCCACC GGAAGGAGCT GACTGGGTTG AAGGCTCTCA      46740
AGGGCATCGG TCGAGGAACT TTCGGCGGCT TTGCTGTGCG ACAGGCTCAC GTCTAAAAGG      46800
AAATAAATCA TGGGTCATAA AAATTATCAC GTTGTCGGCG CGGCGACGGA TGTTCTGTAT      46860
GCGCTGTTTT CCGTTGGCCG TTGCTGTCTG GTGATCTGCC TTCTAAATCT GCACAGCCGA      46920
ATTGCGCGAG CTTGGTTTTG CTGAAACCGA CACACAGCAA CTGAATACCA GAAAGAAAAT      46980
CACTTTGCCT TTCTGACATC AGAAGGGCAG AAATTTGCCG TTGAACACCT GGTCAATACG      47040
CGTTTTGGTG AGCAGCAATA TTGCGCTTCG ATGAGCCTTG GCGTTGAGAT TGATACCTCT      47100
GCTGCACAAA AGGCAATCGA CCGAGCTGGA CCAGCGCATT CGTGACACCG TCTCCTTCGA      47160
ACTTATTCGC AATGGAGTGT CATTCATCAA GGACNGCCTG ATCGCAAATG GTGCTATCCA      47220
CGCAGCGGCA ATCGAAAACC CTCAGCCGGT GACCAATATC TACAACATCA GCCTTGGTAT      47280
CCTGCGTGAT GAGCCAGCGC AGAACAAGGT AACCGTCAGT GCCGATAAGT TCAAAGTTAA      47340
ACCTGGTGTT GATACCAACA TTGAAACGTT GATCGAAAAC GCGCTGAAAA ACGCTGCTGA      47400
ATGTGCGGCG CTGGATGTCA CAAAGCAAAT GGCAGCAGAC AAGAAAGCGA TGGATGAACT      47460
GGCTTCCTAT GTCCGCACGG CCATCATGAT GGAATGTTTC CCCGGTGGTG TTATCTGGCA      47520
GCAGTGCCGT CGATAGTATG CAATTGATAA TTATTATCAT TTGCGGGTCC TTTCCGGCGA      47580
TCCGCCTTGT TACGGGCGG CGACCTCGCG GGTTTTCGCT ATTTATGAAA ATTTCCGGT       47640
TTAAGGCGTT TCCGTTCTTC TTCGTCATAA CTTAATGTTT TTATTTAAAA TACCCTCTGA      47700
AAAGAAAGGA AACGACAGGT GCTGAAAGCG AGCTTTTTGG CCTCTGTCGT TTCCTTTCTC      47760
TGTTTTTGTC CGTGGAATGA ACAATGGAAG TCAACAAAAA GCAGAGCTTA TCGATGATAA      47820
GCGGTCAAAC ATGAGAATTC GCGGCCGCAT AATACGACTC ACTATAGGGA TCTTAATTAA      47880
GGCGCCTGAT CAGGATCAGG TCGATGGCTT TGTTGTTCTC CGGGCAGCGC ACCGCCGTCG      47940
GAAACTCGGC CTTGCCTTTG GCGAACGTGG TGTCGACGTA GGCGATGTTG ATGCCCTTGT      48000
CTTCCAAGAA GCGCGCCACG TCGATGTTGT CCGGGTCTGC GCTGAAGTAC AGCGCCAGGT      48060
TGTCGAGCCT CTGCGAGTGC AGGTAGACAG CCGCCGTCTG AACCCTTGTG TAGGCCCAGA      48120
ACTGGACATC CGGGTTGTCG CGGATGACTC GACCCCAAGC GGCCACATAG GTGGGGCTGA      48180
AGAAGTCTCC ATCCCAGTGG ATGCGGAACA GCTTCGGAGC CTTGCGACGG TCGCAATCCT      48240
TGACGAACTC GGCGACCATC TCGGACAGCA GCGTCACGGT GTCTGTCAAG TCAGCGTCAC      48300
GCAACAGTTC CCAGTTGTGC AGCAGGACCG AGCTGACAGC CTTGCGAACT TTCTCCAGCT      48360
```

```
TGCCGGCGTA  GCACACCTTG  GCACAGAAGG  CCGTCGCGTC  CGGGCAGGAG  AAGCCTTGAC    48420

CGGAGGGCAG  GCCGATGCTG  TTGGCGATAC  CTACGGTGGC  GTTGCCGCCC  TTGGTGACGT    48480

GGACGTAGTT  GGTGACCTTG  CGGTCGTTCG  AACGCTTCAG  CTTGGCCATA  CCTAGCCTTC    48540

CTTCGGTGGC  TGTCAAGTTG  TTGGATACAA  AGCGCCCCGA  GAGGGAGTCG  AACCCTCACA    48600

CCGCGAACCG  TCGCGGGGCC  ACCGTGCCTA  GTCGATAGAG  GTCACTCGAC  TCTCGTGGAC    48660

GTAGACCACG  GTGTTGCCTA  CGTTCACCGC  GTAGTACAGG  CCATCGGCAC  CTCGTAGCTT    48720

GTGCCGAACC  GTGCCCGACG  TGGCCGTCAT  GTCTTCGCCC  CAGTCGGCGT  TAGGTGCCCA    48780

GGTGACTCGC  ATGGTGATCC  CTTCAGTAGT  CGGTGGCTGT  CAAGTCAGCG  GATACGGACG    48840

TACCCGTTGC  CTCGAGCGAC  GTAGATCTTG  CCGTCGATGT  AAACGCGCTG  CTGCTGGTTC    48900

ATAATCCTAT  TCCTTTCGGT  GGCTGTCAAG  TCTCAGGCCC  AGCGACGAGT  CGTCGGCCGG    48960

GGGCGGCGCA  CCTTGGGCGC  GTTGGCTCGC  GGTGCCTTAC  GGATGGCGGT  GCCTACCGTG    49020

ATCTCTTCCA  ACTGGCGTTC  AGCCAGGCCG  ACAGGCCGGG  CGTCACCGGG  CAGTTCGATC    49080

TTGTAATCGA  AGTCAGTCCA  CCCCTTCAGA  CCCTTCTCCA  GCTCGCGATC  CAACAGACGC    49140

GGAGCCGACA  GCTCAGGCGC  AACAAACGGT  GTCTTGACGC  TCTCGCGGGC  AGTAACCCGA    49200

ACCTCACGGT  GCTCAGCGAA  GACTGGCATA  GTTCACCCCT  TTGGTGGATG  TCAAGCCTGA    49260

GCACCAAAGC  TCAGGCGTAG  TGGGTAGTCG  GGAATCGAAC  CCGATAGCTT  CATAGCCACG    49320

TTCTACGGCT  CAGCCATAGC  TCAGCGATCA  TTCCATCGCG  CCAAGAGCTA  CCCTCCCGAA    49380

TGCCGAACCA  AAGCTCAGCA  TTCGTAAGTG  TGTATTCTCC  CCGTGGCTCA  GACAGTATCT    49440

ATCAGAACCT  AACCACAGGT  CTACATTTAG  TTATCCGCAG  TGCTCGCACT  TTAACGGCAT    49500

CGAGCTTCCG  CCGACCCTCA  GTCCTCTGGC  AGCGAACTAA  AGGTTTGAGT  CGGGCTGCGG    49560

CCCTTCTCGG  TCTTGCGTGA  TTCTCACTCT  ACCGGATGTT  TCGGTGGCTG  TCAAGCGGGC    49620

CGTTTTGGTG  TTGCAACGAT  GCCCTCGTTT  AGCGCCGCTG  GCGTAATGCG  CTACCCGCCT    49680

GATCTCACCG  GTCCAAGTTG  GTGATGCTTG  CAGCTTACCC  GATAACCGGG  TGGCTGTCAA    49740

ACCGGAGAAT  CTTGCCGCCG  GATTTTCACC  GGCACCGGCA  CGATCCTCTC  GGATCCGCCT    49800

ACCGCCTTGC  TGCTGCGGTG  ACACAAGAAT  GCACTACTGG  CCGGGTGGCT  GTCAAGCCCT    49860

AATCGCAAAT  TGGTGCCCTA  GCTGCAGATA  TGGCGCGTTC  TCGGTGGCTG  TAAAGGGCAC    49920

TACGTGCCGC  TATCCGCTGG  TCACGCTGGA  CAGTCCGGC   AGCCCGTGCC  GCGCATAGGC    49980

TGCTCACTAC  GTGCCCGGTA  TCGGCGTTGT  CGTGCCGCTG  TCGTGGTCGT  CGCCCCGTCG    50040

CTGTCGCTGG  TCTCGGTGGC  ATCGCTTGAC  AGTCGCCCCG  CTATCCCCCG  TTGCCGCTGG    50100

TCAGACGCTA  ATCCGCTTAT  TTCGCATAGG  CTGCTCACTA  TCGCATCGGT  ATGCGTATGC    50160

GCTGGTCACA  TATGCGTGTG  GTGGTGGTGT  GGTGTGCGTG  TGTTTGCGCT  GGTCAGCCGT    50220

GTGCGTACCG  TATCCGCACA  CTGTGCTTGT  GCGTTTGCTG  TGTGTCGAGG  CCGGCTCTCG    50280

CATCGTCGCA  TGTCAGCGCG  GGTATGGGCG  TGTATCGCAC  GCTTTGCTAG  CCGCGTGCCG    50340

C                                                                        50341
```

Figure 3:
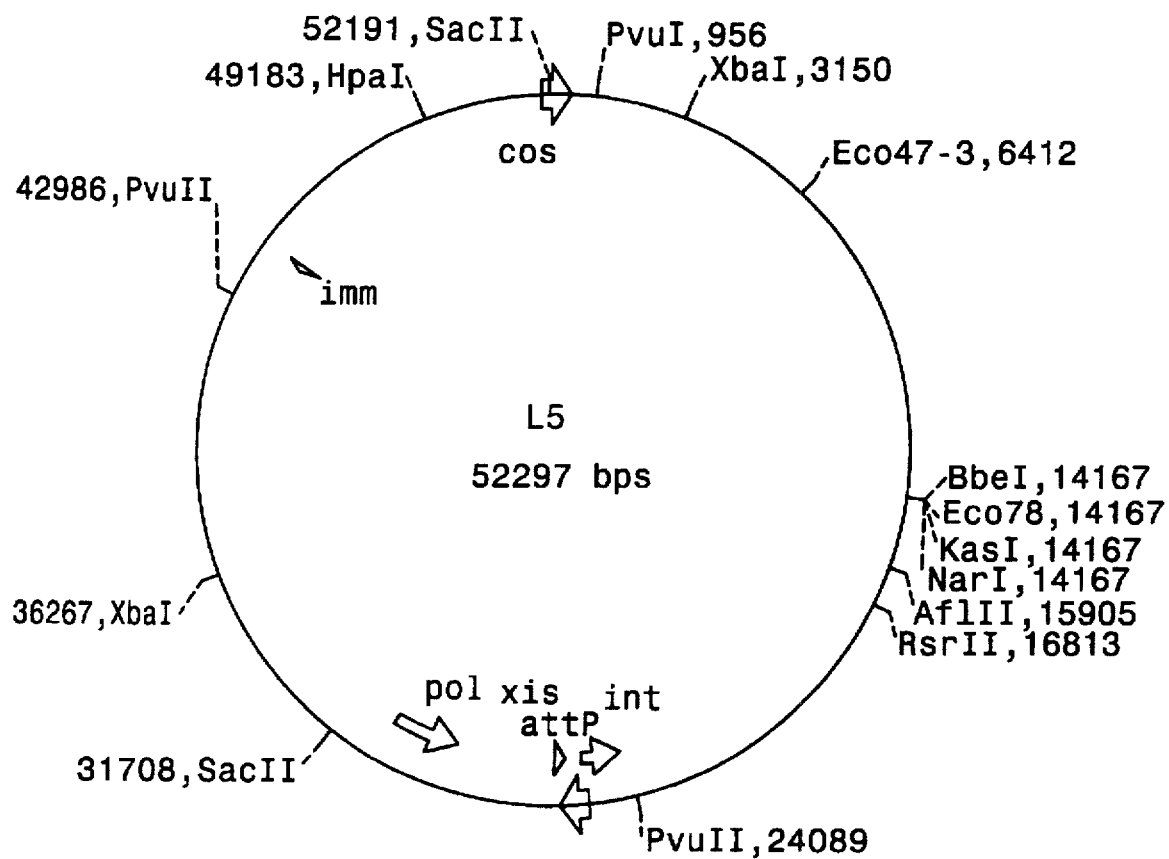

We claim:

1. An L5 shuttle phasmid comprising mycobacteriophage L5 and an E. coli-bacteriophage lambda cosmid inserted in a non-essential region between the PvuII restriction site at nucleotide 42,986 and the SacII restriction site at nucleotide 52,191 of the mycobacteriophage L5 genome as shown in FIG. 3.

2. The L5 shuttle phasmid of claim 1 further comprising foreign DNA inserted into the E. coli-bacteriophage lambda cosmid.

3. The L5 shuttle phasmid of claim 2 wherein the foreign DNA is a transposon, a reporter gene, or a gene encoding an enzyme.

4. The L5 shuttle phasmid of claim 3 wherein the transposon is IS1096.

5. The L5 shuttle phasmid of claim 3 wherein the reporter gene is a luciferase gene.

6. The L5 shuttle phasmid of claim 3 wherein the gene encoding an enzyme encodes a DNA-modifying enzyme, an RNA modifying enzyme or a protein modifying enzyme.

7. L5 shuttle phasmid phAE41 deposited on May 20, 1994 with the American Type Culture Collection, Rockville, Md., and designated ATCC No. 69624.

8. L5 shuttle phasmid phAE42 deposited on May 20, 1994 with the American Type Culture Collection, Rockville, Md., and designated ATCC No. 69625.

9. L5 shuttle phasmid phAE43 deposited on May 20, 1994 with the American Type Culture Collection, Rockville, Md., and designated ATCC No. 69626.

10. L5 shuttle phasmid phAE44 deposited on May 20, 1994 with the American Type Culture Collection, Rockville, Md., and designated ATCC No. 69627.

11. L5 shuttle phasmid phAE45 deposited on May 20, 1994 with the American Type Culture Collection, Rockville, Md., and designated ATCC No. 69628.

12. L5 shuttle phasmid phAE46 deposited on May 20, 1994 with the American Type Culture Collection, Rockville, Md., and designated ATCC No. 69629.

13. L5 shuttle phasmid phAE47 deposited on May 20, 1994 with the American Type Culture Collection, Rockville, Md., and designated ATCC No. 69630.

14. L5 shuttle phasmid phAE48 deposited on May 20, 1994 with the American Type Culture Collection, Rockville, Md., and designated ATCC No. 69631.

15. A method of producing an L5 shuttle phasmid comprising inserting an *E. coli*-bacteriophage lambda cosmid inserted in a non-essential region of ab L5 mycobacteriophage between the PvuII restriction site at nucleotide 42,986 and the SacII restriction site at nucleotide 52,191 of the mycobacteriophage L5 genome as shown in FIG. 3.

16. The method of claim 15 further comprising foreign DNA inserted into the *E. coli*-bacteriophage lambda cosmid.

17. The method of claim 16 wherein the foreign DNA is a transposon, a reporter gene, or a gene encoding an enzyme.

18. The method of claim 17 wherein the transposon is IS1096.

19. The method of claim 17 wherein the reporter gene is a luciferase gene.

20. The method of claim 17 wherein the gene encoding an enzyme encodes a DNA-modifying enzyme, an RNA modifying enzyme or a protein modifying enzyme.

* * * * *